(12) United States Patent
Schmid et al.

(10) Patent No.: US 9,173,751 B2
(45) Date of Patent: Nov. 3, 2015

(54) SLIDE-AND-LOCK STENT

(75) Inventors: Eric V. Schmid, San Diego, CA (US); John D. Nguyen, San Diego, CA (US); Steven C. Howard, San Diego, CA (US); Orlando M. Padilla, Laguna Niguel, CA (US); Andrew Morris, San Diego, CA (US); Robert F. Eisele, Carlsbad, CA (US); Daniel Moore, San Diego, CA (US); Thomas R. Jackson, La Jolla, CA (US); Joan Zeltinger, Encinitas, CA (US)

(73) Assignee: REVA MEDICAL, INC., San Diego, CA (US)

( * ) Notice: Subject to any disclaimer, the term of this patent is extended or adjusted under 35 U.S.C. 154(b) by 424 days.

(21) Appl. No.: 13/615,339

(22) Filed: Sep. 13, 2012

(65) Prior Publication Data
US 2013/0253631 A1    Sep. 26, 2013

Related U.S. Application Data

(62) Division of application No. 11/016,269, filed on Dec. 17, 2004, now Pat. No. 8,292,944.

(51) Int. Cl.
*A61F 2/93* (2013.01)
*A61F 2/82* (2013.01)
*A61F 2/92* (2013.01)

(52) U.S. Cl.
CPC ... *A61F 2/82* (2013.01); *A61F 2/92* (2013.01); *A61F 2/93* (2013.01); *A61F 2210/0076* (2013.01); *A61F 2220/005* (2013.01); *A61F 2220/0058* (2013.01)

(58) Field of Classification Search
CPC ...... A61F 2/92; A61F 2/93; A61F 2210/0076
USPC .......................... 606/191, 194; 623/1.11–1.54
See application file for complete search history.

(56) References Cited

U.S. PATENT DOCUMENTS

| 2,361,506 A | 10/1944 | Gray et al. |
| 3,620,218 A | 11/1971 | Schmitt |
| 4,261,390 A | 4/1981 | Belofsky |
| 4,383,555 A | 5/1983 | Finley |
| 4,553,545 A | 11/1985 | Maass et al. |
| 4,576,532 A | 3/1986 | Hanson et al. |

(Continued)

FOREIGN PATENT DOCUMENTS

| AU | 2013204977 B2 | 5/2014 |
| AU | 2009282633 | 5/2015 |

(Continued)

OTHER PUBLICATIONS

Office Action received in corresponding Canadian Application No. 2628491, dated Oct. 29, 2012, 3 pages.

(Continued)

*Primary Examiner* — Kathleen Holwerda
(74) *Attorney, Agent, or Firm* — Knobbe Martens Olson and Bear LLP

(57) ABSTRACT

The invention relates to an expandable stent comprising circumferentially adjacent modules. The modules comprise longitudinally adjacent slide-and-lock radial elements which permit one-way sliding of the radial elements from a collapsed diameter to an expanded/deployed diameter, but inhibit radial recoil from the expanded diameter.

23 Claims, 41 Drawing Sheets

(56) References Cited

U.S. PATENT DOCUMENTS

| | | |
|---|---|---|
| 4,714,508 A | 12/1987 | Chivens et al. |
| 4,733,665 A | 3/1988 | Palmaz |
| 4,739,762 A | 4/1988 | Palmaz |
| 4,740,207 A | 4/1988 | Kreamer |
| 4,748,982 A | 6/1988 | Horzewski et al. |
| 4,762,129 A | 8/1988 | Bonzel |
| 4,776,337 A | 10/1988 | Palmaz |
| 4,788,751 A | 12/1988 | Shely et al. |
| 4,817,600 A | 4/1989 | Herms et al. |
| 4,877,030 A | 10/1989 | Beck et al. |
| 4,922,905 A | 5/1990 | Strecker |
| 4,954,126 A | 9/1990 | Wallstén |
| 4,980,449 A | 12/1990 | Kohn et al. |
| 5,007,926 A | 4/1991 | Derbyshire |
| 5,040,548 A | 8/1991 | Yock |
| 5,059,211 A | 10/1991 | Stack et al. |
| 5,061,273 A | 10/1991 | Yock |
| 5,092,877 A | 3/1992 | Pinchuk |
| 5,099,060 A | 3/1992 | Kohn et al. |
| 5,108,416 A | 4/1992 | Ryan et al. |
| 5,108,417 A | 4/1992 | Sawyer |
| 5,140,094 A | 8/1992 | Kohn et al. |
| 5,151,100 A | 9/1992 | Abele et al. |
| 5,158,548 A | 10/1992 | Lau et al. |
| 5,192,307 A | 3/1993 | Wall |
| 5,194,570 A | 3/1993 | Kohn et al. |
| 5,195,984 A | 3/1993 | Schatz |
| 5,197,978 A | 3/1993 | Hess |
| 5,198,507 A | 3/1993 | Kohn et al. |
| 5,216,115 A | 6/1993 | Kohn et al. |
| 5,230,349 A | 7/1993 | Langberg |
| 5,232,445 A | 8/1993 | Bonzel |
| 5,242,399 A | 9/1993 | Lau et al. |
| 5,242,997 A | 9/1993 | Kohn et al. |
| 5,264,537 A | 11/1993 | Kohn et al. |
| 5,266,073 A | 11/1993 | Wall |
| 5,282,823 A | 2/1994 | Schwartz et al. |
| 5,300,085 A | 4/1994 | Yock |
| 5,306,286 A | 4/1994 | Stack et al. |
| 5,306,294 A | 4/1994 | Winston et al. |
| 5,314,472 A | 5/1994 | Fontaine |
| 5,317,077 A | 5/1994 | Kohn et al. |
| 5,344,426 A | 9/1994 | Lau et al. |
| 5,350,395 A | 9/1994 | Yock |
| 5,397,355 A | 3/1995 | Marin et al. |
| 5,402,554 A * | 4/1995 | Oetiker ............ 24/20 R |
| 5,421,955 A | 6/1995 | Lau et al. |
| 5,423,321 A | 6/1995 | Fontenot |
| 5,423,885 A | 6/1995 | Williams |
| 5,441,515 A | 8/1995 | Khosravi et al. |
| 5,443,496 A | 8/1995 | Schwartz et al. |
| 5,443,500 A | 8/1995 | Sigwart |
| 5,445,646 A | 8/1995 | Euteneuer et al. |
| 5,449,382 A | 9/1995 | Dayton |
| 5,451,233 A | 9/1995 | Yock |
| 5,464,450 A | 11/1995 | Buscemi et al. |
| 5,476,508 A | 12/1995 | Amstrup |
| 5,484,449 A | 1/1996 | Amundson et al. |
| 5,490,962 A | 2/1996 | Cima et al. |
| 5,496,275 A | 3/1996 | Sirhan et al. |
| 5,496,346 A | 3/1996 | Horzewski et al. |
| 5,514,154 A | 5/1996 | Lau et al. |
| 5,527,337 A | 6/1996 | Stack et al. |
| 5,545,135 A | 8/1996 | Iacob et al. |
| 5,545,138 A | 8/1996 | Fugoso et al. |
| 5,549,556 A | 8/1996 | Ndondo-Lay et al. |
| 5,549,662 A * | 8/1996 | Fordenbacher ............ 623/1.17 |
| 5,551,954 A | 9/1996 | Buscemi et al. |
| 5,554,182 A | 9/1996 | Dinh et al. |
| 5,556,413 A | 9/1996 | Lam |
| 5,571,166 A | 11/1996 | Dinh et al. |
| 5,575,816 A | 11/1996 | Rudnick et al. |
| 5,578,075 A | 11/1996 | Dayton |
| 5,587,507 A | 12/1996 | Kohn et al. |
| 5,591,172 A | 1/1997 | Bachmann et al. |
| 5,591,223 A | 1/1997 | Lock et al. |
| 5,591,224 A | 1/1997 | Schwartz et al. |
| 5,591,227 A | 1/1997 | Dinh et al. |
| 5,599,352 A | 2/1997 | Dinh et al. |
| 5,603,722 A | 2/1997 | Phan et al. |
| 5,607,463 A | 3/1997 | Schwartz et al. |
| 5,618,299 A | 4/1997 | Khosravi et al. |
| 5,626,600 A | 5/1997 | Horzewski et al. |
| 5,628,785 A | 5/1997 | Schwartz et al. |
| 5,629,077 A | 5/1997 | Turnlund et al. |
| 5,632,771 A | 5/1997 | Boatman et al. |
| 5,643,312 A | 7/1997 | Fischell et al. |
| 5,643,314 A | 7/1997 | Carpenter et al. |
| 5,643,339 A | 7/1997 | Kavteladze et al. |
| 5,649,977 A | 7/1997 | Campbell |
| 5,651,174 A | 7/1997 | Schwartz et al. |
| 5,658,995 A | 8/1997 | Kohn et al. |
| 5,670,602 A | 9/1997 | Kohn et al. |
| 5,681,345 A | 10/1997 | Euteneuer |
| 5,697,967 A | 12/1997 | Dinh et al. |
| 5,707,387 A | 1/1998 | Wijay |
| 5,725,549 A | 3/1998 | Lam |
| 5,733,328 A | 3/1998 | Fordenbacher |
| 5,735,872 A | 4/1998 | Carpenter et al. |
| 5,741,293 A | 4/1998 | Wijay |
| 5,749,888 A | 5/1998 | Yock |
| 5,755,708 A | 5/1998 | Segal |
| 5,759,186 A | 6/1998 | Bachmann et al. |
| 5,766,710 A | 6/1998 | Turnlund et al. |
| 5,769,868 A | 6/1998 | Yock |
| 5,797,951 A | 8/1998 | Mueller |
| 5,799,384 A | 9/1998 | Schwartz et al. |
| 5,800,393 A | 9/1998 | Sahota |
| 5,800,456 A | 9/1998 | Maeda et al. |
| 5,800,507 A | 9/1998 | Schwartz |
| 5,833,707 A * | 11/1998 | McIntyre et al. ............ 606/198 |
| 5,836,965 A | 11/1998 | Jendersee et al. |
| 5,843,175 A | 12/1998 | Frantzen |
| 5,849,034 A | 12/1998 | Schwartz |
| 5,851,217 A | 12/1998 | Wolff et al. |
| 5,851,231 A | 12/1998 | Wolff et al. |
| 5,855,600 A * | 1/1999 | Alt ............ 623/1.15 |
| 5,855,802 A | 1/1999 | Acciai et al. |
| 5,868,747 A | 2/1999 | Ochoa et al. |
| 5,876,419 A | 3/1999 | Carpenter et al. |
| 5,893,840 A | 4/1999 | Hull et al. |
| 5,906,639 A | 5/1999 | Rudnick et al. |
| 5,910,816 A | 6/1999 | Fontenot et al. |
| 5,921,952 A | 7/1999 | Desmond, III et al. |
| 5,944,726 A | 8/1999 | Blaeser et al. |
| 5,951,586 A | 9/1999 | Berg et al. |
| 5,954,729 A | 9/1999 | Bachmann et al. |
| 5,957,971 A | 9/1999 | Schwartz |
| 5,957,975 A | 9/1999 | Lafont et al. |
| 5,976,181 A | 11/1999 | Whelan et al. |
| 5,984,963 A | 11/1999 | Ryan et al. |
| 5,989,280 A | 11/1999 | Euteneur et al. |
| 6,007,545 A | 12/1999 | Venturelli |
| 6,015,387 A | 1/2000 | Schwartz et al. |
| 6,019,779 A | 2/2000 | Thorud et al. |
| 6,019,785 A | 2/2000 | Strecker |
| 6,033,436 A | 3/2000 | Steinke et al. |
| 6,036,715 A | 3/2000 | Yock |
| 6,048,521 A | 4/2000 | Kohn et al. |
| 6,059,825 A | 5/2000 | Hobbs et al. |
| 6,063,111 A | 5/2000 | Hieshima et al. |
| 6,066,169 A | 5/2000 | McGuinness |
| 6,080,190 A | 6/2000 | Schwartz |
| 6,080,191 A | 6/2000 | Summers |
| 6,093,157 A | 7/2000 | Chandrasekaran |
| 6,120,491 A | 9/2000 | Kohn et al. |
| 6,123,721 A | 9/2000 | Jang |
| 6,125,523 A | 10/2000 | Brown et al. |
| 6,132,457 A | 10/2000 | Chobotov |
| 6,156,062 A | 12/2000 | McGuiness |
| 6,159,239 A | 12/2000 | Greenhalgh |
| 6,160,084 A | 12/2000 | Langer et al. |
| 6,171,334 B1 | 1/2001 | Cox |
| 6,174,328 B1 | 1/2001 | Cragg |

(56) References Cited

U.S. PATENT DOCUMENTS

| | | |
|---|---|---|
| 6,179,878 B1 | 1/2001 | Duerig et al. |
| 6,183,503 B1 | 2/2001 | Hart et al. |
| 6,190,403 B1 | 2/2001 | Fishchell et al. |
| 6,197,789 B1 | 3/2001 | Grainger |
| 6,214,037 B1 | 4/2001 | Mitchell et al. |
| 6,224,626 B1 | 5/2001 | Steinke |
| 6,238,430 B1 | 5/2001 | Klumb et al. |
| 6,258,117 B1 | 7/2001 | Camrud et al. |
| 6,262,079 B1 | 7/2001 | Grainger et al. |
| 6,264,624 B1 | 7/2001 | Desmond, III et al. |
| 6,264,672 B1 | 7/2001 | Fisher |
| 6,280,473 B1 | 8/2001 | Lemperle et al. |
| 6,283,983 B1 | 9/2001 | Makower et al. |
| 6,284,862 B1 | 9/2001 | Kohn et al. |
| 6,287,329 B1 | 9/2001 | Duerig et al. |
| 6,287,333 B1 | 9/2001 | Appling et al. |
| 6,302,907 B1 | 10/2001 | Hijlkema |
| 6,309,350 B1 | 10/2001 | Van Tassel et al. |
| 6,319,277 B1 | 11/2001 | Rudnick et al. |
| 6,319,492 B1 | 11/2001 | Kohn et al. |
| 6,322,586 B1 | 11/2001 | Monroe et al. |
| 6,350,277 B1 | 2/2002 | Kocur |
| 6,359,102 B1 | 3/2002 | Kemnitzer et al. |
| 6,361,558 B1 | 3/2002 | Hieshima et al. |
| 6,375,677 B1 | 4/2002 | Penn et al. |
| 6,383,211 B1 | 5/2002 | Staehle |
| 6,388,043 B1 | 5/2002 | Langer et al. |
| 6,391,032 B2 | 5/2002 | Blaeser et al. |
| 6,406,490 B1 | 6/2002 | Roth |
| 6,409,750 B1 | 6/2002 | Hyodoh et al. |
| 6,409,752 B1 | 6/2002 | Boatman et al. |
| 6,425,915 B1 | 7/2002 | Khosravi et al. |
| 6,447,508 B1 | 9/2002 | Sharkey et al. |
| 6,451,034 B1 | 9/2002 | Gifford, III et al. |
| 6,458,152 B1 | 10/2002 | Khosravi et al. |
| 6,475,477 B1 | 11/2002 | Kohn et al. |
| 6,485,510 B1 | 11/2002 | Camrud et al. |
| 6,488,700 B2 | 12/2002 | Klumb et al. |
| 6,491,704 B2 | 12/2002 | Gifford, III et al. |
| 6,491,705 B2 | 12/2002 | Gifford, III et al. |
| 6,491,938 B2 | 12/2002 | Kunz et al. |
| 6,497,671 B2 | 12/2002 | Ferrera et al. |
| 6,527,791 B2 | 3/2003 | Fisher |
| 6,530,940 B2 | 3/2003 | Fisher |
| 6,530,958 B1 | 3/2003 | Cima et al. |
| 6,562,021 B1 | 5/2003 | Derbin et al. |
| 6,565,582 B2 | 5/2003 | Gifford, III et al. |
| 6,565,596 B1 | 5/2003 | White et al. |
| 6,569,191 B1 | 5/2003 | Hogan |
| 6,569,441 B2 | 5/2003 | Kunz et al. |
| 6,582,458 B1 | 6/2003 | White et al. |
| 6,582,472 B2 | 6/2003 | Hart |
| 6,585,760 B1 | 7/2003 | Fogarty |
| 6,602,497 B1 | 8/2003 | Kohn et al. |
| 6,607,551 B1 | 8/2003 | Sullivan et al. |
| 6,610,086 B1 | 8/2003 | Kock et al. |
| 6,613,073 B1 | 9/2003 | White et al. |
| 6,620,356 B1 | 9/2003 | Wong et al. |
| 6,623,491 B2 | 9/2003 | Thompson |
| 6,623,518 B2 | 9/2003 | Thompson et al. |
| 6,623,521 B2 | 9/2003 | Steinke et al. |
| 6,645,143 B2 | 11/2003 | Van Tassel et al. |
| 6,652,555 B1 | 11/2003 | Van Tassel et al. |
| 6,659,105 B2 | 12/2003 | Burbank et al. |
| 6,676,658 B2 | 1/2004 | Burbank et al. |
| 6,682,541 B1 | 1/2004 | Gifford, III et al. |
| 6,685,736 B1 | 2/2004 | White et al. |
| 6,689,153 B1 | 2/2004 | Skiba |
| 6,689,158 B1 | 2/2004 | White et al. |
| 6,695,857 B2 | 2/2004 | Gifford, III et al. |
| 6,699,257 B2 | 3/2004 | Gifford, III et al. |
| 6,699,280 B2 | 3/2004 | Camrud et al. |
| 6,702,846 B2 | 3/2004 | Mikus et al. |
| 6,709,449 B2 | 3/2004 | Camrud et al. |
| 6,720,402 B2 | 4/2004 | Langer et al. |
| 6,736,838 B1 | 5/2004 | Richter |
| 6,736,844 B1 | 5/2004 | Glatt et al. |
| 6,746,477 B2 | 6/2004 | Moore |
| 6,749,627 B2 | 6/2004 | Thompson et al. |
| 6,786,922 B2 | 9/2004 | Schaeffer |
| 6,790,221 B2 | 9/2004 | Monroe et al. |
| 6,792,979 B2 | 9/2004 | Konya et al. |
| 6,802,849 B2 | 10/2004 | Blaeser et al. |
| 6,821,292 B2 | 11/2004 | Pazienza et al. |
| 6,852,308 B2 | 2/2005 | Kohn et al. |
| 6,869,143 B2 | 3/2005 | Secord |
| 6,878,159 B2 | 4/2005 | Iwasaka et al. |
| 6,878,162 B2 | 4/2005 | Bales et al. |
| 6,916,868 B2 | 7/2005 | Kemnitzer et al. |
| 6,929,709 B2 | 8/2005 | Smith |
| 6,951,053 B2 | 10/2005 | Padilla et al. |
| 6,962,604 B2 | 11/2005 | Hijlkema |
| 6,964,680 B2 | 11/2005 | Shanley |
| 6,974,472 B2 | 12/2005 | Hong et al. |
| 6,974,475 B1 | 12/2005 | Wall |
| 6,991,647 B2 | 1/2006 | Jadhav |
| 7,041,126 B2 | 5/2006 | Shin et al. |
| 7,056,493 B2 | 6/2006 | Kohn et al. |
| 7,077,860 B2 | 7/2006 | Yan et al. |
| 7,128,756 B2 | 10/2006 | Lowe et al. |
| 7,141,063 B2 | 11/2006 | White et al. |
| 7,175,653 B2 | 2/2007 | Gaber |
| 7,229,473 B2 | 6/2007 | Falotico et al. |
| 7,255,710 B2 | 8/2007 | White et al. |
| 7,329,277 B2 | 2/2008 | Addonizio et al. |
| 7,520,893 B2 | 4/2009 | Rivelli |
| 7,553,377 B1 | 6/2009 | Chen et al. |
| 7,704,275 B2 | 4/2010 | Schmid et al. |
| 7,722,662 B2 | 5/2010 | Steinke et al. |
| 7,763,065 B2 | 7/2010 | Schmid et al. |
| 7,763,067 B2 | 7/2010 | Bales et al. |
| 7,766,960 B2 | 8/2010 | Alexander et al. |
| 7,780,721 B2 | 8/2010 | Bales et al. |
| 7,846,198 B2 | 12/2010 | Hogendijk |
| 7,947,071 B2 | 5/2011 | Schmid |
| 7,988,721 B2 | 8/2011 | Morris et al. |
| 8,172,894 B2 | 5/2012 | Schmid et al. |
| 8,277,500 B2 | 10/2012 | Schmid et al. |
| 8,292,944 B2 | 10/2012 | Schmid et al. |
| 8,460,363 B2 | 6/2013 | Schmid et al. |
| 8,512,394 B2 | 8/2013 | Schmid et al. |
| 8,523,936 B2 | 9/2013 | Schmid et al. |
| 8,540,762 B2 | 9/2013 | Schmid et al. |
| 8,545,547 B2 | 10/2013 | Schmid et al. |
| 8,617,235 B2 | 12/2013 | Schmid et al. |
| 9,066,827 B2 | 6/2015 | Schmid et al. |
| 2001/0010015 A1 | 7/2001 | Hijlkema |
| 2001/0020173 A1 | 9/2001 | Klumb et al. |
| 2001/0029378 A1 | 10/2001 | Blaeser et al. |
| 2001/0044651 A1 | 11/2001 | Steinke et al. |
| 2002/0010504 A1 | 1/2002 | Alt et al. |
| 2002/0040238 A1 | 4/2002 | Rudnick et al. |
| 2002/0052641 A1 | 5/2002 | Monroe et al. |
| 2002/0072656 A1 | 6/2002 | Van Tassel et al. |
| 2002/0077693 A1 | 6/2002 | Barclay et al. |
| 2002/0082682 A1 | 6/2002 | Barclay et al. |
| 2002/0095204 A1 | 7/2002 | Thompson et al. |
| 2002/0099431 A1 | 7/2002 | Armstrong et al. |
| 2002/0111669 A1 | 8/2002 | Pazienza et al. |
| 2002/0116044 A1 | 8/2002 | Cottone et al. |
| 2002/0120322 A1 | 8/2002 | Thompson et al. |
| 2002/0120323 A1 | 8/2002 | Thompson et al. |
| 2002/0123791 A1 | 9/2002 | Harrison |
| 2002/0138081 A1 | 9/2002 | Blaeser et al. |
| 2002/0138126 A1 | 9/2002 | Camrud et al. |
| 2002/0147489 A1 | 10/2002 | Hong et al. |
| 2002/0151967 A1 | 10/2002 | Mikus et al. |
| 2002/0156456 A1 | 10/2002 | Fisher |
| 2002/0156457 A1 | 10/2002 | Fisher |
| 2002/0193870 A1 | 12/2002 | Jang |
| 2003/0045923 A1 | 3/2003 | Bashiri |
| 2003/0069633 A1 | 4/2003 | Richter et al. |
| 2003/0074043 A1 | 4/2003 | Thompson |
| 2003/0078649 A1 | 4/2003 | Camrud et al. |

(56) References Cited

U.S. PATENT DOCUMENTS

| | | |
|---|---|---|
| 2003/0120334 A1 | 6/2003 | Gerberding |
| 2003/0176914 A1 | 9/2003 | Rabkin et al. |
| 2003/0199969 A1 | 10/2003 | Steinke et al. |
| 2003/0208262 A1 | 11/2003 | Gaber |
| 2003/0211135 A1 | 11/2003 | Greenhalgh et al. |
| 2003/0212451 A1 | 11/2003 | Cox et al. |
| 2003/0220682 A1 | 11/2003 | Kujawski |
| 2004/0024446 A1 | 2/2004 | Smith |
| 2004/0044401 A1 | 3/2004 | Bales et al. |
| 2004/0054400 A1 | 3/2004 | Granada |
| 2004/0062788 A1 | 4/2004 | Richter |
| 2004/0068316 A1 | 4/2004 | Schaeffer |
| 2004/0086458 A1 | 5/2004 | Kohn et al. |
| 2004/0086462 A1 | 5/2004 | Kohn et al. |
| 2004/0093073 A1 | 5/2004 | Lowe et al. |
| 2004/0093076 A1 | 5/2004 | White et al. |
| 2004/0097959 A1 | 5/2004 | Thompson |
| 2004/0106971 A1 | 6/2004 | Schwartz et al. |
| 2004/0106977 A1 | 6/2004 | Sullivan et al. |
| 2004/0127971 A1 | 7/2004 | Padilla et al. |
| 2004/0133260 A1 | 7/2004 | Schwartz et al. |
| 2004/0143319 A1 | 7/2004 | Schwartz et al. |
| 2004/0167616 A1 | 8/2004 | Camrud et al. |
| 2004/0186551 A1 | 9/2004 | Kao et al. |
| 2004/0186556 A1 | 9/2004 | Hogendijk et al. |
| 2004/0186557 A1 | 9/2004 | Gambale et al. |
| 2004/0191175 A1 | 9/2004 | Kohn et al. |
| 2004/0193251 A1 | 9/2004 | Rudnick et al. |
| 2004/0224003 A1 | 11/2004 | Schultz |
| 2004/0236401 A1 | 11/2004 | Shin et al. |
| 2004/0243217 A1 | 12/2004 | Andersen et al. |
| 2004/0243218 A1 | 12/2004 | Schaeffer |
| 2005/0038497 A1 | 2/2005 | Neuendorf et al. |
| 2005/0038503 A1 | 2/2005 | Greenhalgh et al. |
| 2005/0106119 A1 | 5/2005 | Brandom et al. |
| 2005/0123481 A1 | 6/2005 | Kohn et al. |
| 2005/0165203 A1 | 7/2005 | Kohn et al. |
| 2005/0203615 A1 | 9/2005 | Forster et al. |
| 2005/0216076 A1 | 9/2005 | Kveen et al. |
| 2005/0246010 A1 | 11/2005 | Alexander et al. |
| 2006/0020324 A1* | 1/2006 | Schmid et al. ............... 623/1.16 |
| 2006/0024266 A1 | 2/2006 | Brandom et al. |
| 2006/0026815 A1 | 2/2006 | Padilla et al. |
| 2006/0030934 A1 | 2/2006 | Hogendijk et al. |
| 2006/0034769 A1 | 2/2006 | Kohn et al. |
| 2006/0036316 A1 | 2/2006 | Zeltinger et al. |
| 2006/0079955 A1 | 4/2006 | Brown |
| 2006/0115449 A1 | 6/2006 | Pacetti |
| 2006/0136041 A1 | 6/2006 | Schmid et al. |
| 2006/0182779 A1 | 8/2006 | Brandom et al. |
| 2006/0204440 A1 | 9/2006 | Kohn et al. |
| 2007/0010870 A1 | 1/2007 | Alt et al. |
| 2007/0032854 A1 | 2/2007 | Schmid et al. |
| 2007/0032857 A1 | 2/2007 | Schmid et al. |
| 2007/0061004 A1 | 3/2007 | Steinke |
| 2007/0142901 A1 | 6/2007 | Steinke |
| 2007/0250148 A1 | 10/2007 | Perry et al. |
| 2007/0270939 A1 | 11/2007 | Hood et al. |
| 2008/0195190 A1 | 8/2008 | Bland et al. |
| 2008/0249608 A1 | 10/2008 | Dave |
| 2008/0262599 A1 | 10/2008 | Caro et al. |
| 2008/0288050 A1 | 11/2008 | Addonizio et al. |
| 2009/0030501 A1 | 1/2009 | Morris et al. |
| 2009/0143853 A1 | 6/2009 | Morris et al. |
| 2010/0042203 A1 | 2/2010 | Cottone et al. |
| 2010/0114297 A1 | 5/2010 | Calisse |
| 2010/0280593 A1 | 11/2010 | Richter |
| 2010/0292773 A1 | 11/2010 | Schmid et al. |
| 2010/0324662 A1 | 12/2010 | Addonizio et al. |
| 2011/0172759 A1 | 7/2011 | Schmid et al. |
| 2011/0245909 A1 | 10/2011 | Schmid et al. |
| 2011/0251674 A1 | 10/2011 | Schmid et al. |
| 2011/0282434 A1 | 11/2011 | Morris et al. |
| 2012/0221097 A1 | 8/2012 | Schmid et al. |
| 2014/0025159 A1 | 1/2014 | Morris et al. |
| 2014/0067042 A1 | 3/2014 | Schmid et al. |
| 2014/0277375 A1 | 9/2014 | Weier et al. |

FOREIGN PATENT DOCUMENTS

| | | |
|---|---|---|
| CA | 2368659 | 10/2000 |
| CA | 2590672 | 4/2014 |
| CA | 2573886 C | 9/2014 |
| CN | 102245127 B | 6/2014 |
| CN | 101262835 B | 7/2015 |
| EP | 0712614 | 5/1996 |
| EP | 0756853 | 2/1997 |
| EP | 1341481 | 3/2015 |
| JP | 07-000531 | 1/1995 |
| JP | 08-196641 | 8/1996 |
| JP | 08-336598 | 12/1996 |
| JP | 9-313617 | 12/1997 |
| JP | 2007-185363 | 7/2007 |
| JP | 5559798 | 6/2014 |
| JP | 5649574 | 1/2015 |
| WO | WO 90/14046 A1 | 11/1990 |
| WO | WO 94/21196 A2 | 9/1994 |
| WO | WO 94/21196 A3 | 2/1995 |
| WO | WO 96/14030 A1 | 5/1996 |
| WO | WO 97/07751 A1 | 3/1997 |
| WO | WO 97/42911 A1 | 11/1997 |
| WO | WO 98/22045 | 5/1998 |
| WO | WO 98/22073 A2 | 5/1998 |
| WO | WO 98/41169 A1 | 9/1998 |
| WO | WO 98/22073 A3 | 2/1999 |
| WO | WO 99/08740 A1 | 2/1999 |
| WO | WO 99/15106 A1 | 4/1999 |
| WO | WO 99/40874 A1 | 8/1999 |
| WO | WO 99/65421 A2 | 12/1999 |
| WO | WO 99/65421 A3 | 1/2000 |
| WO | WO 00/09195 A1 | 2/2000 |
| WO | WO 00/10623 A1 | 3/2000 |
| WO | WO 00/30565 A1 | 6/2000 |
| WO | WO 00/59405 A1 | 10/2000 |
| WO | WO 00/62708 A1 | 10/2000 |
| WO | WO 00/71058 A1 | 11/2000 |
| WO | WO 01/24735 A1 | 4/2001 |
| WO | WO 01/35864 A1 | 5/2001 |
| WO | WO 01/51114 A2 | 7/2001 |
| WO | WO 01/70298 A2 | 9/2001 |
| WO | WO 01/87180 A2 | 11/2001 |
| WO | WO 01/51114 A3 | 1/2002 |
| WO | WO 01/70298 A3 | 2/2002 |
| WO | WO 00/62708 C2 | 6/2002 |
| WO | WO 01/87180 A3 | 6/2002 |
| WO | WO 02/047582 A2 | 6/2002 |
| WO | WO 02/053204 A2 | 7/2002 |
| WO | WO 02/054990 A2 | 7/2002 |
| WO | WO 02/047582 A3 | 10/2002 |
| WO | WO 02/054990 A3 | 11/2002 |
| WO | WO 02/053204 A3 | 3/2003 |
| WO | WO 03/022178 A1 | 3/2003 |
| WO | WO 03/047464 A2 | 6/2003 |
| WO | WO 03/057076 A1 | 7/2003 |
| WO | WO 03/047464 A3 | 9/2003 |
| WO | WO 03/047464 C2 | 11/2003 |
| WO | WO 03/094798 A1 | 11/2003 |
| WO | WO 03/099161 A2 | 12/2003 |
| WO | WO 03/099161 A3 | 2/2004 |
| WO | WO 2004/019820 A1 | 3/2004 |
| WO | WO 2004/026112 A2 | 4/2004 |
| WO | WO 2004/032803 A1 | 4/2004 |
| WO | WO 2004/026112 C2 | 6/2004 |
| WO | WO 2004/026112 A3 | 10/2004 |
| WO | WO 2004/087015 | 10/2004 |
| WO | WO 2004/096340 A1 | 11/2004 |
| WO | WO 2004/110312 A1 | 12/2004 |
| WO | WO 2006/010636 A1 | 2/2006 |
| WO | WO 2006/014596 A1 | 2/2006 |
| WO | WO 2006/014699 | 2/2006 |
| WO | WO 2006/020616 A1 | 2/2006 |
| WO | WO 2006/107608 A1 | 10/2006 |
| WO | WO 2007/016409 A1 | 2/2007 |

(56) References Cited

FOREIGN PATENT DOCUMENTS

| WO | WO 2007/084444 A2 | 7/2007 |
|---|---|---|
| WO | WO 2010/022005 A1 | 2/2010 |
| WO | WO 2010/042879 A2 | 4/2010 |
| WO | WO 2011/127452 | 10/2011 |
| WO | WO 2014/159337 A1 | 10/2014 |
| WO | WO 2014/176361 A1 | 10/2014 |

OTHER PUBLICATIONS

Office Action received in corresponding Canadian Application No. 2628491, dated Aug. 13, 2013, 2 pages.
International Search Report and Written Opinion in corresponding International Application No. PCT/US2005/045553, mailed Apr. 3, 2006, 8 pages.
International Preliminary Report on Patentability in corresponding International Application No. PCT/US2005/045553, mailed Jun. 28, 2007, 7 pages.
Office Action received in corresponding Australian Application No. 2005327112, mailed Nov. 24, 2010, 2 pages.
Office Action received in corresponding Canadian Application No. 2590672, dated Feb. 7, 2012, 3 pages.
Office Action received in corresponding Chinese Application No. 200580043545X, mailed Apr. 24, 2009, 15 pages.
Office Action received in corresponding Chinese Application No. 200580043545X, mailed Jul. 26, 2010, 10 pages.
Office Action received in corresponding Chinese Application No. 200580043545X, mailed Apr. 1, 2011, 10 pages.
Office Action received in corresponding Japanese Application No. 2007-546927, mailed May 10, 2011, 4 pages.
Office Action received in corresponding Japanese Application No. 2007-546927, mailed Mar. 27, 2012, 4 pages.
Office Action received in corresponding Russian Application No. 2007125518/14, mailed Oct. 28, 2009, 31 pages.
Office Action received in corresponding Russian Application No. 2007125518/14, mailed Apr. 2010, 21 pages.
Office Action received in corresponding Australian Application No. 2006319006, dated Feb. 6, 2012, 2 pages.
Office Action received in corresponding Chinese Application No. 200680001959.0, dated Nov. 8, 2011, 9 pages.
Office Action received in corresponding Chinese Application No. 200680001959.0, dated Mar. 31, 2012, 14 pages.
Office Action received in corresponding Japanese Application No. 2009-516462, mailed Aug. 17, 2011, 2 pages.
International Search Report and Written Opinion in corresponding International Application No. PCT/US2006/024127, mailed Mar. 2, 2007, 11 pages.
International Preliminary Report on Patentability in corresponding International Application No. PCT/US2006/024127, mailed Jan. 8, 2009, 9 pages.
Office Action received in corresponding Russian Application No. 2007131550, mailed Mar. 22, 2010, 10 pages.
Office Action received in corresponding Russian Application No. 2007131550, mailed Feb. 20, 2011.
Asahara, T. "Local delivery of vascular endothelial growth factor accelerates reendothelialization and attenuates intimal hyperplasia in balloon-insured rate carotid artery," Circulation 91: 2793-2801, 1995.
Autieri, M.V. et al. "Antisense oligonucleotides to the p65 subunit of NF-Kb inhibit human vascualr smooth muscle cell adherence and proliferation and prevent neointima formation in rat carotid arteries," Biochemical and Biophysical Research Communications 213: 827-836, 1995.
Brauner, R. "Controlled periadverntitial administration of verapamil inhibits neointimal smooth muscle cell proliferation and ameliorates vasomotor abnormalities in experimental vein bypass grafts," The Journal of Thoracic and Cardiovascular Surgery 114: 53-63, 1997.
Carmeliet, P. et al. "Inhibitory role of plasminogen activator inhibitor-1 in arterial wound healing and neointima formation," Circulation 96: 3180-3191, 1997.
Epstein, S.E. et al. "Cytotoxic effects of a recombinant chimeric toxin on rapidly proliferating vascular smooth muscle cells," Circulation 84: 778-787, 1991.
Hu, Y. "Inhibition of neointima hyperplasia of mouse vein grafts by locally applied suramin," Circulation 100: 861-868, 1999.
Kurisu, Y. et al. "Protective effect of beraprost sodium, a stable prostacyclin analogue, on cardiac allograft vasculopathy in rats," Hiroshima Journal of Medical Science 56: 11-19, 1997.
Morishita, R. et al. "Novel in vitro gene transfer method for study of local modulators in vascular smooth muscle cells," Hypertension 21: 894-899, 1993.
Nerem, R.M. et al. "Tissue engineering and the vascular system, synthetic biodegradable polymer scaffolds," pp. 164-185, 1997.
Von Der Leyen, H.E. et al. "Gene therapy neointimal vascular lesion: in vivo transfer of endothelial cell nitric oxide synthase gene," PNAS USA 92:1137-1141, 1995.
Yasukawa, H. "Inhibition of intimal hyperplasia after balloon injury by antibodies to intercellular adhesion molecule-1 and lymphocyte function, Associated antigen-1," Circulation 95: 1515-1522, 1997.
Balcon, R. et al., Recommendations on stent manufacture, implantation and utilization, European Heart Journal, Oct. 1997, vol. 18, pp. 1536-1547.
Charles, Roger et al., Ceramide-Coated Balloon Catheters Limit Neointimal Hyperplasia After Stretch Injury in Carotid Arteries, Circulation Research, 2000; 87; pp. 282-288.
Coroneos, Emmanuel et al., Differential Regulation of Sphingomyelinase and Ceramidase Activities by Growth Factors and Cytokines, The Journal of Biological Chemistry, Oct. 6, 1995, vol. 270, No. 40, pp. 23305-23309.
Coroneos, Emmanuel et al., Sphingolipid metabolites differentially regulate extracellular signal-regulated kinase and stress-activated protein kinase cascades, Biochem. J., 1996; 316, pp. 13-17 (Printed in Great Britain).
Jacobs, Leila S. et al., Sphingolipids as mediators of effects of platelet-derived growth factor in vascular smooth muscle cells, Am J Physiol (American Physiological Society), 1993, pp. C740-C747.
Tanguay, Jean Francois et al., Current Status of Biodegradable Stents, Cardiology Clinics, Contemporary Interventional Techniques, Nov. 1994, vol. 12, No. 4, pp. 699-713, W.B. Saunders Company.
Nikol, S. et al., Molecular biology and post-angioplasty restenosis, Atherosclerosis, 1996; 123, pp. 17-31.
Phillips, Paul S. MD, et al., The Stenter's Notebook, 1998, (entire book), Physicians' Press, Birmingham, Michigan.
Ratner, Buddy D. et al., Biomaterials Science, An Introduction to Materials in Medicine, 2nd Edition, 2004, (entire book), Elsevier Academic Press.
Serruys, Patrick W. et al., Handbook of Coronary Stents, Fourth Edition, 2002, (entire book), Martin Dunitz Ltd.
Atala, Anthony et al., Synthetic Biodegradable Polymer Scaffolds, 1997, (entire book), Birkhauser Boston.

* cited by examiner

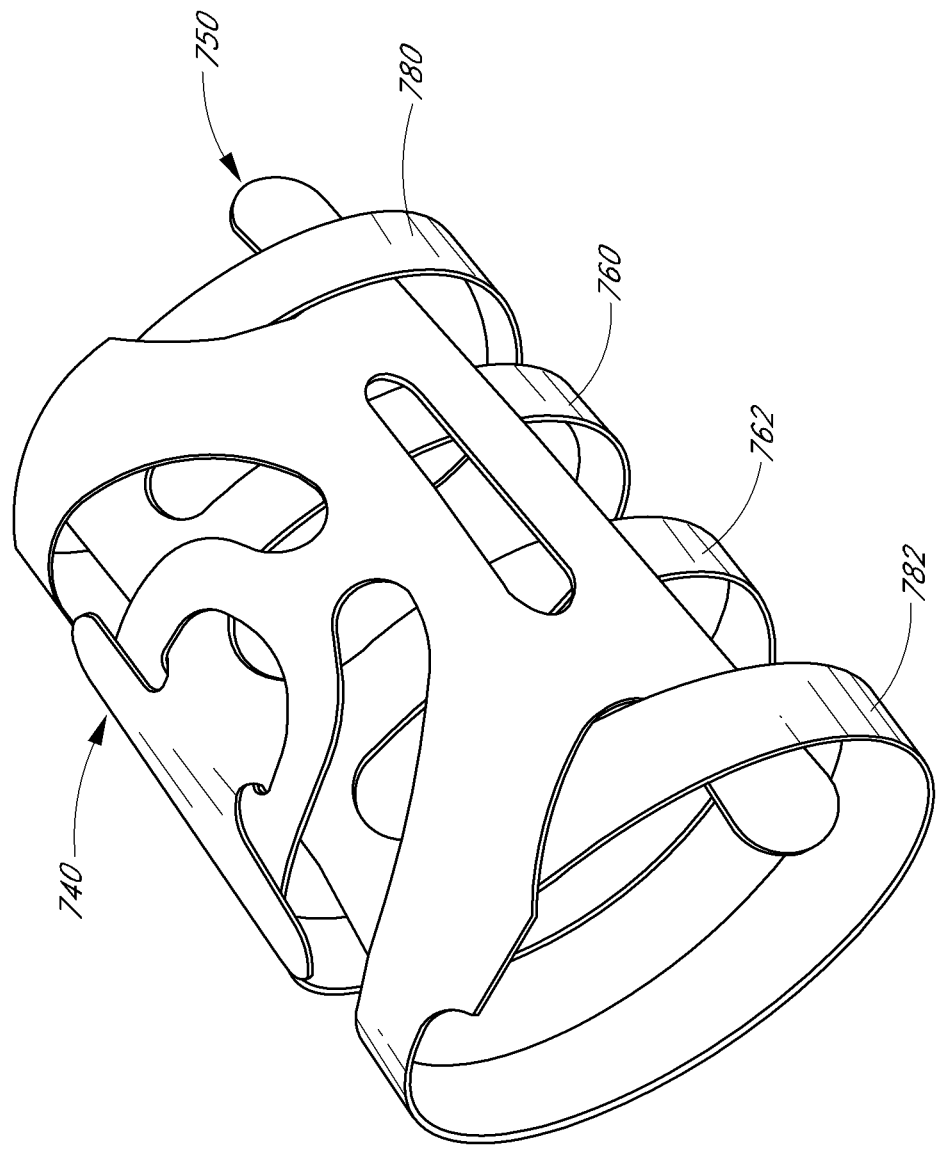

SLIDE-AND-LOCK STENT

CROSS-REFERENCE TO RELATED APPLICATIONS

This application is a divisional of U.S. Pat. application Ser. No. 11/016,269, filed on Dec. 17, 2004, the entirety of which is hereby incorporated by reference.

BACKGROUND OF THE INVENTION

1. Field of the Invention

The invention relates to expandable medical implants for maintaining support of a body lumen.

2. Description of the Related Art

Stents or expandable grafts are implanted in a variety of body lumens in an effort to maintain their patency. These devices are typically intraluminally implanted by use of a catheter, which is inserted at an easily accessible location and then advanced to the deployment site. The stent is initially in a radially compressed or collapsed state to enable it to be maneuvered through the lumen. Once in position, the stent is deployed which, depending on its configuration, may be achieved either automatically or manually, by for example, the inflation of a balloon about which the stent is carried on the catheter.

As stents are normally employed to hold open an otherwise blocked, constricted or occluded lumen, a stent must exhibit sufficient radial or hoop strength in its expanded state to effectively counter the anticipated forces. It is, however, simultaneously necessary for the stent to be as compact as possible in its collapsed state in order to facilitate its advancement through the lumen. As a result, it is advantageous for a stent to have as large an expansion ratio as possible.

An additional consideration is the longitudinal flexibility of the device. Such characteristic is important not only in maneuvering the stent into position, which may require the traversal of substantial convolutions of the vasculature, but also to better conform to any curvature of the vasculature at the deployment site. At the same time it is, however, necessary for the stent to nonetheless exhibit sufficient radial strength to provide the necessary support for the lumen walls upon deployment.

Another problem inherent in many prior art stent configurations is the longitudinal contraction that such structures typically undergo as they are radially expanded. This not only reduces the effective length of the stent in its deployed state but may cause abrasion trauma to be inflicted on the vessel walls during expansion.

A number of very different approaches have been previously devised in an effort to address these various requirements. A popular approach calls for the stent to be constructed wholly of wire. The wire is bent, woven and/or coiled to define a generally cylindrical structure in a configuration that has the ability to undergo radial expansion. The use of wire has a number of disadvantages associated therewith including for example, its substantially constant cross-section which may cause greater or lesser than an ideal amount of material to be concentrated at certain locations along the stent. Additionally, wire has limitations with respect to the shapes it can be formed into thus limiting the expansion ratio, coverage area, flexibility and strength that can ultimately be attained therewith.

As an alternative to wire-based structures, stents have been constructed from tube stock. By selectively removing material from such tubular starting material, a desired degree of flexibility and expandability can be imparted to the structure. Etching techniques as well as laser-cutting processes are utilized to remove material from the tube. Laser cutting provides for a high degree of precision and accuracy with which very well defined patterns of material can be removed from the tube to conversely leave very precisely and accurately defined patterns of material in tact. The performance of such stent is very much a function of the pattern of material which remains (i.e., design) and material thickness. The selection of a particular pattern has a profound effect on the coverage area, expansion ratio and strength of the resulting stent as well as its longitudinal flexibility and longitudinal dimensional stability during expansion.

While the tube-based stents offer many advantages over the wire-based designs, it is nonetheless desirable to improve upon such designs in an effort to further enhance longitudinal flexibility and longitudinal dimensional stability during radial expansion without sacrificing radial hoop strength.

One stent design described by Fordenbacher, see e.g., U.S. Pat. Nos. 5,549,662 and 5,733,328, employs a plurality of elongated parallel stent components, each having a longitudinal backbone with a plurality of opposing circumferential elements or fingers. The circumferential elements from one stent component weave into paired slots in the longitudinal backbone of an adjacent stent component. By incorporating locking means with the slotted articulation, the Fordenbacher stent may minimize recoil after radial expansion. In addition, sufficient members of circumferential elements in the Fordenbacher stent may provide adequate scaffolding. Unfortunately, the circumferential elements have free ends, protruding from the paired slots. Moreover, the circumferential elements weaving through the paired slots also necessarily stand off from the lumen wall. Both the free ends and the stand off may pose significant risks of thrombosis and/or restenosis. Moreover, this stent design would tend to be rather inflexible as a result of the plurality of longitudinal backbones.

Some stents employ "jelly roll" designs, wherein a sheet is rolled upon itself with a high degree of overlap in the collapsed state and a decreasing overlap as the stent unrolls to an expanded state. Examples of such designs are described in U.S. Pat. No. 5,421,955 to Lau, U.S Pat. Nos. 5,441,515 and 5,618,299 to Khosravi, and 5,443,500 to Sigwart. The disadvantage of these designs is that they tend to exhibit very poor longitudinal flexibility. In a modified design that exhibits improved longitudinal flexibility, multiple short rolls are coupled longitudinally. See e.g., U.S. Pat. No. 5,649,977 to Campbell and U.S Pat. Nos. 5,643,314 and 5,735,872 to Carpenter. However, these coupled rolls lack vessel support between adjacent rolls. Furthermore, these designs exhibit extensive overlapping of stent elements in multiple layers, which makes the delivery profile rather thick.

Various types of stents, including those referenced above, are often described based on their means for expansion. For additional information, a variety of stents types are described by Balcon et al., "Recommendations on Stent Manufacture, Implantation and Utilization," European Heart Journal (1997), vol. 18, pages 1536-1547, and Phillips, et al., "The Stenter's Notebook," Physician's Press (1998), Birmingham, Michigan.

Balloon expandable stents are manufactured in the collapsed condition and are expanded to a desired diameter with a balloon. The expandable stent structure may be held in the expanded condition by mechanical deformation of the stent as taught in, for example, U.S. Pat. No. 4,733,665 to Palmaz. Alternatively, balloon expandable stents may be held in the expanded condition by engagement of the stent walls with respect to one another as disclosed in, for example, U.S. Pat.

No. 4,740,207 to Kreamer, U.S Pat. No. 4,877,030 to Beck et al., and U.S Pat. No. 5,007,926 to Derbyshire. Further still, the stent may be held in the expanded condition by one-way engagement of the stent walls together with tissue growth into the stent, as disclosed in U.S. Pat. No. 5,059,211 to Stack et al.

Although balloon expandable stents are the first stent type to be widely used in clinical applications, it is well recognized that balloon expandable stents have a variety of shortcomings which may limit their effectiveness in many important applications. For example, balloon expandable stents often exhibit substantial recoil (i.e., a reduction in diameter) immediately following deflation of the inflatable balloon. Accordingly, it may be necessary to over-inflate the balloon during deployment of the stent to compensate for the subsequent recoil. This is disadvantageous because it has been found that over-inflation may damage the blood vessel. Furthermore, a deployed balloon expandable stent may exhibit chronic recoil over time, thereby reducing the patency of the lumen. Still further, balloon expandable stents often exhibit foreshortening (i.e., a reduction in length) during expansion, thereby creating undesirable stresses along the vessel wall and making stent placement less precise. Still further, many balloon expandable stents, such as the original Palmaz-Schatz stent and later variations, are configured with an expandable mesh having relatively jagged terminal prongs, which increases the risk of injury to the vessel, thrombosis and/or restenosis.

Self-expanding stents are manufactured with a diameter approximately equal to, or larger than, the vessel diameter and are collapsed and constrained at a smaller diameter for delivery to the treatment site. Self-expanding stents are commonly placed within a sheath or sleeve to constrain the stent in the collapsed condition during delivery. After the treatment site is reached, the constraint mechanism is removed and the stent self-expands to the expanded condition. Most commonly, self-expanding stents are made of Nitinol or other shape memory alloy. One of the first self-expanding stents used clinically is the braided "WallStent," as described in U.S. Pat. No. 4,954,126 to Wallsten. Another example of a self-expanding stent is disclosed in U.S. Pat. No. 5,192,307 to Wall wherein a stent-like prosthesis is formed of plastic or sheet metal that is expandable or contractible for placement.

Heat expandable stents are similar in nature to self-expanding stents. However, this type of stent utilizes the application of heat to produce expansion of the stent structure. Stents of this type may be formed of a shape memory alloy, such as Nitinol or other materials, such as polymers, that must go through a thermal transition to achieve a dimensional change. Heat expandable stents are often delivered to the affected area on a catheter capable of receiving a heated fluid. Heated saline or other fluid may be passed through the portion of the catheter on which the stent is located, thereby transferring heat to the stent and causing the stent to expand. However, heat expandable stents have not gained widespread popularity due to the complexity of the devices, unreliable expansion properties and difficulties in maintaining the stent in its expanded state. Still further, it has been found that the application of heat during stent deployment may damage the blood vessel.

In summary, although a wide variety of stents have been proposed over the years for maintaining the patency of a body lumen, none of the existing schemes has been capable of overcoming most or all of the above described shortcomings. As a result, clinicians are forced to weigh advantages against shortcomings when selecting a stent type to use in a particular application. Accordingly, there remains a need for an improved stent: one that is compact and flexible enough when collapsed to permit uncomplicated delivery to the affected area; one that is sufficiently flexible upon deployment to conform to the shape of the affected body lumen; one that expands uniformly to a desired diameter, without change in length; one that maintains the expanded size, without significant recoil; and one that has sufficient scaffolding to provide a clear through-lumen.

SUMMARY OF THE INVENTION

For purposes of summarizing the invention, certain aspects, advantages and novel features of the invention have been described herein above. Of course, it is to be understood that not necessarily all such advantages may be achieved in accordance with any particular embodiment of the invention. Thus, the invention may be embodied or carried out in a manner that achieves or optimizes one advantage or group of advantages as taught or suggested herein without necessarily achieving other advantages as may be taught or suggested herein.

In one embodiment, a slide-and-lock stent is disclosed. The stent comprises a tubular member having longitudinal and circumferential axes. The tubular member comprises at least two circumferentially adjacent modules, each comprising at least two slide-and-lock radial elements which are separated from one another in the longitudinal axis by at least one passive radial element, wherein each slide-and-lock radial element comprises an engaging tab and a receiving slot which comprises a lockout tooth therein and defines a travel path. The engaging tabs from the slide-and-lock radial elements from each module are slidably engaged within receiving slots in the slide-and-lock radial elements from a circumferentially adjacent module, wherein the lockout tooth is configured to permit one-way sliding of the tabs along the travel path, such that the tubular member achieves expansion in the circumferential axis with reduced recoil as the circumferentially adjacent modules slide apart from one another.

In preferred variations to the slide-and-lock stent, the travel path is aligned substantially in the circumferential axis.

In preferred variations to the slide-and-lock stent, the lockout tooth further comprises a plurality of lockout teeth which are disposed along both proximal and distal sides of the slot. Preferably, the plurality of lockout teeth are substantially evenly distributed on the proximal and distal sides of the slot. In another preferred variation, the lockout teeth on the proximal side are circumferentially offset from the lockout teeth on the distal side, such that the travel path defines a zig-zag pattern.

In preferred variations to the slide-and-lock stent, the passive radial elements further comprise a tab and a slot, wherein tabs from the passive radial elements from each module are slidably engaged within slots in the passive radial elements from a circumferentially adjacent module. Preferably, at least one slot from the passive radial elements has a safety catch configured to stop the tab at a predetermined location so as to prevent further sliding of the tab within the slot.

In yet another preferred variation to the slide-and-lock stent, at least one of the slide-and-lock radial elements further comprises an actuating catch member configured to deflect from a non-actuated position to an actuated position and back again as it passes the lockout tooth during expansion. In one variation, the stent further comprises a positive return element adapted to return the actuating catch to the non-actuated position after passing the lockout tooth. Preferably, the lockout tooth further comprises a plurality of lockout teeth which are disposed along one side of the slot. In further variations, the stent comprises a plurality of positive return elements disposed along the other side of the slot from the lockout teeth and positioned so as to return the actuating catch to the non-actuated position after passing each of the plurality of lockout teeth.

In yet another preferred embodiment, at least one of the radial elements further comprises a deformable region, such that radial expansion may occur through both sliding of circumferentially adjacent radial elements and deformation of the deformable region.

In yet another preferred variation, an engaging tab is deflectable.

In yet another preferred variation, the stent further comprising a linkage region within a module, wherein the linkage region is configured to facilitate material flexing. Preferably, the linkage region includes a structural feature selected from the group consisting of a U-shaped member, inverted U-shaped member pairs, serpentine waves, linear connectors disposed at an angle to the longitudinal and circumferential axes, and undulating spring elements.

In another preferred embodiment of the present invention, a slide-and-lock stent is disclosed comprising a tubular member having longitudinal and circumferential axes. The tubular member comprises a first radial element comprising an actuating rail having an actuator disposed thereon; a second radial element, circumferentially adjacent to the first radial element, and slidably engaged with the first radial element, the second radial element comprising a deflectable catch element; and a lockout catch, wherein the actuator is configured so that as the second radial element slides relative to the first radial element, the actuator deflects the deflectable catch element thereby engaging the lockout catch, such that the tubular member achieves expansion in the circumferential axis with reduced recoil. Preferably, the lockout catch is disposed along a frame element which surrounds the first radial element.

In another preferred embodiment of the present invention, a slide-and-lock stent is disclosed comprising a tubular member having longitudinal and circumferential axes, wherein the tubular member comprises a first radial element comprising a deflectable rail having a lockout tooth disposed thereon; and a second radial element, circumferentially adjacent to the first radial element, and slidably engaged with the first radial element, the second radial element comprising a slot, wherein the slot is configured to slidably engage and deflect the deflectable rail as the lockout tooth disposed on the deflectable rail passes through the slot, such that the tubular member achieves expansion in the circumferential axis with reduced recoil. Preferably, the deflectable rail further comprises two rails with a gap therebetween, wherein each rail has a plurality of lockout teeth disposed thereon.

In another preferred embodiment of the present invention, a slide-and-lock stent is disclosed comprising a tubular member having longitudinal and circumferential axes, wherein the tubular member comprises: a first radial element comprising an elongate rail comprising a deflectable tooth; and a second radial element, circumferentially adjacent to the first radial element, and comprising an engagement means configured to slidably engage the elongate rail of the first radial element and deflect the deflectable tooth as the tooth contacts the engagement means, such that the tubular member achieves expansion in the circumferential axis with reduced recoil.

In preferred variations, the engagement means comprises a locking tab configured to slide adjacent to the elongate rail in the longitudinal axis and deflect the tooth longitudinally toward the elongate rail.

In other preferred variations, the engagement means comprises a locking tab configured to slide over or under the elongate rail and deflect the tooth toward the plane of the elongate rail.

In other preferred variations, the engagement means comprises a closed loop which defines a slot. Preferably, the elongate rail further comprises two rail members with a gap therebetween, such that the rail members are configured to deflect toward one another into the gap when engaged by the slot.

In other preferred variations, the elongate rail has a plurality of deflectable teeth disposed thereon.

In other preferred variations, the slide-and-lock stent further comprises a first module comprising more than one of the first radial elements, linked to one another in the longitudinal axis, and second module comprising more than one of the second radial elements, linked to one another in the longitudinal axis.

In other preferred variations, the longitudinally linked radial elements in each module are circumferentially offset from one another in a zig-zig pattern.

In another preferred embodiment of the present invention, a slide-and-lock stent is disclosed comprising a tubular member having longitudinal and circumferential axes, wherein the tubular member comprises: a first radial element comprising a first serrated surface; and a second radial element, circumferentially adjacent to and slidably engaged with said first radial element, and comprising a second serrated surface, wherein the first and second serrated surfaces engage one another in a complimentary hill and valley configuration adapted to resist sliding, whereby once expanded by application of radial force, the tubular member resists recoil.

In preferred variations to the above-described stents, the longitudinally adjacent radial elements are connected to one another by a flexible linkage element.

In another preferred embodiment of the present invention, a slide-and-lock stent is disclosed comprising a tubular member having longitudinal and circumferential axes, wherein the tubular member comprises: a first module comprising at least two circumferentially offset slide-and-lock radial elements and a coupling element, wherein each radial element comprises a tab, a gap comprising lockout teeth, and a slot; and a second module configured substantially identical to the first module and circumferentially adjacent to the first module, wherein the radial elements from the second module are slidably engaged within the slots of the corresponding radial elements from the first module, and wherein the tabs of the radial elements from the second module are slidably engaged within the gaps of the corresponding radial elements from the first module, such that the lockout teeth engage the tabs to minimize recoil.

In another preferred embodiment of the present invention, a slide-and-lock stent is disclosed comprising a tubular member having longitudinal and circumferential axes, wherein the tubular member comprises: first and second longitudinal modules, each comprising peaks and valleys, wherein a protrusion comprising a lockout tooth extends from a first peak in each module, and a slot extends through a location along a second peak in each module, wherein the protrusion from the first module is slidably engaged within the slot from the second module.

In preferred variations, the modules comprise (n) material layers, wherein (n) is at least two. Preferably, the protrusion and the location each comprise less than (n) material layers, and the total number of material layers at the location equals (n) when the protrusion from the first module is slidably engaged within the slot from the second module, such that the thickness of the slide-and-lock stent is uniform and does not exceed (n) layers.

In preferred variations to the above-described stents, a cross-sectional geometry of at least a portion of the stent is tapered so as to produce generally desirable blood flow characteristics when the stent is placed in a blood vessel lumen.

In preferred variations to the above-described stents, the stent further comprises a material selected from the group consisting of metal and polymer. Preferably, the polymer comprises a bioresorbable polymer. More preferably, the polymer comprises a radiopaque, bioresorbable polymer. In one aspect, the polymer forms a coating on at least a portion of the stent. The polymer coating may further comprise a biocompatible, bioresorbable polymer adapted to promote a selected biological response.

In preferred variations to the above-described stents, the stent further comprises a layered material. Preferably, the layered material comprises a bioresorbable polymer.

In preferred variations to the above-described stents, the stent further comprises a therapeutic agent.

In preferred variations to the above-described stents, the stent further comprises a retractable sheath sized for enclosing the tubular member during delivery to a treatment site.

In preferred variations to the above-described stents, the stent further comprises a solid wall region. The solid wall region may further comprise an opening.

In preferred variations to the above-described stents, the stent further comprises a polymeric sheath.

A system for treating a site within a vessel is also disclosed. The system comprises a catheter having a deployment means, and any of the above-described stents, wherein the catheter is adapted to deliver the stent to the site and the deployment means is adapted to deploy the stent. In preferred variations, the catheter is selected from the group consisting of over-the-wire catheters, coaxial rapid-exchange catheters, and multi-exchange delivery catheters.

A method for re-treatment of a body lumen is disclosed in accordance with another embodiment of the present invention. The method comprises the steps of: deploying to a region of the body lumen any of the above described stents, wherein the stent is made from a bioresorbable polymer, and resides at the region for a period of time; and administering to the region, after the period of time, a second treatment, such as for example, treatments selected from the group consisting of a second stent of any kind, angioplasty, arthrectomy, surgical bypass, radiation, ablation, local drug infusion, etc., or any subsequent intervention or treatment.

All of these embodiments are intended to be within the scope of the invention herein disclosed. These and other embodiments of the invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and some of its features and advantages, certain preferred embodiments and modifications thereof will become apparent to those skilled in the art from the detailed description herein having reference to the figures that follow, of which:

FIG. 8 shows the elements before actuation of the active lockout mechanism and FIG. 9 shows the elements after actuation of the active lockout mechanism.

FIG. 10 shows the deformable portion in a collapsed state. FIG. 11 shows the deformable portion in an expanded state.

FIG. 16 shows the deployment control mechanism before plastic deformation of the frangible members and FIG. 17 shows the deployment control mechanism after plastic deformation of the frangible members.

FIG. 35C illustrates the single element of FIG. 35A locked out in the expanded condition.

DETAILED DESCRIPTION OF THE PREFERRED EMBODIMENT

Figure 1:
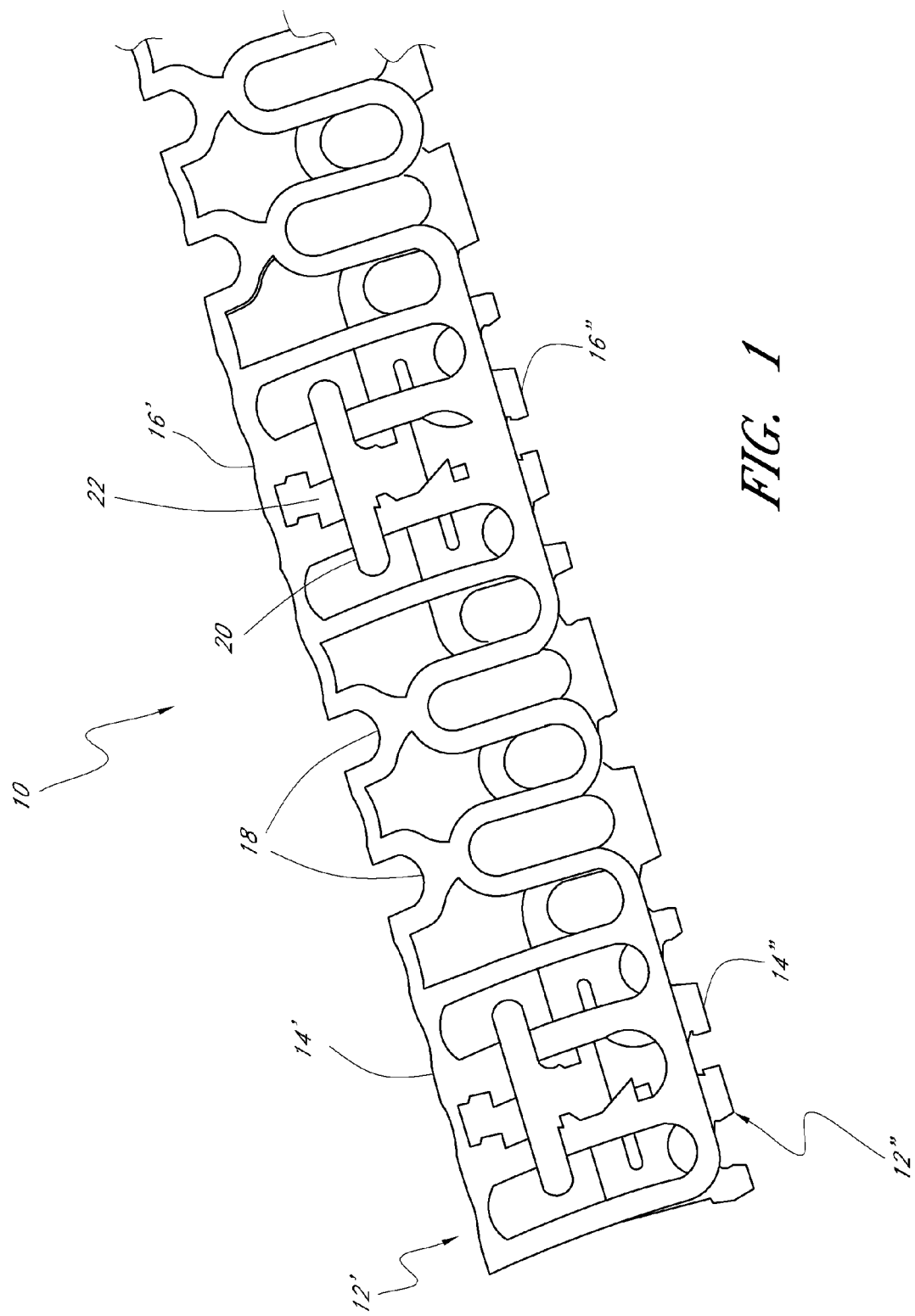
FIG. 1 is a perspective partial view of a slide-and-lock stent in a partially expanded state having features and advantages in accordance with one embodiment of the invention.

The preferred embodiments of the invention described herein relate generally to expandable medical implants for maintaining support of a body lumen. Embodiments and attributes of the invention include, but are not limited to, a non-actuating slide-and-lock stent with radial elements following a defined path geometry having both radial and axial translation; a slide-and-lock stent with longitudinal modules comprising both active (slide-and-lock) and passive radial elements wherein the radial elements have a variety of features including, but not limited to, spring elements, frangible deployment control mechanism and device overextension safety catches; a slide-and-lock stent with non-symmetric lockout geometries for enhanced sizing resolution; an actuating slide-and-lock stent with a positive lockout mechanism return; an actuating slide-and-lock stent with an active lockout system; a deformable slide-and-lock stent which provides additional device radial expansion and/or increases device safety; a slide-and-lock stent with two sided lockout features; a crimpable slide-and-lock stent for enhanced retention on a delivery balloon; a crush recoverable slide-and-lock stent; and a slide-and-lock stent with optimized strut or wall configuration to reduce turbulence and create generally laminar flow of the blood. Further embodiments include a slide-and-lock stent with a region with a high surface area region for support; a slide-and-lock stent with a region with a side-branch vessel access port; and, a slide-and-lock stent with a graft covering. Further embodiments include a slide-and-lock stent comprised of a biocompatible material (metal and/or polymer) and a slide-and-lock stent comprised of layered materials and/or spatially localized materials.

While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described herein.

The term "stent" is used herein to designate embodiments for placement in (1) vascular body lumens (i.e., arteries and/or veins) such as coronary vessels, neurovascular vessels and peripheral vessels for instance renal, iliac, femoral, popliteal, subclavian and carotid; and in (2) nonvascular body lumens such as those treated currently i.e., digestive lumens (e.g., gastrointestinal, duodenum and esophagus, biliary ducts), respiratory lumens (e.g., tracheal and bronchial), and urinary lumens (e.g., urethra); (3) additionally such embodiments may be useful in lumens of other body systems such as the reproductive, endocrine, hematopoietic and/or the integumentary, musculoskeletal/orthopedic and nervous systems (including auditory and ophthalmic applications); and, (4) finally, stent embodiments may be useful for expanding an obstructed lumen and for inducing an obstruction (e.g., as in the case of aneurysms).

In the following description of the present invention, the term "stent" may be used interchangeably with the term "prosthesis" and should be interpreted broadly to include a wide variety of devices configured for supporting a segment of a body passageway. Furthermore, it should be understood that the term "body passageway" encompasses any lumen or duct within a body, such as those described herein.

Still further, it should be understood that the term "shape-memory material" is a broad term that includes a variety of known shape memory alloys, such as nickel-titanium alloys, as well as any other materials that return to a previously defined shape after undergoing substantial plastic deformation.

In one preferred embodiment of the present invention, the assembled stent generally comprises a tubular member having a length in the longitudinal axis and a diameter in the radial or circumferential axis sized for insertion into the body lumen. The tubular member is preferably formed with a "clear through-lumen," which is defined as having little or no structure protruding into the lumen in either the collapsed or expanded condition.

In many of the embodiments illustrated and described herein, the intraluminal stent is preferably provided with "slide-and-lock elements" generally referred to herein as "radial elements." The radial elements are slidably interconnected with circumferentially adjacent radial elements in a manner wherein the stent exhibits mono-directional radial expansion from a radially collapsed state to a radially expanded state, e.g., during deployment. The radial elements are preferably configured to provide a ratcheting effect such that the stent is maintained (i.e., "locked-out") in the expanded diameter after deployment within the body passage. More particularly, the structures (e.g., radial elements) may flex or bend; however, unlike conventional balloon expandable stents, no substantial plastic deformation of the elements are required during expansion of the stent from a collapsed diameter to an expanded diameter. Elements of this type are generally referred to herein as "non-deforming elements." Accordingly, the term "non-deforming element" is intended to generally describe a structure that substantially maintains its original dimensions (i.e., length and width) during deployment of the stent. Each radial element is preferably formed as a flat sheet that is cut or otherwise shaped to provide a slide-and-lock mechanism.

The term "radial strength," as used herein, describes the external pressure that a stent is able to withstand without incurring clinically significant damage. Due to their high radial strength, balloon expandable stents are commonly used in the coronary arteries to ensure patency of the vessel. During deployment in a body lumen, the inflation of the balloon can be regulated for expanding the stent to a particular desired diameter. Accordingly, balloon expandable stents may be used in applications wherein precise placement and sizing are important. Balloon expandable stents may be used for direct stenting applications, where there is no pre-dilation of the vessel before stent deployment, or in prosthetic applications, following a pre-dilation procedure (e.g., balloon angioplasty). During direct stenting, the expansion of the inflatable balloon dilates the vessel while also expanding the stent.

In another preferred embodiment, the stent further comprises a tubular member formed from a biocompatible and preferably, bioresorbable polymer, such as those disclosed in co-pending U.S. application Ser. No. 10/952,202; incorporated herein in its entirety by reference. It is also understood that the various polymer formulae employed may include homopolymers and heteropolymers, which includes stereoisomers. Homopolymer is used herein to designate a polymer comprised of all the same type of monomers. Heteropolymer is used herein to designate a polymer comprised of two or more different types of monomer which is also called a co-polymer. A heteropolymer or co-polymer may be of a kind known as block, random and alternating. Further with respect to the presentation of the various polymer formulae, products according to embodiments of the present invention may be comprised of a homopolymer, heteropolymer and/or a blend of such polymers.

The term "bioresorbable" is used herein to designate polymers that undergo biodegradation (through the action of water and/or enzymes to be chemically degraded) and at least some of the degradation products are eliminated and/or absorbed by the body. The term "radiopaque" is used herein to designate an object or material comprising the object visible by in vivo analysis techniques for imaging such as, but not limited to, methods such as x-ray radiography, fluoroscopy, other forms of radiation, MRI, electromagnetic energy, structural imaging (such as computed or computerized tomography), and functional imaging (such as ultrasonography). The term, "inherently radiopaque", is used herein to designate polymer that is intrinsically radiopaque due to the covalent bonding of halogen species to the polymer. Accordingly, the term does encompass a polymer which is simply blended with a halogenated species or other radiopacifying agents such as metals and their complexes.

In another preferred variation, the stent further comprises an amount of a therapeutic agent (for example, a pharmaceutical agent and/or a biologic agent) sufficient to exert a selected therapeutic effect. The term "pharmaceutical agent", as used herein, encompasses a substance intended for mitigation, treatment, or prevention of disease that stimulates a specific physiologic (metabolic) response. The term "biological agent", as used herein, encompasses any substance that possesses structural and/or functional activity in a biological system, including without limitation, organ, tissue or cell based derivatives, cells, viruses, vectors, nucleic acids (animal, plant, microbial, and viral) that are natural and recombinant and synthetic in origin and of any sequence and size, antibodies, polynucleotides, oligonucleotides, cDNA's, oncogenes, proteins, peptides, amino acids, lipoproteins, glycoproteins, lipids, carbohydrates, polysaccharides, lipids, liposomes, or other cellular components or organelles for instance receptors and ligands. Further the term "biological agent", as used herein, includes virus, serum, toxin, antitoxin, vaccine, blood, blood component or derivative, allergenic product, or analogous product, or arsphenamine or its derivatives (or any trivalent organic arsenic compound) applicable to the prevention, treatment, or cure of diseases or injuries of man (per Section 351(a) of the Public Health Service Act (42 U.S.C. 262(a)). Further the term "biological agent" may include 1) "biomolecule", as used herein, encompassing a biologically active peptide, protein, carbohydrate, vitamin, lipid, or nucleic acid produced by and purified from naturally occurring or recombinant organisms, tissues or cell lines or synthetic analogs of such molecules, including antibodies, growth factors, interleukins and interferons; 2) "genetic material" as used herein, encompassing nucleic acid (either deoxyribonucleic acid (DNA) or ribonucleic acid (RNA), genetic element, gene, factor, allele, operon, structural gene, regulator gene, operator gene, gene complement, genome, genetic code, codon, anticodon, messenger RNA (mRNA), transfer RNA (tRNA), ribosomal extrachromosomal genetic element, plasmagene, plasmid, transposon, gene mutation, gene sequence, exon, intron, and, 3) "processed biologics", as used herein, such as cells, tissues or organs that have undergone manipulation. The therapeutic agent may also include vitamin or mineral substances or other natural elements.

In some embodiments, the design features of the radial elements can be varied to customize the functional features of strength, compliance, radius of curvature at deployment and expansion ratio. In some embodiments, the stent comprises a resorbable material and vanishes when its job is done. In some embodiments, the stent serves as a therapeutic delivery platform.

The stent preferably comprises at least one longitudinal module, which consists of a series of radial elements, including one or more slide-and-lock radial elements and optionally one or more passive radial elements, linked in the longitudinal axis by flexible coupling portions. Preferably, the radial elements from two or more similar longitudinal modules are slidably connected to circumferentially adjacent radial elements. Of course, single module (or jellyroll-type) embodiments are also encompassed within the scope of the present disclosure. Each module is preferably a discrete, unitary structure that does not stretch or otherwise exhibit any substantial permanent deformation during stent deployment.

Some embodiments relate to a radially expandable stent used to open, or to expand a targeted area in a body lumen. In some embodiments, the assembled stent comprises a tubular member having a length in the longitudinal axis and a diameter in the circumferential or radial axis, of appropriate size to be inserted into the body lumen. The length and diameter of the tubular member may vary considerably for deployment in different selected target lumens depending on the number and configuration of the structural components, described below. The tubular member is adjustable from at least a first collapsed diameter to at least a second expanded diameter. One or more stops and engaging elements or tabs are incorporated into the structural components of the tubular member whereby recoil (i.e., collapse from an expanded diameter to a more collapsed diameter) is minimized to less than about 5%.

The tubular member in accordance with some embodiments has a "clear through-lumen," which is defined as having no structural elements protruding into the lumen in either the collapsed or expanded diameters. Further, the tubular member has smooth marginal edges to minimize the trauma of edge effects. The tubular member is preferably thin-walled (wall thickness depending on the selected materials ranging from less than about 0.010 inches for plastic and degradable materials to less than about 0.002 inches for metal materials) and flexible (e.g., less than about 0.01 Newtons force/millimeter deflection) to facilitate delivery to small vessels and through tortuous vasculature.

Stents according to aspects of the present invention are preferably formed with walls for providing a low crossing profile and for allowing excellent longitudinal flexibility. In preferred embodiments, the wall thickness is about 0.0001 inches to about 0.0250 inches, and more preferably about 0.0010 to about 0.0100 inches. However, the wall thickness depends, at least in part, on the selected material. For example, the thickness may be less than about 0.0060 inches for plastic and degradable materials and may be less than about 0.0020 inches for metal materials. More particularly, for a 3.00 mm stent application, when a plastic material is used, the thickness is preferably in the range of about 0.0040 inches to about 0.0045 inches. However, a stent having various diameters may employ different thicknesses for biliary and other peripheral vascular applications. The above thickness ranges have been found to provide preferred characteristics through all aspects of the device including assembly and deployment. However, it will be appreciated that the above thickness ranges should not be limiting with respect to the scope of the invention and that the teachings of the present invention may be applied to devices having dimensions not discussed herein.

Some aspects of embodiments of stents are disclosed in U.S. Pat. Nos. 6,033,436, 6,224,626 and 6,623,521; each of which is hereby incorporated in its entirety by reference thereto. Some aspects are also disclosed in co-pending U.S. Patent Application Nos. 60/601,526, 10/655,338, 10/773,756, 10/897,235; each of which is incorporated herein in its entirety by reference thereto.

Embodiments and Design Features of the Vascular Prosthesis

Preferred embodiments of a vascular prosthesis device or stent are disclosed herein. These embodiments teach unique design attributes and features that can be used in conjunction with a wide range of vascular prostheses or stents including embodiments of stents disclosed, taught or suggested herein, and/or prior art stents.

Preferred embodiments and additional design attributes and features allow for further improvement and optimization in vascular prosthesis devices or stents. The embodiments disclose novel geometries and mechanisms for vascular prosthesis devices or stents. These embodiments and attributes can be utilized individually or in combination to achieve desired optimum device performance and characteristics. Attributes of these embodiments are not limited to a particular material. Devices or attributes may be prepared from a variety of materials, including but not limited to, metals and polymers, including layers thereof, or any combination thereof, and any of the materials or combinations thereof disclosed, taught or suggested herein.

As used herein, one or more radial elements linked to one another in the longitudinal axis forms a module. The slidable interlocking of one or more modules in the circumferential axis forms a stent or vascular prosthesis. The stent is expandable via a sliding or articulating mechanism to allow variation in the stent diameter. The number of radial elements in a module and the number of modules comprising the stent can be efficaciously varied to provide for customization in the stent design and enhanced design versatility. Because longitudinally adjacent radial elements within a module are pre-linked (e.g., cut out of a single piece of material) in some preferred embodiments disclosed herein, there is no need to weld and/or otherwise connect the radial elements within a module. Likewise, radial elements from circumferentially adjacent modules are preferably interlinked (e.g., via insertion of tabs or rails within slots) during assembly without any welding and/or other fixed connections.

As detailed herein, various methods and techniques may be used to fabricate or manufacture the stents of embodiments of the invention. These include injection molding, laser machining, laser cutting, laser ablation, die-cutting, chemical etching, plasma etching or other methods known in the art which are capable of producing high-resolution components. In some embodiments, the stent is fabricated from a biodegradable material.

The stents and prostheses of embodiments of the invention can have many applications and can be utilized in various techniques and in combination with other procedures, some of which are disclosed herein. One use of the stents is coronary stenting applications. The stenting can be performed in conjunction with other catheter-based procedures, such as balloon angioplasty or artherectomy. The stents typically allow for an excellent final result to be obtained with little to no narrowing remaining within the coronary arteries. By performing a stent insertion along with other procedures, such as balloon angioplasty or artherectomy, the risk of the artery re-closing (restenosis) is greatly reduced.

Various polymer materials may be used in conjunction with the stents, as described herein such as in the sections "Polymeric Stents" and "Differential Layered and Spatially Localized Vascular Prosthesis." Various therapeutic agents may also be incorporated into the stents as described as in these sections.

If desired for a particular application, embodiments of the present invention may be used with a delivery sheath to constrain the stent in the collapsed condition and to protect the inner wall of the vessel during stent delivery. For example, a retractable delivery sheath may be configured for enclosing the stent during delivery. After the treatment site is reached, the sheath is withdrawn to expose the stent.

In an alternative configuration, the stents may be used in combination with a covering or sheath to provide a vessel graft. Different regions of the stent may exhibit different expanded diameter, and the actual number and dimensions of the radial elements may vary. The locking mechanism may also be releasable.

It will be appreciated by those skilled in the art that the basic design of a series of slide-and-lock radial elements provides the manufacturer with a great deal of flexibility with regard to the collapsed and expanded diameters of the stent as well as the longitudinal length. Increased expanded diameter and expansion ratio can be achieved by increasing the number of modules, e.g., the number of slidably interconnected radial elements that comprise the circumference of the tubular member. Increased longitudinal length can be achieved by increasing the number of radial elements within a module.

In another variation of the embodiments of the stent, different regions within the stent may exhibit different expanded diameters, such that the stent may be adjustable to different luminal states along the length of the stent. Accordingly, the stent may exhibit a tapered configuration in its deployed state, having a larger diameter at one end with progressive or stepwise decreases in expanded diameter moving toward the other end of the stent.

It will be appreciated by those of skill in the art that the interlocking and sliding radial element design of embodiments of the invention provides the manufacturer with substantial flexibility in customizing the stent for different applications. Because overlap of stent components is minimized by the nesting frame elements, the collapsed profile can be very thin without compromising radial strength. Moreover, the degree of overlap does not change substantially during expansion, unlike jelly-roll designs which expand by unraveling of a rolled sheet. Furthermore, the deployment flexibility of the stent of embodiments of the invention can be customized by changing the length, configuration and number of radial elements employed. Thus, a very flexible and ultra-thin embodiment of the stent is deemed to be uniquely suited for deployment in small and difficult to reach vessels, such as the intercranial vessels distal to the carotids and the remote coronary vessels.

The construction of the stent in this fashion provides a great deal of benefit over the prior art. The construction of the locking mechanism is largely material-independent. This allows the structure of the stent to comprise high strength materials, not possible with designs that require deformation of the material to complete the locking mechanism. The incorporation of these materials will allow the thickness required of the material to decrease, while retaining the strength characteristics of thicker stents. In preferred embodiments, the frequency and arrangement of locking holes, stops or teeth present on selected elements prevents unnecessary recoil of the stent subsequent to expansion.

In any of the embodiments taught or suggested herein, materials may be used that exhibit clinical visibility (radiopacity), e.g., by incorporation of iodine or bromine or other radiopaque elements, use of iodine-containing or other contrast agents. Materials may be non-resorbable polymers or radiopaque constituents of metal particulates, bands or even liquid gold. Methods for viewing may include, but are not limited to, x-ray, fluoroscopy, ultrasound, MRI, or Imatron Electron Beam Tomography (EBT).

Non-Actuating Slide-and-lock Device Design

Figure 2:
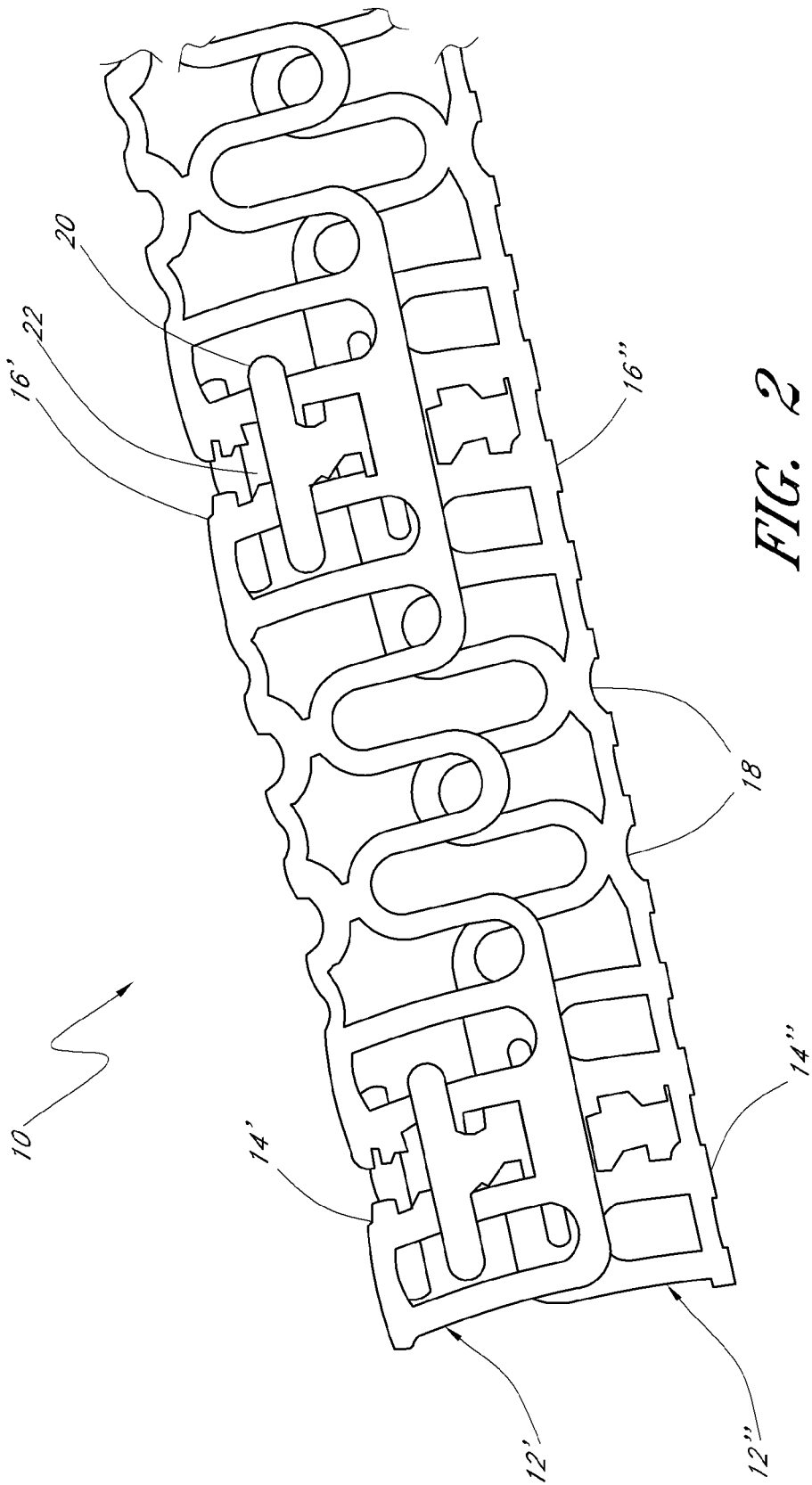
FIG. 2 is a perspective partial view of the stent of FIG. 1 in a more expanded state.
Figure 3:
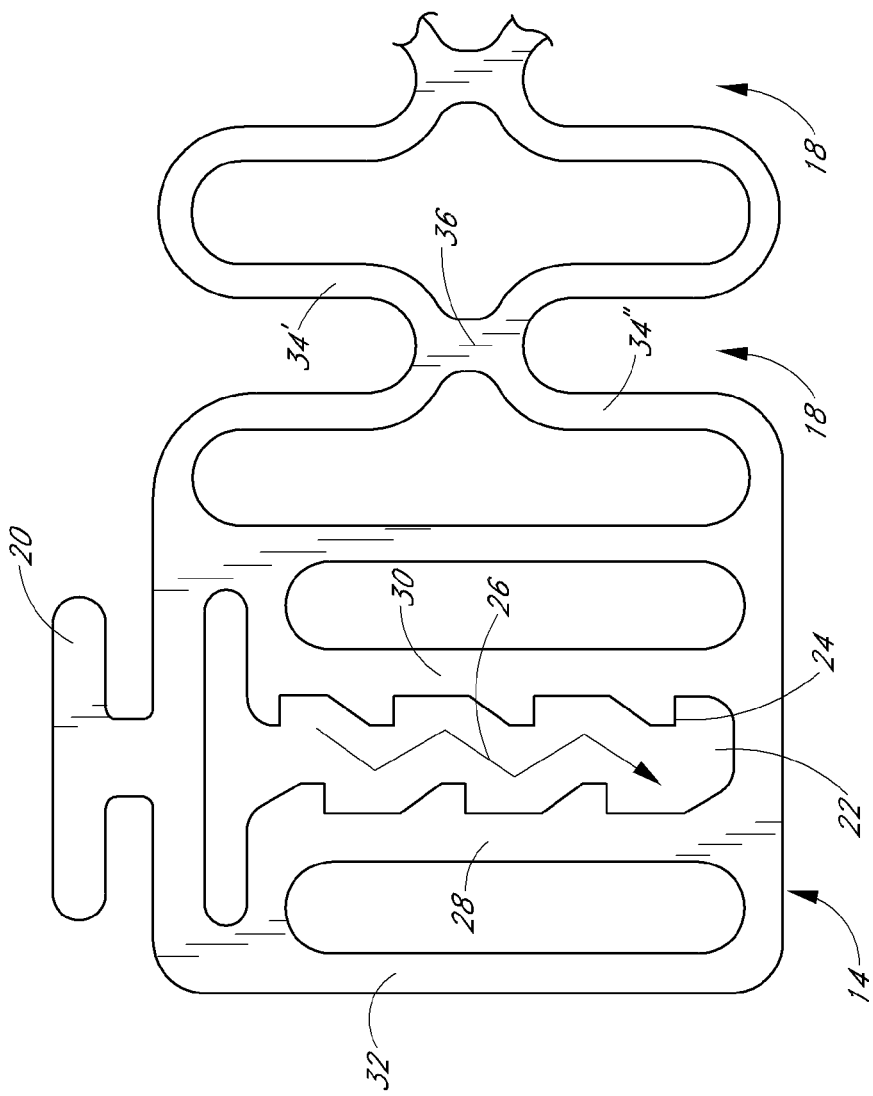
FIG. 3 is an enlarged planar view of a radial element of the stent of FIG. 1 illustrating a path of travel during deployment.

FIGS. 1-3 show partial views of a slide-and-lock stent or vascular prosthesis device 10 in accordance with one embodiment of the present invention. FIG. 1 shows the stent 10 in a partially-expanded state and FIG. 2 shows the stent 10 in an expanded state.

The embodiment illustrated in FIGS. 1-3 is a slide-and-lock stent device 10 that employs no actuating (that is, flexing, bending, and the like) elements to achieve expansion and lockout.

FIGS. 1 and 2 show partial views of two circumferentially adjacent modules 12' and 12", each having longitudinally offset slide-and-lock radial elements, 14' and 16' in module 12', and 14" and 16" in module 12". Modules generally have at least two (2) slide-and-lock radial elements, at proximal and distal ends of the module. These are sometimes referred to as mechanism radial elements, because they comprise the slide-and-lock mechanisms that provide controlled deployment and resist radial compression. In preferred embodiments of these modules, there are between 2 and 8 slide-and-lock radial elements, and more preferably, between 2 and 4 slide-and-lock radial elements per module.

In some embodiments, such as that illustrated in FIGS. 1-3, the longitudinally offset slide-and-lock radial elements within a module are separated and interconnected by one or more passive radial elements, such as the two (2) passive radial elements 18 shown in FIGS. 1 and 2. These passive radial elements are sometimes referred to as non-mechanism radial elements because they do not contribute to the slide-and-lock mechanism of radial expansion, like the slide-and-lock radial elements. In some embodiments, there are no passive radial elements. In other embodiments, there are from 1 to 8 passive radial elements disposed between each slide-and-lock radial element. More preferably, there are from 1 to 4 passive radial elements disposed between each slide-and-lock radial element in a module. As disclosed in greater detail below, these passive, non-mechanism radial elements can be engineered in many different geometric configurations to provide inter alia variable flexibility, variable radial strength, variable scaffolding (vessel wall coverage), and/or a safety catch to prevent over-expansion.

As can be seen in FIGS. 1 and 2, a tab 20 on each slide-and-lock radial element (shown here on 16") is slidably engaged within a slot 22 in the circumferentially adjacent slide-and-lock radial element (shown here in 16'). The entire circumference of stent 10 may comprise from 1 to 8 circumferentially adjacent modules, more preferably from 2 to 6 circumferentially adjacent radial elements, and most preferably from 2 to 4 circumferentially adjacent radial elements.

As best seen in FIG. 3, a slide-and-lock radial element 14 has a slot 22 with lockout teeth, catches or stops 24. When a tab 20 is slidably engaged within a slot 22 from a circumferentially adjacent slide-and-lock radial element, it can travel within the slot 22—thereby traveling through a defined travel path, as generally indicated by arrow 26 in FIG. 3. The travel path may be disposed substantially in the circumferential axis as shown, or in some embodiments, the travel path may traverse both circumferential and longitudinal axes. Advantageously, the slot 22, stop 24, and tab 20 configurations allow for expansion that achieves radial expansion while restricting travel in the opposite direction. Defined path geometry can easily be altered to achieve a variety of device performance attributes, for example, lower/higher deployment pressures and the like, among others.

In the illustrated embodiment of the slot 22 shown in FIG. 3, the stops 24 are circumferentially offset from one another and disposed on alternating proximal 28 and distal 30 sides or walls of the slot. Further, the illustrated catches 24 are configured so as to allow the tab 20 to slide past each stop, translating simultaneously in the longitudinal (axial) and circumferential (radial) axes, while moving along the travel path 26. However, the stop 24 is configured to prevent the tab 20 from moving backwards along the travel path 26. The slide-and-lock mechanism illustrated in FIGS. 1-3 does not involve material bending or deformation of the stent materials. Of course, other slot 22, stop 24, and tab 20 configurations are encompassed within preferred embodiments of the invention, as long as they facilitate one-way sliding of the tab 20 within the slot 22. Further examples of different slot and stop configurations are disclosed with reference to FIGS. 4-16. The configurations disclosed herein are generally designed to allow one-way sliding to a more expanded circumference, while preventing significant recoil.

In the illustrated embodiment (FIGS. 1-3), there are also frame elements 32 (shown in FIG. 3), which surround the radial element 14. In some preferred embodiments, there are no frame elements. In others, as shown, the frame elements may be used to provide additional scaffolding and/or radial strength.

Figure 13:
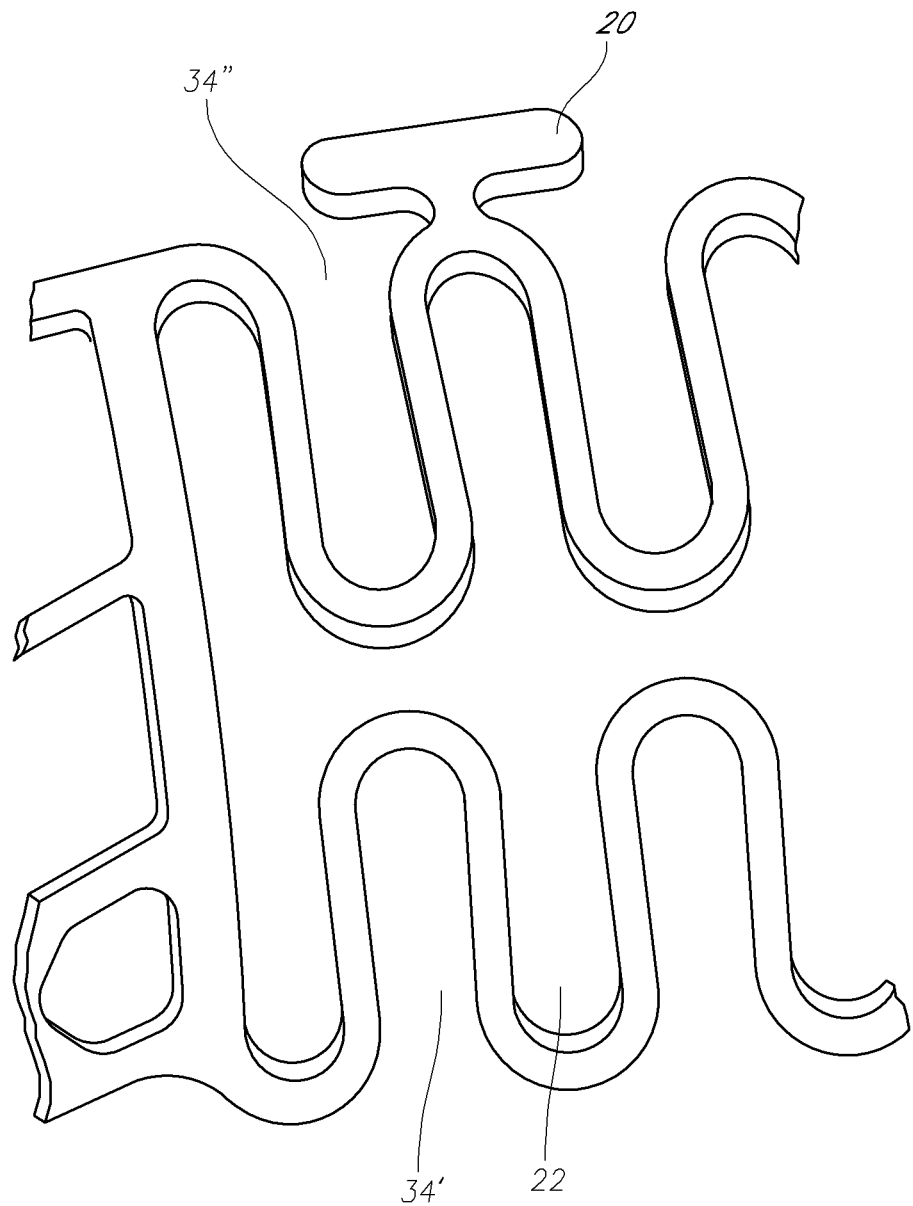
FIG. 13 is a perspective partial view of a slide-and-lock stent incorporating intra-modular flexible elements having features and advantages in accordance with one embodiment of the invention.
Figure 14:
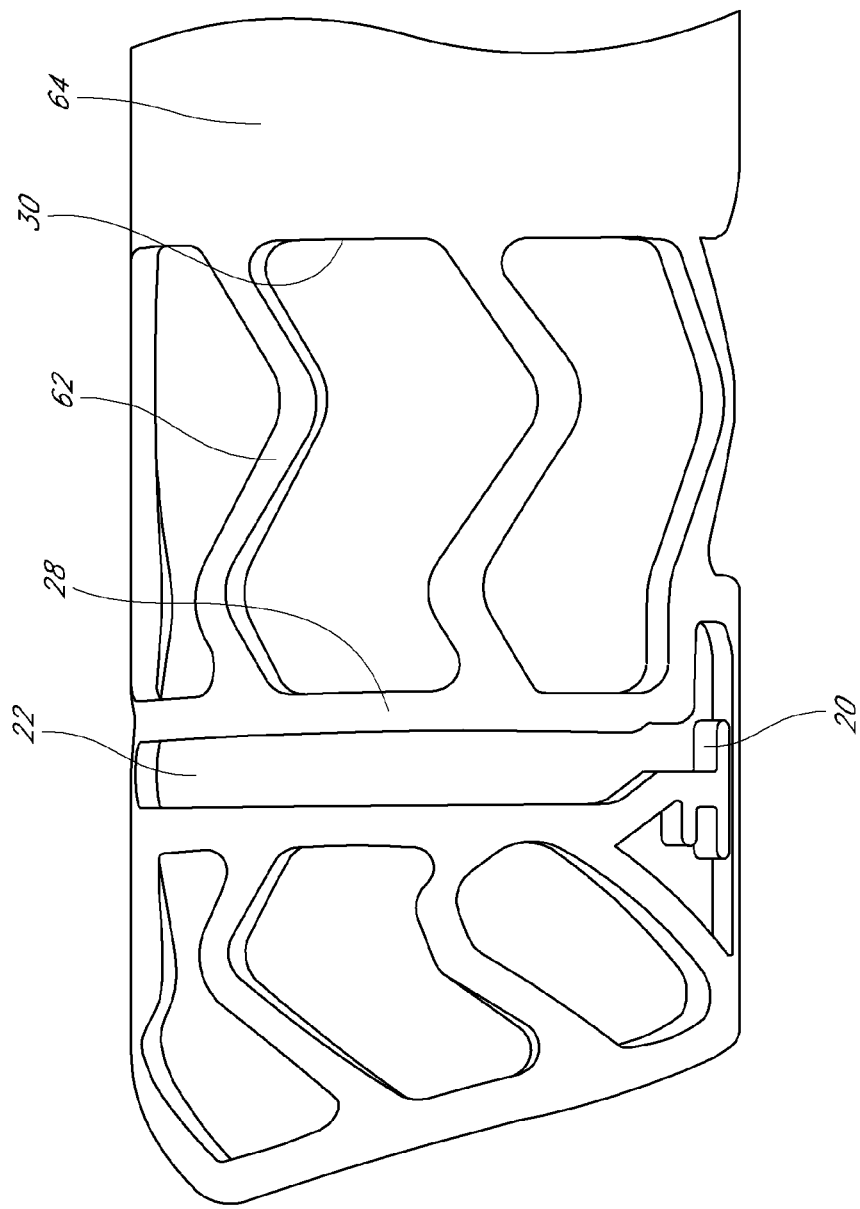
FIG. 14 is a perspective partial view of a slide-and-lock stent incorporating intra-modular flexible elements having features and advantages in accordance with another embodiment of the invention.

The passive radial elements 18 illustrated in FIG. 3 comprise U-shaped members 34' and 34", which are inverted with respect to one another. The apices of the inverted U-shaped members are connected to one another by a linkage element 36. The configurations of the passive radial elements may vary greatly depending on the desired stent attributes. For example, the inverted U-shaped members 34' and 34" and the linkage element 36 of a passive radial element may be aligned within the module in a direction substantially parallel to the circumferential axis (as shown in FIGS. 1-3). Alternatively, the inverted U-shaped members 34' and 34" and the linkage element 36 of a passive radial element may be aligned within the module in a direction which is diagonal to the circumferential axis (as shown for example in FIGS. 4-6). In other variations, the linkage element 36 which connects the apices of inverted U-shaped members 34' and 34" may be short (as shown in FIG. 3) or relatively much longer (as shown for example in FIGS. 6-7). The linkage element 36 may also be configured to enhance flexibility, e.g., in a serpentine or spring-shape. In some preferred embodiments, the passive radial elements may not include U-shaped members at all. Instead, a variety of passive, non-mechanism radial element configurations may be employed between slide-and-lock radial elements. Some examples are shown in FIGS. 13 and 14.

In preferred embodiments, each module is formed from a single piece of material—thereby avoiding any welding or other connections between longitudinally adjacent mechanism and non-mechanism radial elements. Alternatively, the slide-and-lock and passive radial elements within a longitudinal module may be attached to one another by a weldless connection, e.g., adhesive. Welded connections are also encompassed within the present disclosure. Further details of the stent construction are provided below in the Sections entitled "Metal Stents," "Polymeric Stents" and "Methods of Manufacturing and Assembling Polymeric Stents."

Figure 4:
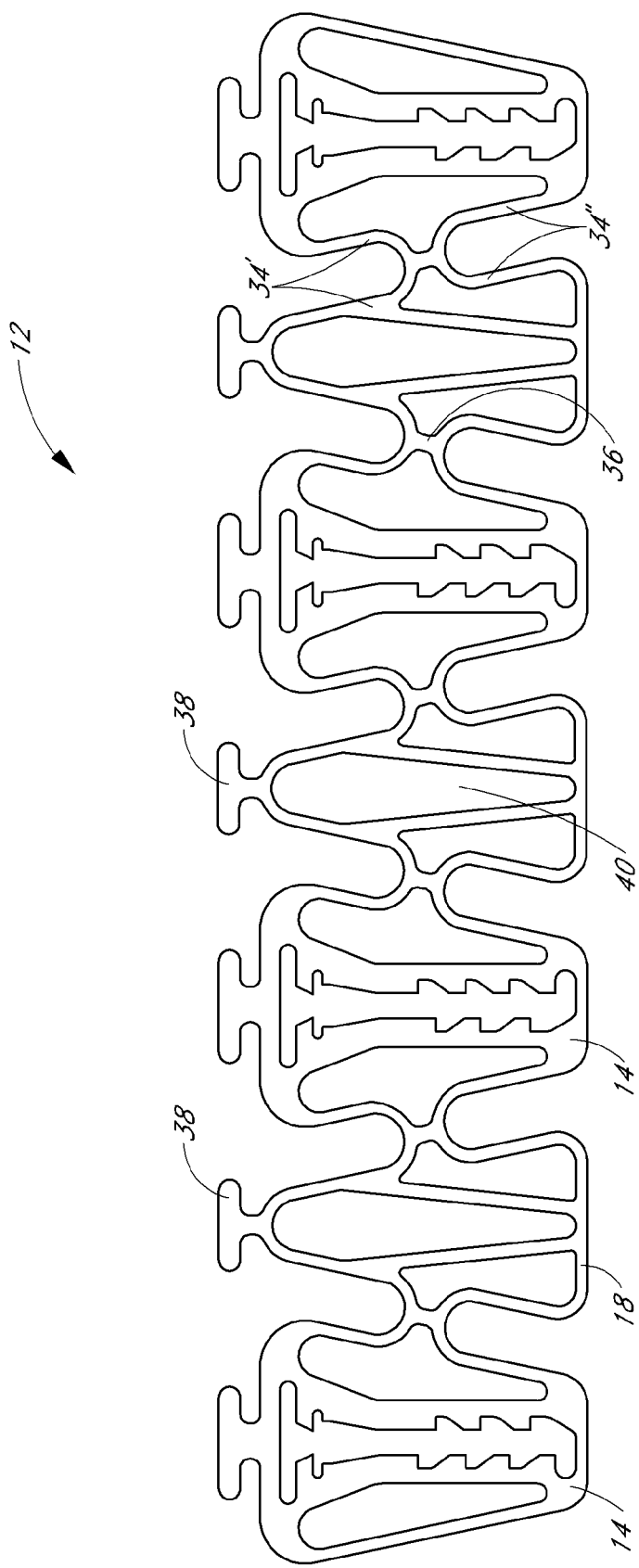
FIG. 4 is a planar partial view of a module in accordance with one preferred embodiment of a slide-and-lock stent, having passive radial elements with safety catches disposed in the longitudinal axis between each slide-and-lock radial element.
Figure 5:
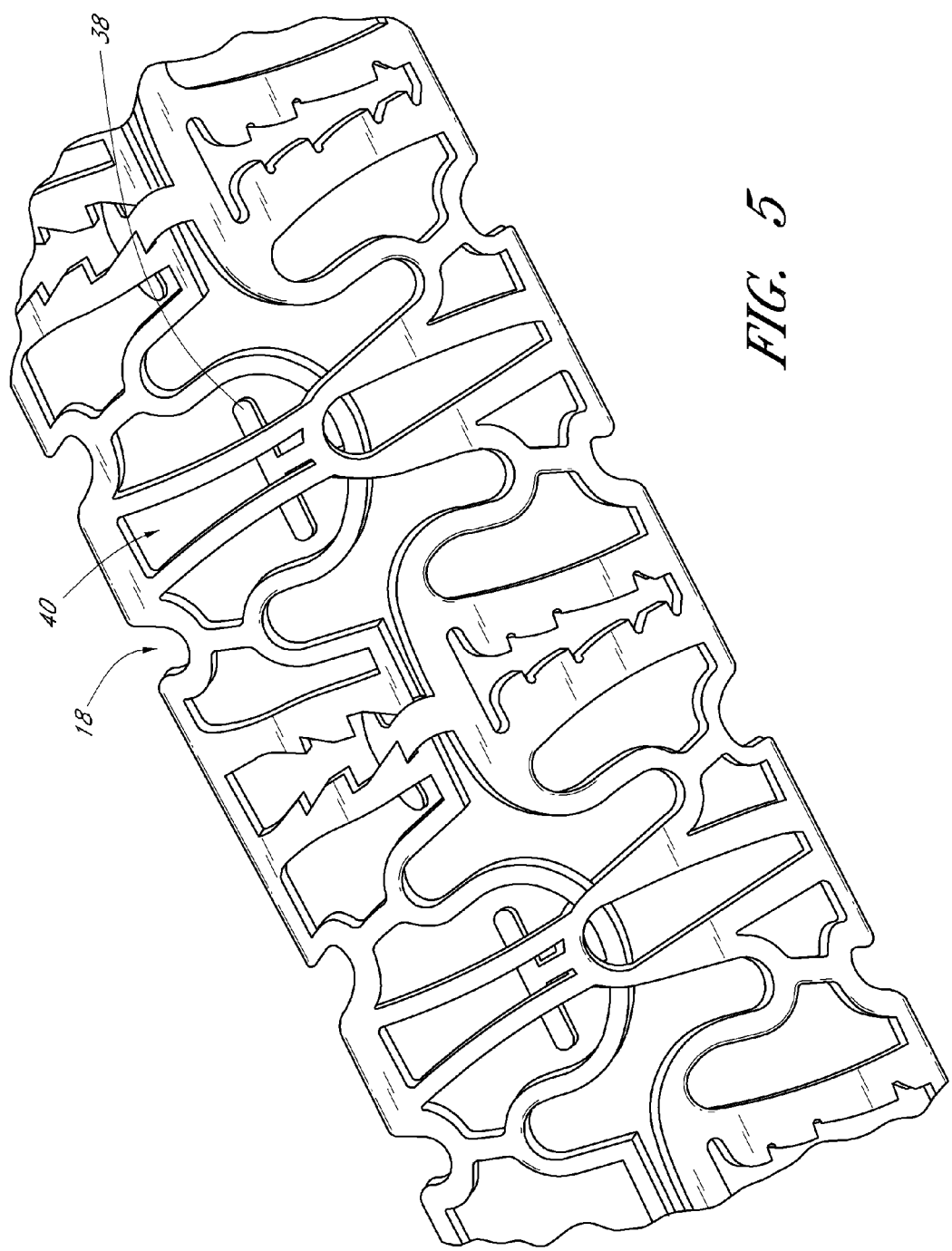
FIG. 5 is a perspective partial view of a stent comprising the modules of FIG. 4, illustrating the operation of a safety catch mechanism.

FIG. 4 shows a longitudinal module 12 of a slide-and-lock stent or vascular prosthesis device in accordance with another preferred embodiment of the present invention. Modular device designs allow for a wide variety of combinations of mechanism and non-mechanism module components. As can be seen generally from FIG. 4, there are alternating mechanism and passive (or non-mechanism) radial elements, with one passive radial element 18 disposed between each slide-and-lock radial element 14 in the module 12; although other configurations can be substituted with efficacy as needed or desired. Where N=the number of radial elements in a module, then up to N−1 passive radial elements may be employed. More preferably, a module has at least two slide-and-lock radial elements, wherein at least N−2 passive radial elements may be used. The passive radial elements in this embodiment have safety catches or tabs 38 and slots 40, but the slots do not have any stops, teeth, catches or other lockout structures. Accordingly, as illustrated in FIG. 5, when a safety tab 38 from one passive radial element is slidably engaged in the slot 40 of a circumferentially adjacent passive radial element, there is neither resistance to expansion during deployment nor resistance to recoil; thus, the radial element is still referred to as a passive or non-mechanism radial element. However, when the safety tab 38 engaged in the slot 40 slides during deployment (radial expansion) to the end of the slot 40, it will prevent further expansion during deployment, thereby providing a safety mechanism against over-expansion. As discussed above, the passive radial elements can be designed to provide a variety of features and characteristics, including, but not limited to, providing enhanced flexibility such as with spring elements (discussed further below), deployment mechanism control elements (discussed further below), preferential side branch access locations or points, and device over-extension safety catches (as discussed with regard to the safety tabs 38 and slots 40 shown in FIGS. 4 and 5.

One important aspect of a slide-and-lock design is the sizing resolution achievable during deployment, and the amount of recoil exhibited during compressive loading. The finer the mechanism of the design, the higher the sizing resolution and the lower recoil exhibited. One embodiment of the slide-and-lock radial element that facilitates sizing resolution and recoil resistance employs staggered non-symmetric lockout geometries. FIGS. 1-5 illustrate examples of such staggered non-symmetric lockout geometry, wherein the slots 22 have stops 24 arranged in a staggered pattern, on both proximal 28 and distal 30 sides of the slot 22.

Actuating Slide-and-lock Design

Figure 6:
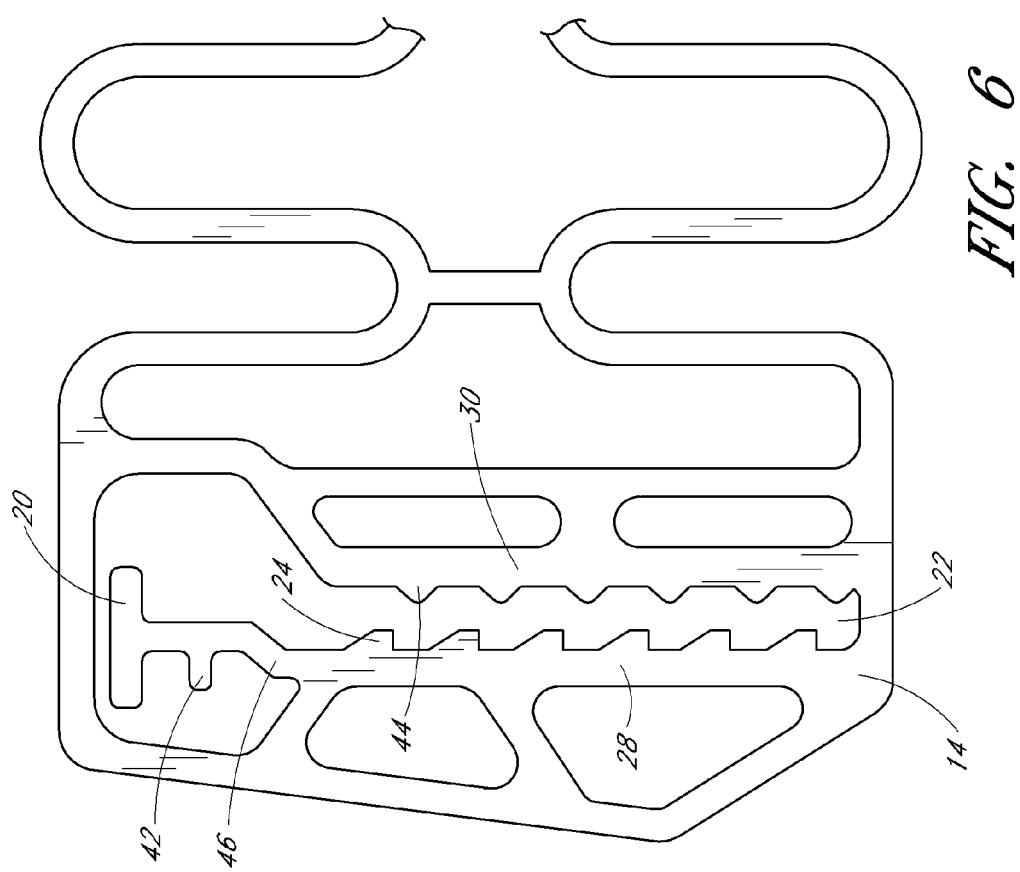
FIG. 6 is a planar partial view of a module having an actuating slide-and-lock radial element with a deflectable catch mechanism and positive return elements.
Figure 7:
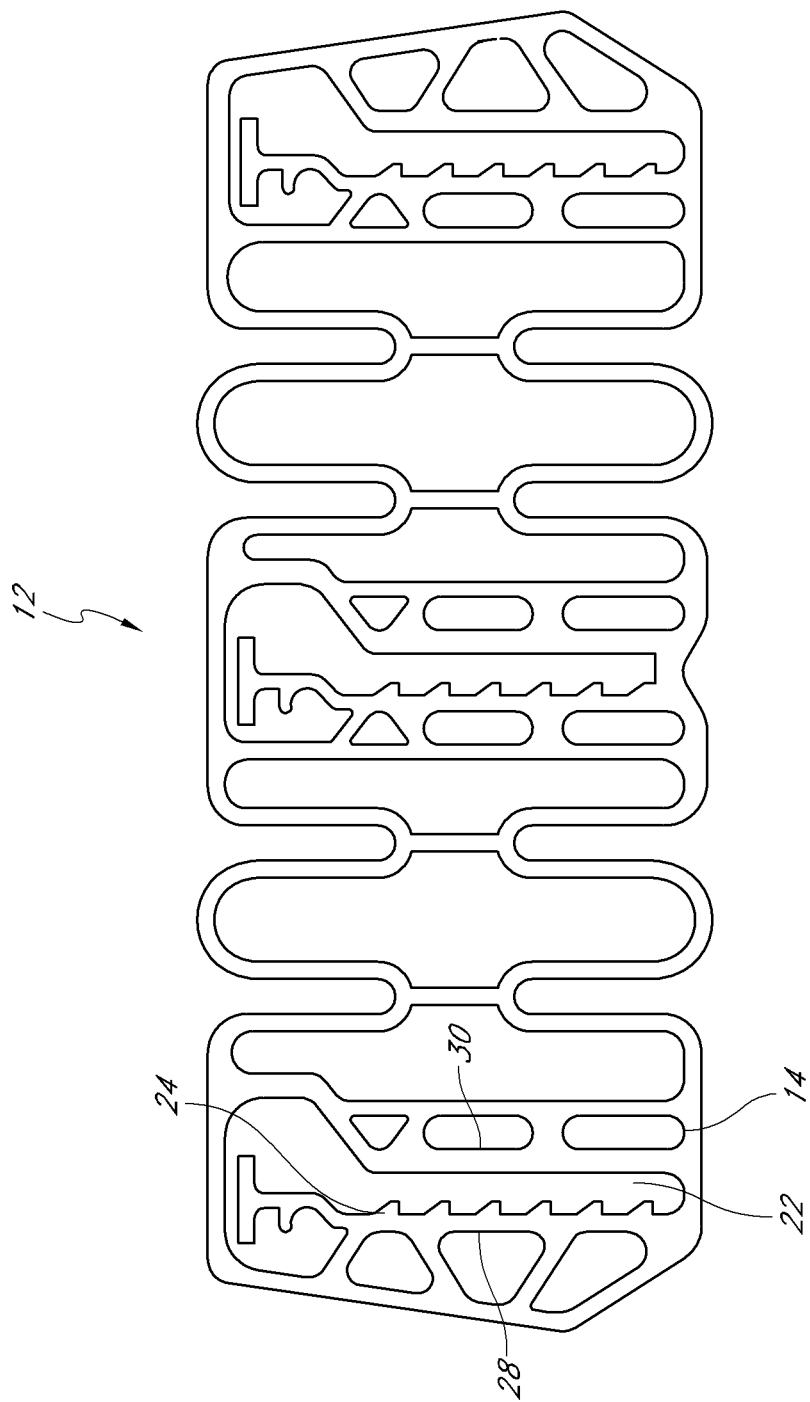
FIG. 7 is a planar view of a module having actuating slide-and-lock radial elements with deflectable catch mechanisms similar to FIG. 6, but without any positive return elements.

In an alternate embodiment, the slide-and-lock radial elements may employ different non-symmetric lockout geometry, wherein all of the stops 24 are located on only one side of the slot 22 (See e.g., FIGS. 6 and 7). Of course, those skilled in the art will appreciate that regardless of whether a staggered or one-sided stop configuration is employed, one can vary the sizing resolution by varying the number of stops and the distance between individual stops, such that as the distance between stops becomes lesser, sizing resolution increases, and as the distance between stops becomes greater, sizing resolution decreases. With reference to FIG. 6, the slide-and-lock radial element 14 has a tab 20, an actuating catch member 42, and a slot 22. All of the stops 24 are located on one side of the slot—on the proximal side 28 in the illustrated embodiment. Positive return elements 44 are located on the opposite side of the slot—on the distal side 30 in the illustrated embodiment. While the tab 20 substantially maintains travel within the radial axis, the catch member 42 is disposed along a flexible neck 46, such that as the tab 20 slides through slot 22, the interaction of the catch member 42 with the stops 24 causes the neck 46 to deflect toward the distal side 30. In the illustrated embodiment of FIG. 6, to further optimize the performance of an actuating slide-and-lock mechanism, a positive return element 44 is included into the deployment mechanism to ensure return of the deflected neck 46 and the catch member 42 to its non-actuated position. More particularly, during radial expansion, the catch mechanism, including the tab 20 and catch member 42, is first deflected distally (actuated) by the lockout stop 24. Once the catch member 42 has passed the stop 24, it can either elastically return to its natural position (discussed further below) or, as illustrated in FIG. 6, the positive return element 44 is employed to redirect the catch mechanism (tab 20 and catch member 42) to its natural, pre-actuated position within the slot 22, such that the catch member 42 catches, engages, or is otherwise prevented by its interaction with the lockout stop 24, from moving backwards to a more collapsed state (recoil).

FIG. 7 shows a module 12 employing an actuating slide-and-lock radial element 14, similar to that shown and described with reference to FIG. 6. In the illustrated embodiment of FIG. 7, all of the stops 24 are located on the proximal side 28 of the slot 22, like the embodiment shown in FIG. 6;

however, there are no positive return elements (44 in FIG. 6) located along the distal side 30 of the slot 22 in FIG. 7. Instead, in this embodiment, the catch mechanism is designed to elastically return to its natural pre-actuated position.

Figure 8:
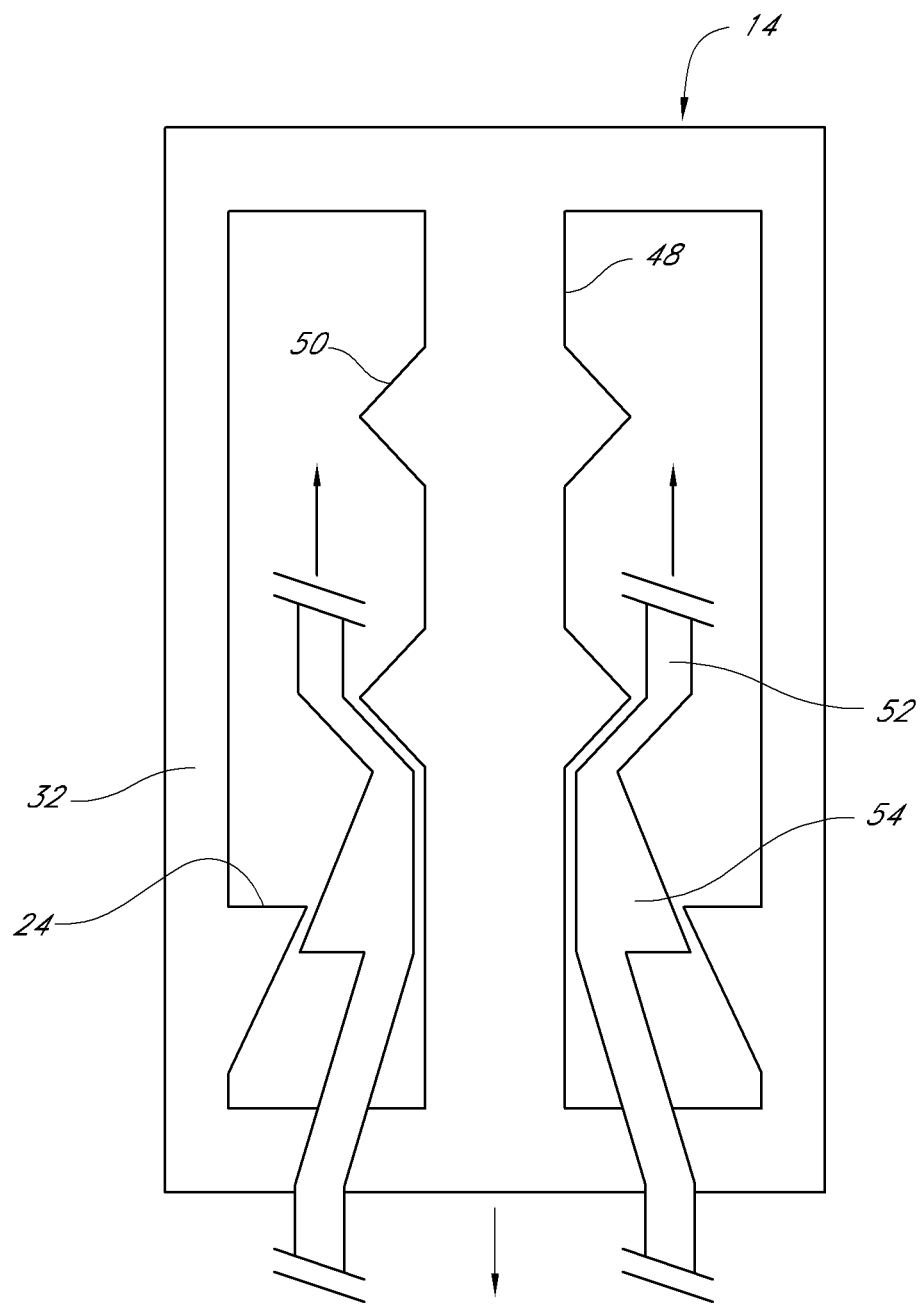
FIGS. 8 and 9 are planar partial views of an active lockout actuating slide-and-lock mechanism.
Figure 9:
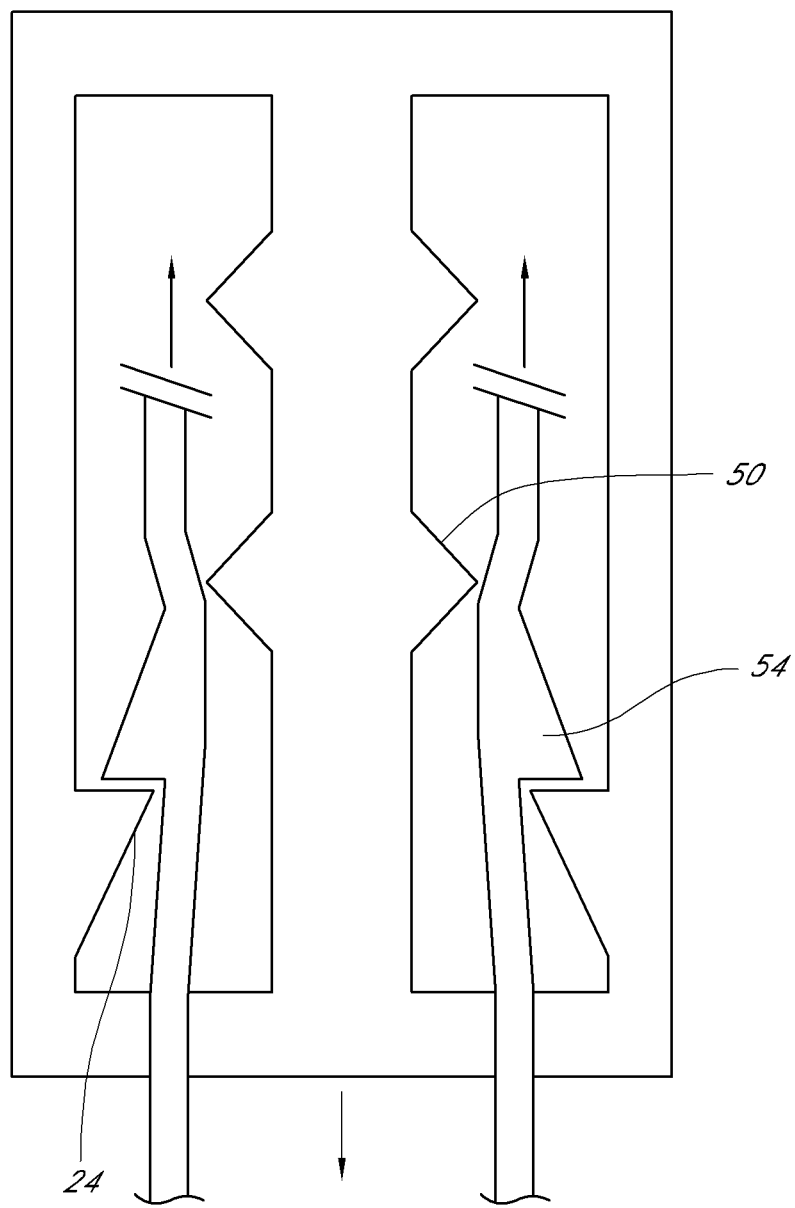

FIGS. 8 and 9 are planar partial views of an active lockout mechanism, wherein a deflectable element is actively positioned by another feature/geometry of the design to engage the lockout mechanism. Here with reference to FIGS. 8 and 9, the drawings show a partial slide-and-lock radial element 14, comprising a non-deflectable actuating rail 48 (which is centrally disposed in the illustrated embodiment), having disposed thereon an actuator 50, a plurality of which are shown symmetrically disposed along both proximal and distal surfaces of the central rail in the illustrated embodiment. Slidably engaged with the actuating rail 48 is a deflectable rail 52, comprising a deflectable catch element 54; two catch elements 54 are shown symmetrically disposed along the deflectable rail 52 in the illustrated embodiment. The actuators 50 on the actuator rail 48 and deflectable catch elements 54 on the deflectable rail 52 are configured so that as the deflectable rail 52 slides along the actuating rail 48, the actuators 50 cause the deflectable catch elements 54 to deflect outward. This active lockout mechanism also includes teeth or stops 24 (disposed along a frame element 32 in the illustrated embodiment), which are adapted to engage the deflectable catch elements 54 once actuated, thereby preventing radial recoil. FIG. 8 shows the radial element before sliding causes actuation of the active lockout mechanism. FIG. 9 shows the radial element after actuation of the active lockout mechanism, wherein the deflectable catch elements 54 are shown deflected outward by the actuators 50 and engaging the stops 24.

In variations to the illustrated embodiment, the actuators 50, deflectable catch elements 54, and stops 24, may be positioned on any of the components of the slide-and-lock radial element, as long as the actuators 50 are positioned to cause active deflection of the slidably engaged deflectable catch elements 54, such that deflection results in engagement of the stops 24 and lockout (inhibition of radial recoil).

Deformable Slide-and-lock Stent

Figure 10:
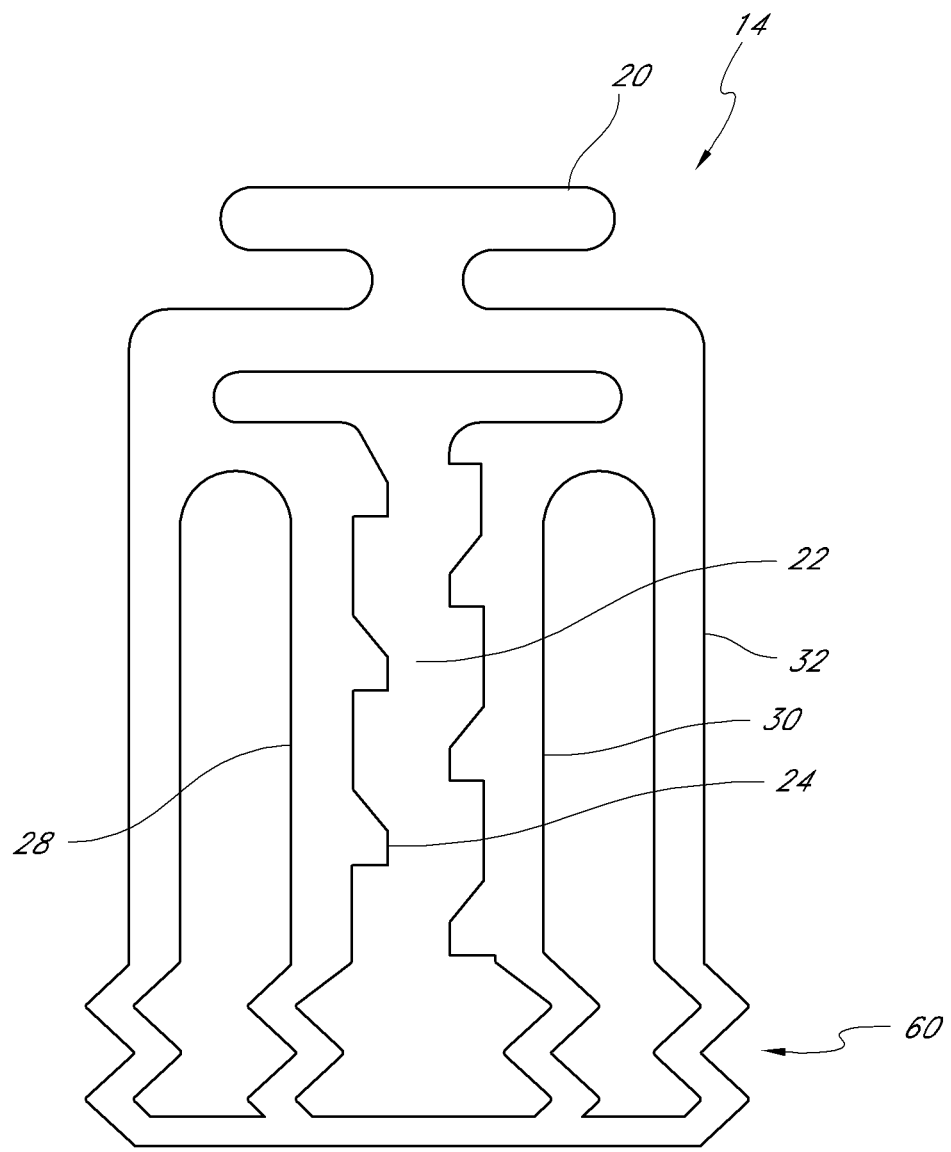
FIGS. 10 and 11 are planar partial views of a deformable slide-and-lock stent and its operation having features and advantages in accordance with one embodiment of the invention.
Figure 11:
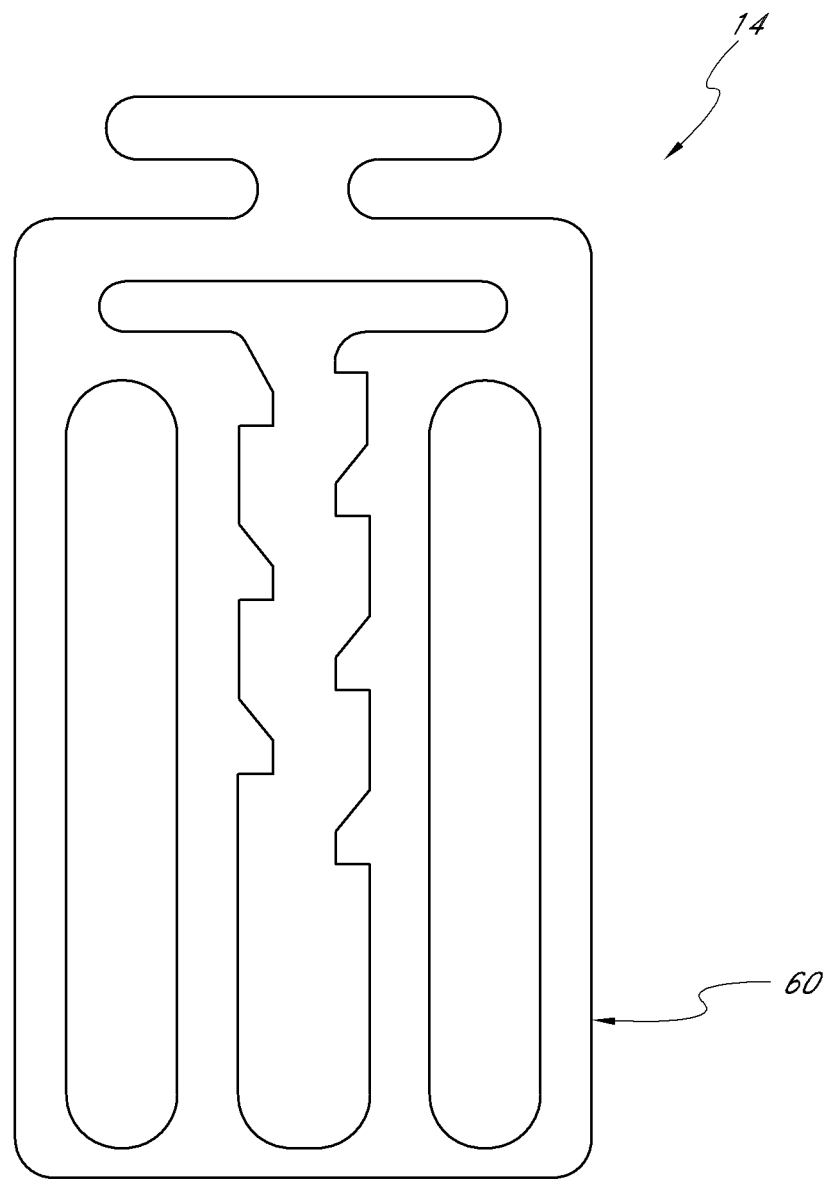

FIGS. 10 and 11 are plan views of a slide-and-lock radial element in accordance another embodiment of the present invention. The slide-and-lock radial element 14 illustrated in FIG. 10 has a tab 20, slot 22, stops or teeth 24, and a frame element 32 similar to those shown in FIG. 3. However, the slide-and-lock radial element 14 also comprises a deformable region 60. In the illustrated embodiment, the proximal and distal portions of the frame element 32 as well as the proximal 28 and distal 30 portions of the slot wall are modified in the deformable region 60 to allow expansion and/or contraction in the radial axis through material deformation. Of course, those skilled in the art will readily appreciate that a variety of material configurations, including for example, zig-zag, U-shaped, serpentine, waves, undulating, and angled configurations, as well as changes in material cross-section (e.g., from a flat sheet to a bendable wire), can be employed so as to produce regions of deformability. Lengthwise adjacent slide-and-lock and/or passive radial elements may be integral with, e.g., cut from same piece of material, or attached by a weldless connection. In some embodiments, lengthwise adjacent radial elements may be welded together.

FIG. 10 shows the radial element 14 before deformation, wherein the deformable region 60 exhibits a zig-zag configuration, and FIG. 11 shows the same radial element 14 after deformation (radial expansion), wherein the deformable region 60 is stretched out to yield a linear configuration. In the illustrated embodiment of FIGS. 10 and 11, the radial element 14 (and the stent comprising such radial element(s)) includes a deformable geometry that is incorporated into the overall stent design. The deformable regions 60 of the stent are constructed to either plastically or elastically deform during radial expansion. As the stent expands, these deformable regions can be used to achieve additional device radial expansion or increase device safety.

In one embodiment, the deformable regions plastically deform upon expansion. Advantageously, this allows for additional expansion or sizing of the stent. In another embodiment, the deformable regions elastically deform allowing for over pressurization of the stent during implantation and upon release of over pressurization, the stent returns to its intended diameter. Advantageously, this may allow for higher pressurization to treat/crack difficult lesions, while avoiding excessive vasculature injury that may occur with excessive pressure dilatations.

In yet another embodiment, the deformable regions can deform either plastically or elastically. Advantageously, this allows for an increased factor of safety as the stent reaches its maximum radial expansion limit.

Figure 12:
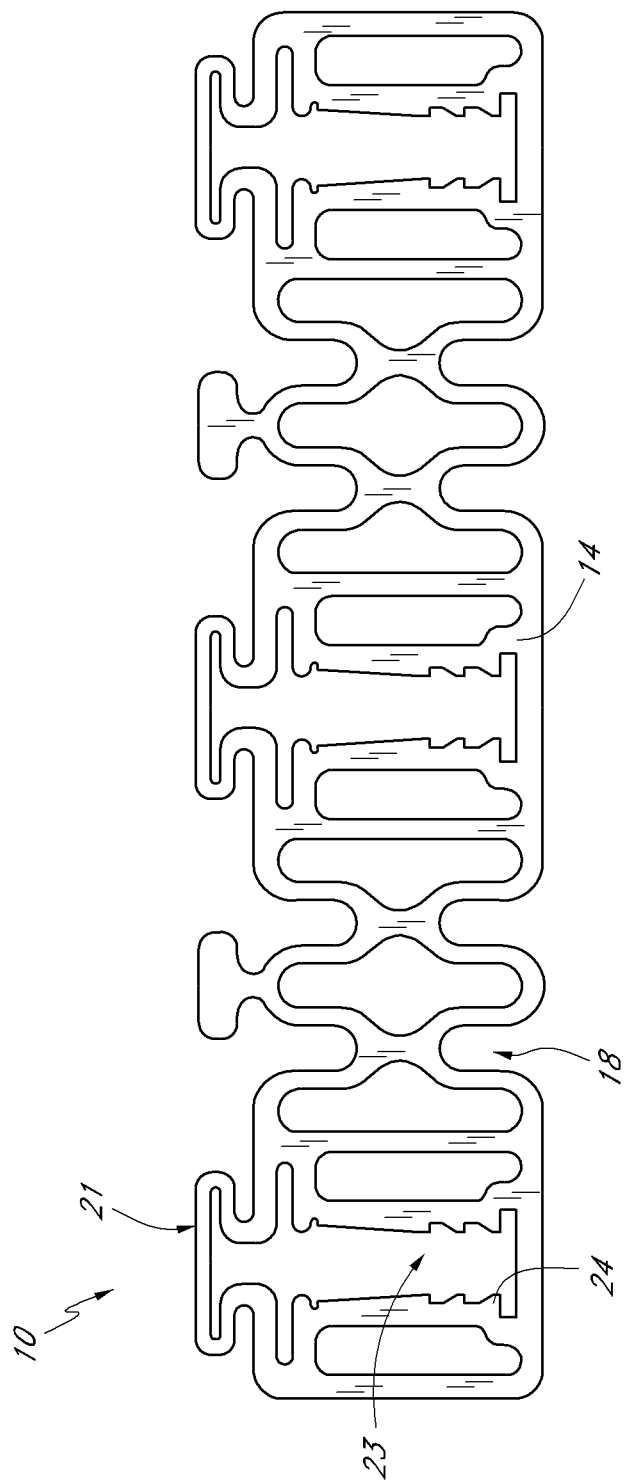
FIG. 12 is a planar view of a module of the slide-and-lock stent incorporating deformable engaging tabs in accordance with one embodiment of the invention.

FIG. 12 is a partial view of another embodiment of a deformable slide-and-lock stent 10. The drawing show a longitudinal module 12 with slide-and-lock 14 and passive 18 radial elements. Lengthwise adjacent radial elements within the module 12 are preferably attached by a weldless connection, and more preferably formed form the same piece of material. This embodiment comprises a deflectable tab 21, which is configured to allow it to deflect inwardly as it passes by the stops 24 in the slot 23 of a radially adjacent slide-and-lock radial element 14, but plastically returns to its prior form and alignment to prevent recoil.

Two Sided Lockout Features

Some embodiments utilize a two-sided lockout feature, that is, stops or teeth 24 on both sides of a slot 22 (see, for example, FIGS. 1-6). The two-sided mechanism can be employed to increase device alignment and additionally limit off center device travel. In modified embodiments, a single-sided lockout mechanism may be utilized, that is, teeth 24 on only one side of the slot 22, (see, for example, FIG. 7) as needed or desired. In another modified embodiment, a two-sided mechanism can be employed by placing stops or teeth 24 on both sides of a rib element (see, for example, FIGS. 8-9). In this embodiment, more than one safety catch elements 54 may be employed to interact with both sides of the rib element.

Elements to Enhance Flexibility of Stent Device

Embodiments of the slide-and-lock device design can incorporate elements which enable device flexibility in both the collapsed and expanded states. This is accomplished by providing flexible or spring elements that, for example, vary the geometry and location of the attachments between adjacent radial elements.

Figure 15:
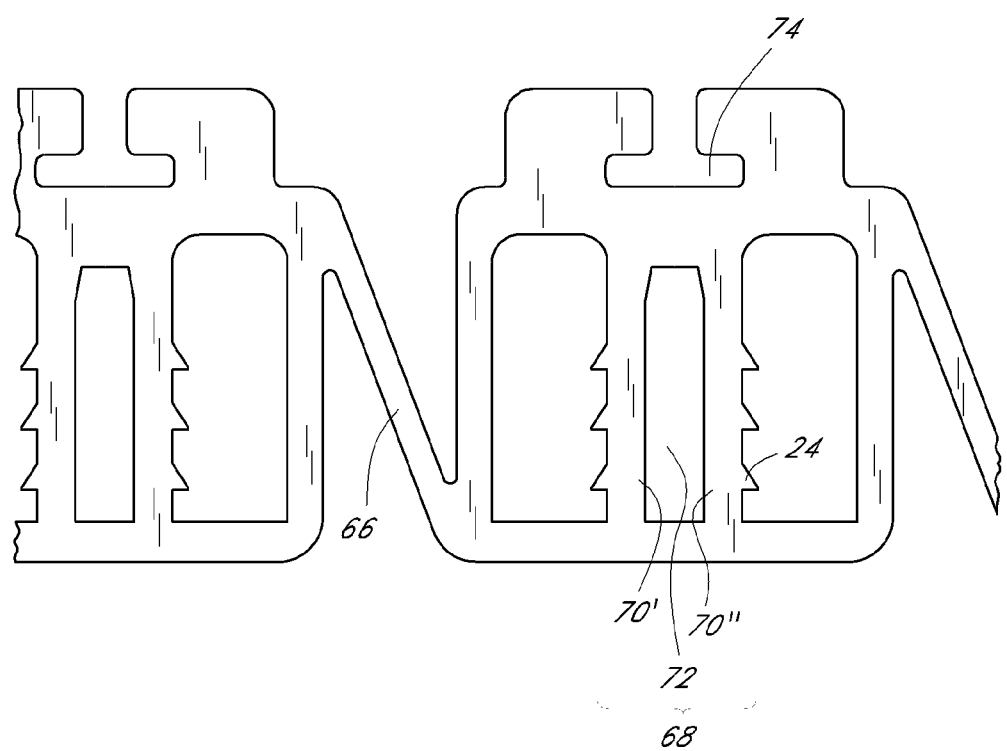
FIG. 15 is a planar partial view of a slide-and-lock stent incorporating intra-modular flexible elements and split deflectable rails having features and advantages in accordance with another embodiment of the invention.

FIG. 4, for example, shows flexible or spring elements 34' and 34" in the configuration of inverted diagonally aligned U-shaped members. With reference to FIGS. 13-15, various alternative embodiments of flexible elements are illustrated. FIG. 13 shows inverted U-shaped members 34' and 34" similar to those illustrated in FIGS. 1-3; however, the passive radial elements in FIG. 13 further comprise safety tabs 38 and non-mechanism slots 40. As detailed above with reference to FIG. 4, the inclusion of safety tabs 38 and slots 40 without locking elements (teeth, stops or catches) may provide an additional safety against over-expansion, may help to maintain slidable engagement of radially adjacent modules, and may also maintain controlled radial expansion within the radial axis. FIG. 14 shows a series of serpentine flexible elements 62 aligned in the longitudinal axis, contiguous with and abutting a slide-and-lock mechanism (with tab 20 and slot 22) on the proximal side and a circumferential band 64 on the distal side. The serpentine elements 62 may provide regions of enhanced flexibility between active slide-and-lock radial elements. FIG. 15 shows linear flexible elements 66 disposed diagonally (e.g., at an angle between the radial and longitudinal axes) between slide-and-lock radial elements. Here, the slide-and-lock radial elements illustrate a variation to the tab and slot design shown for example in FIGS. 1-3. The central rail 68 in FIG. 15 comprises proximal 70' and distal 70" rail members, each with outward facing teeth 24, and an open slot 72 disposed between the rail members. The central rail 68 is adapted to slidably engage the receiving slot 74 of a radially adjacent slide-and-lock radial element, and deflect or bow inward into the open slot 72 as the receiving slot 74 ratchets past the teeth 24.

Frangible Deployment Control Mechanism

Figure 16:
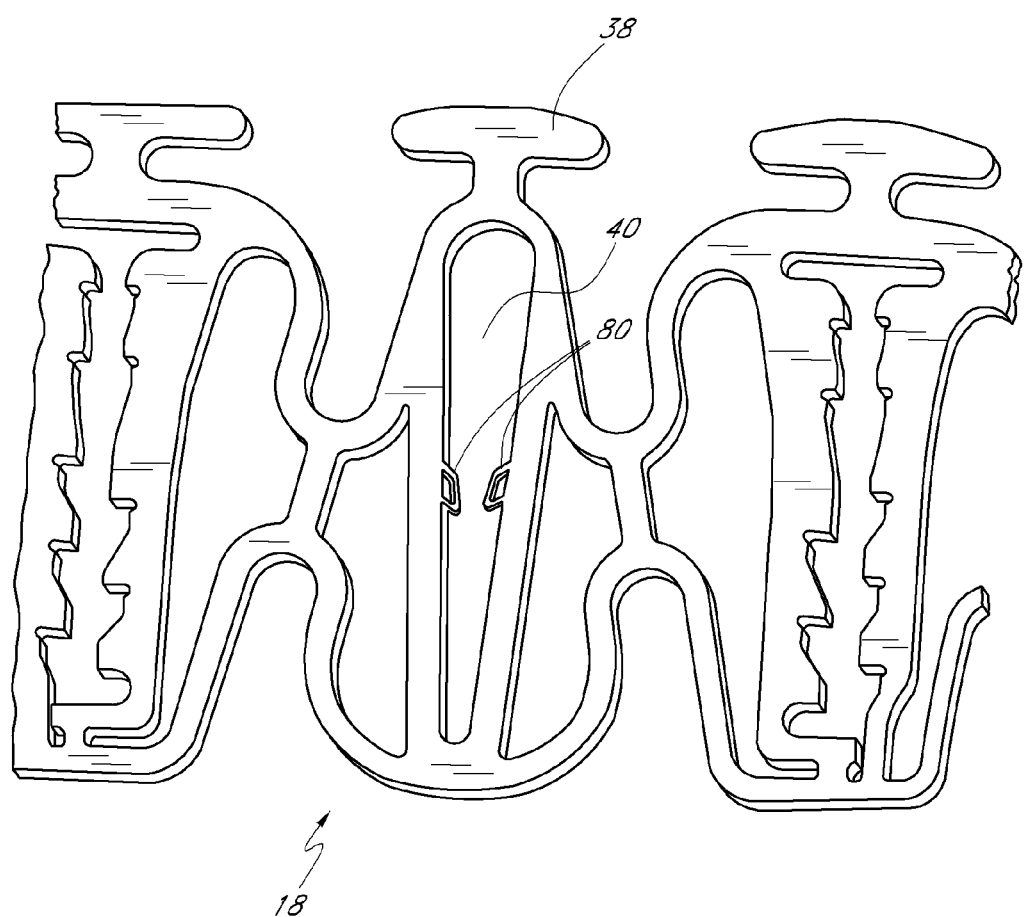
FIGS. 16 and 17 are a planar partial views of a slide-and-lock stent having a frangible deployment control mechanism incorporated into a passive radial element in accordance with one embodiment of the invention.
Figure 17:
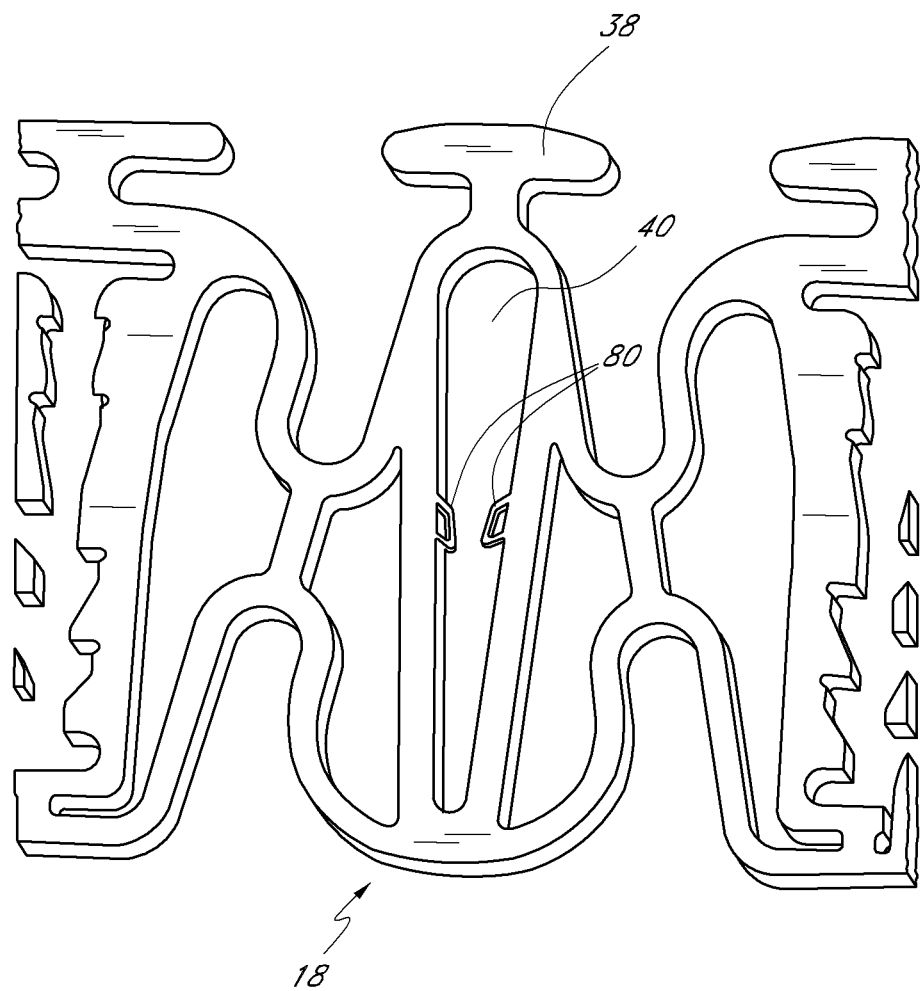

FIGS. 16 and 17 are partial views of a slide-and-lock stent module incorporating a frangible deployment control mechanism. The drawings show partial modules with passive radial element 18 having a safety tab 38 and a non-locking (toothless) slot 40, similar to those shown with reference to FIG. 4; however, the passive radial element in FIGS. 16 and 17 include frangible members 80 that extend into the slot 40. Lengthwise adjacent radial elements are preferably attached by a weldless connection, and more preferably formed from the same piece of material. FIG. 16 shows the passive radial element 18 before plastic deformation of the frangible members 80 and FIG. 17 shows the passive radial element 18 after plastic deformation of the frangible members 80.

In the embodiment illustrated in FIGS. 16 and 17, the frangible (plastically deforming) members 80 serve as a deployment control mechanism. The frangible members 80 act as a positive stop for a radially adjacent radial element having a safety tab slidably engaged within slot 40. During radial expansion, the slideably engaged radial element plastically deforms the obstructing frangible members 80 out of the path of its safety tab. This feature provides a temporary stop which allows other elements to fully expand before the temporary stop is overcome by additional radial expansion force. This feature is advantageous in facilitating uniform deployment.

Tapered/Non-Uniform Geometries to Improve Profile and Flow

The embodiments illustrated in FIGS. 18-21 utilize cross-sectional geometrical shapes of the radial elements that are modified/optimized to reduce the turbulence of the blood in lumen flow and/or create generally desirable blood flow characteristics. Stated differently, fluid flow principals are utilized to provide a strut or wall cross-section that is conducive to creating generally laminar and/or uniform flow characteristics.

Figure 18:
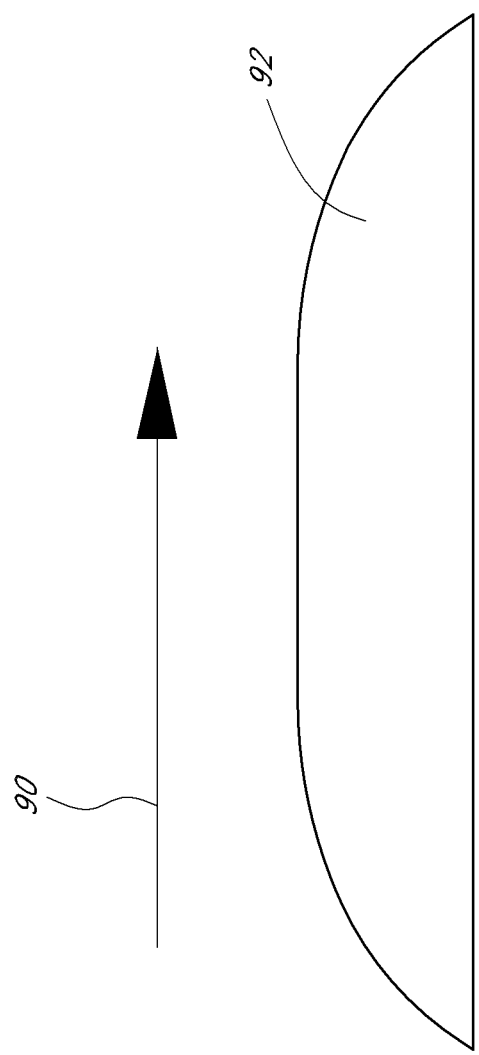
FIG. 18 is a simplified schematic view of a stent strut geometry configuration designed to create generally laminar flow conditions having features and advantages in accordance with one embodiment of the invention.
Figure 19:
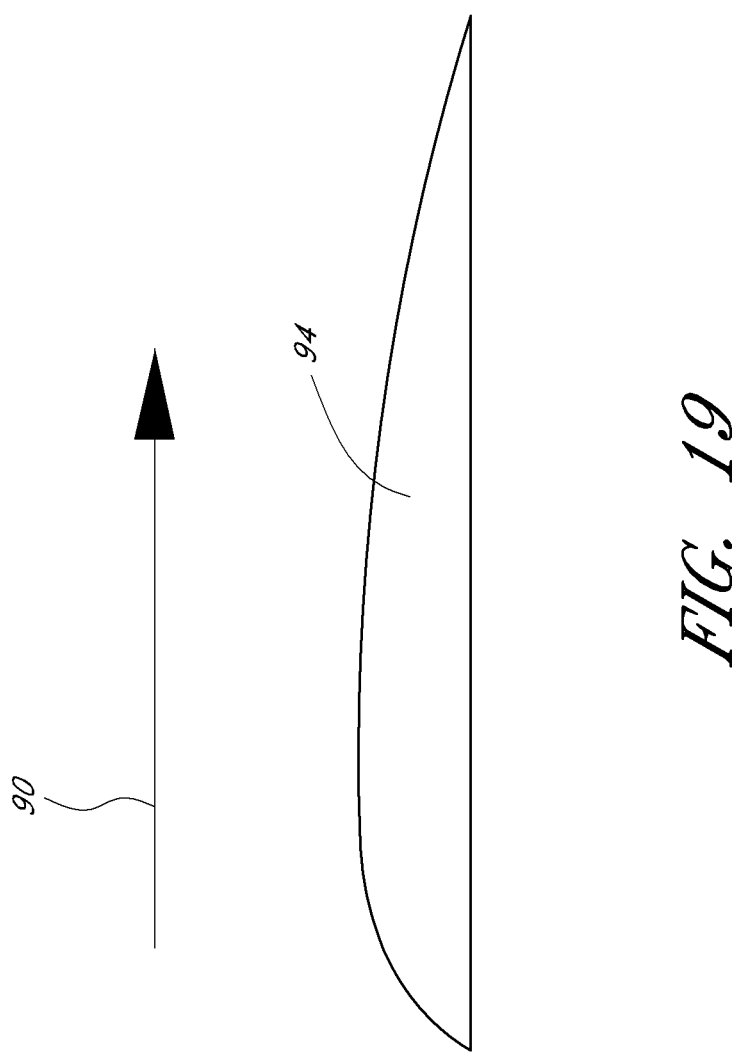
FIG. 19 is a simplified schematic view of another stent strut geometry configuration designed to create generally laminar flow conditions having features and advantages in accordance with another embodiment of the invention.

FIG. 18 illustrates one embodiment of a streamlined strut configuration 92 for creating generally laminar and/or uniform flow characteristics where the blood flow is generally in the direction indicated by arrow 90. FIG. 19 illustrates another embodiment of a streamlined strut configuration 94 for creating generally laminar and/or uniform flow characteristics. The direction of blood flow is generally indicated by arrow 90.

Figure 20:
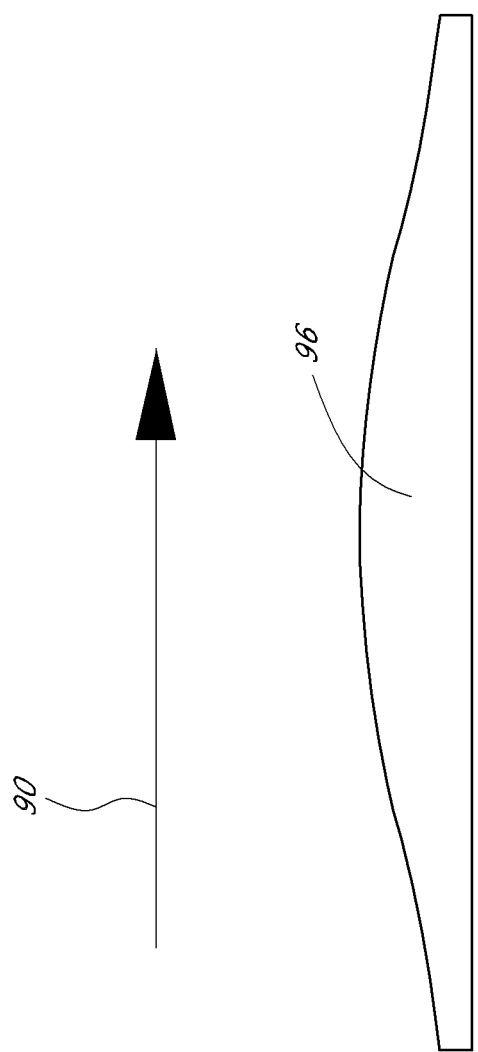
FIG. 20 is a simplified schematic view of a differential thickness stent strut configuration designed to create generally laminar flow conditions, increase strength and reduce profile, having features and advantages in accordance with one embodiment of the invention.

FIG. 20 illustrates an embodiment of a strut configuration 96 that utilizes a differential thickness beam, in either the axial or circumferential direction. A differential geometry can be employed to provide thickness and strength where needed or desired and allow for increased flexibility and minimized step down as needed or desired. The direction of blood flow is generally indicated by arrow 90.

Figure 21:
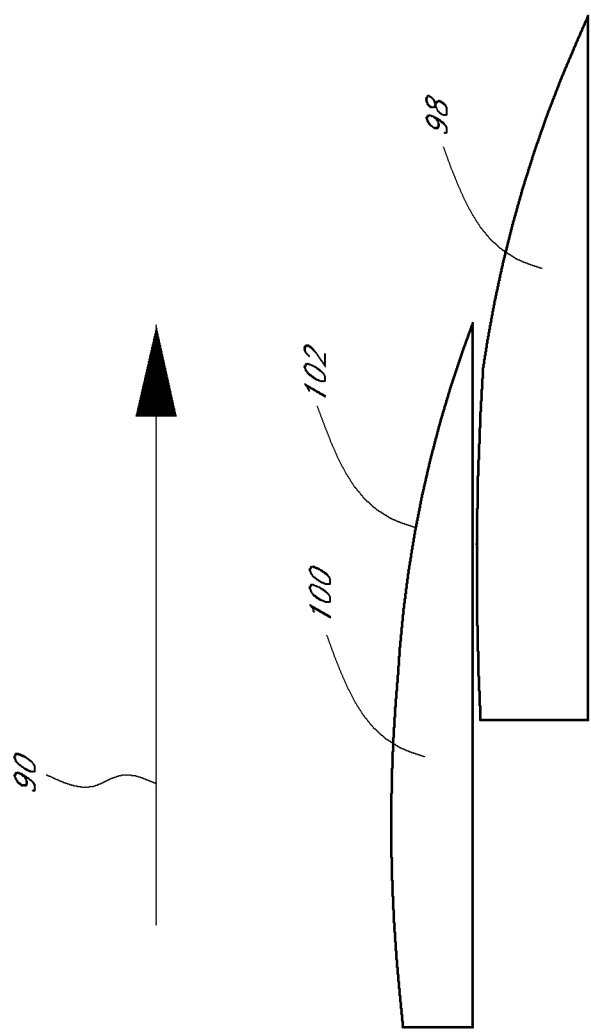
FIG. 21 is a simplified schematic view of a tapered overlap stent wall configuration designed to create generally laminar flow conditions having features and advantages in accordance with one embodiment of the invention.

FIG. 21 illustrates an embodiment that utilizes the streamlining concept to reduce step down effects between overlapping elements, such as elements 100 and 98. A tapered edge 102 allows the element 100 to blend into the underlying element 98 thereby, and advantageously, creating a substantially non-stepped transition point and eliminating any large step differential between the elements 100 and 98.

In another advantageous feature, it will be appreciated that preferred embodiments of the present invention provide very efficient surface coverage, which is particularly advantageous when the stent is used with a therapeutic agent. More particularly, the slide-and-lock mechanism is configured such that virtually all the surface area of the locking elements is in contact with the inner wall of the body lumen. Accordingly, the preferred embodiments allow for greater surface coverage as compared with existing stent configurations. When compared with other stent configurations, such as those utilizing deformable struts, the surface coverage may be increased to as much as 25% to 70% without compromising stent performance or flexibility. Because the stent shape of various preferred embodiments provides excellent surface coverage, a larger amount of the therapeutic agent may be delivered to the surrounding tissue. As a result, the agent may be used more effectively, thereby increasing the therapeutic effect. Alternatively, the therapeutic agent may be used in a lower concentration, thereby reducing local toxicity.

Solid Wall Stents and Grafts

Figure 22:
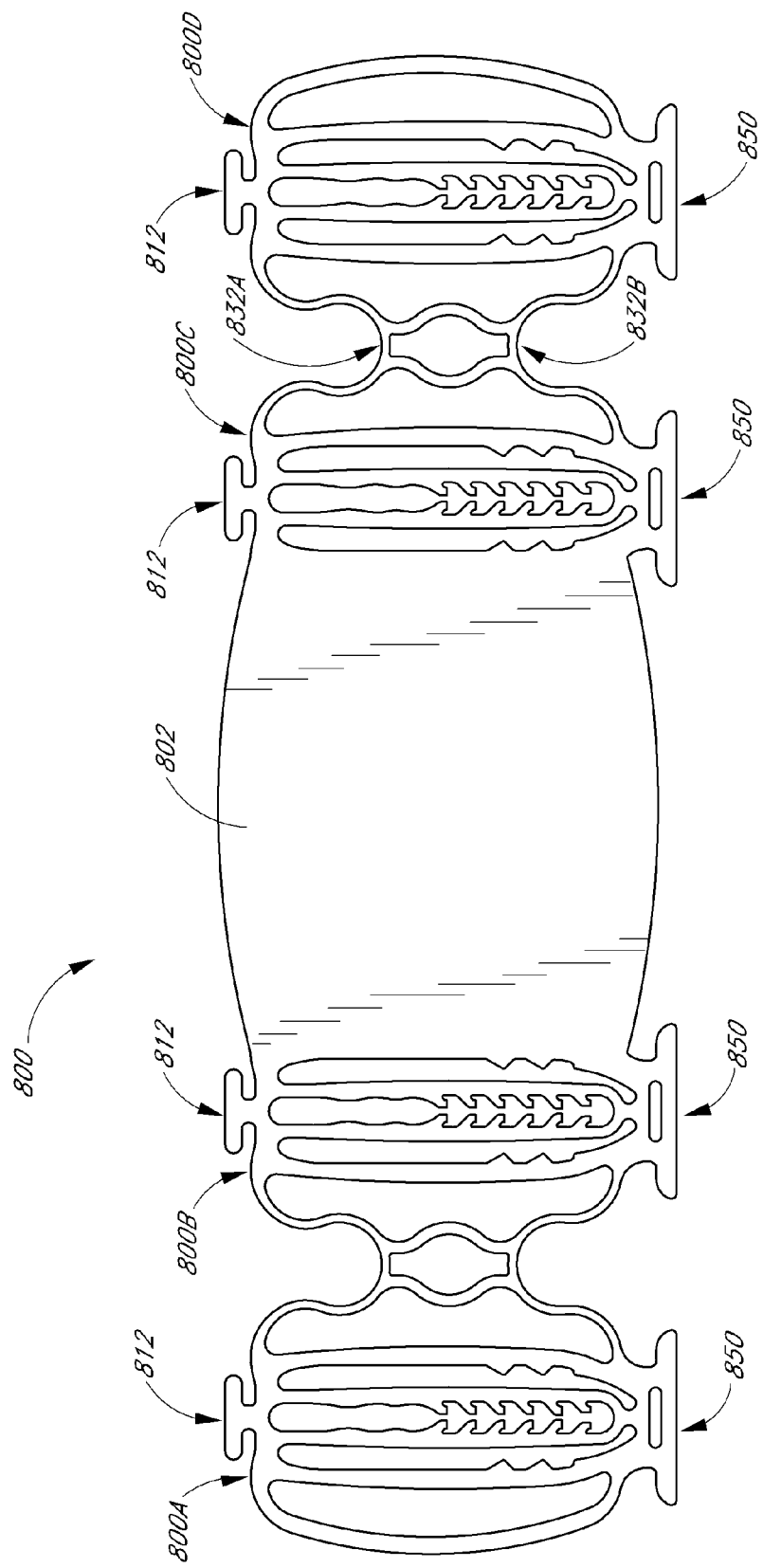
FIG. 22 is a plan view illustrating yet another preferred embodiment of a row of radial elements wherein a solid wall is provided along a center portion.

With reference now to FIG. 22, another module or row 800 of radial elements 800A-800D is illustrated that may be used alone or in combination with similar elements to provide an expandable stent structure. In many respects, the module or row 800 of radial elements 800A-800D is similar to the modules described above (See e.g., FIGS. 1-3). However, in this embodiment, the flexible body is formed with a solid wall 802 along a central portion of the row for providing enhanced surface coverage in a desired region of a body lumen. In variations to the embodiment illustrated in FIG. 22, the solid wall 802 may be disposed anywhere along the longitudinal length of the module or row. Moreover, in some embodiments it may be preferred to employ more than one solid wall along the length of the module. These solid wall regions may be adjacent to one another or separated.

More particularly, the solid wall 802 is preferably fabricated from an impermeable material and is configured to provide substantially complete coverage along a portion of a body lumen. In preferred embodiments, the solid wall 802 extends along the longitudinal axis at least 2 millimeters. Accordingly, this embodiment is particularly well suited for placement along a vascular anomaly, such as a vascular aneurysm, for supporting or sealing off a particular region along a vessel.

In the illustrated embodiment, each radial element 800A-800D comprises a locking tab 812 that interacts with teeth along deflectable rails for providing a locking mechanism. In some embodiments, e.g., where the stent is fabricated from a shape-memory material (e.g., Nitinol), each radial element 800A-800D may include a hold-down tab 850 sized to be releasably held within a recess for providing a hold down mechanism. It should be appreciated that a wide variety of locking mechanisms and hold-down mechanisms may be used (See e.g., those detailed in co-pending U.S. application Ser. No. 10/897,235; the entire disclosure of which is incorporated herein by reference), and that the illustrated embodiment is merely for the purpose of description. Flexible coupling members 832A, 832B may be provided between individual elements to provide enhanced flexibility. In one preferred embodiment, the module or row 800 of elements is fabricated from a shape memory material to provide crush-recoverability. During use, the radial elements comprising the module or row 800 are preferably slidably interconnected with other similar radial elements in circumferentially adjacent modules or rows to provide a balloon expandable stent. However, in an alternative configuration, the element 800 of FIG. 22 may be wrapped onto itself to provide an expandable stent.

Figure 23:
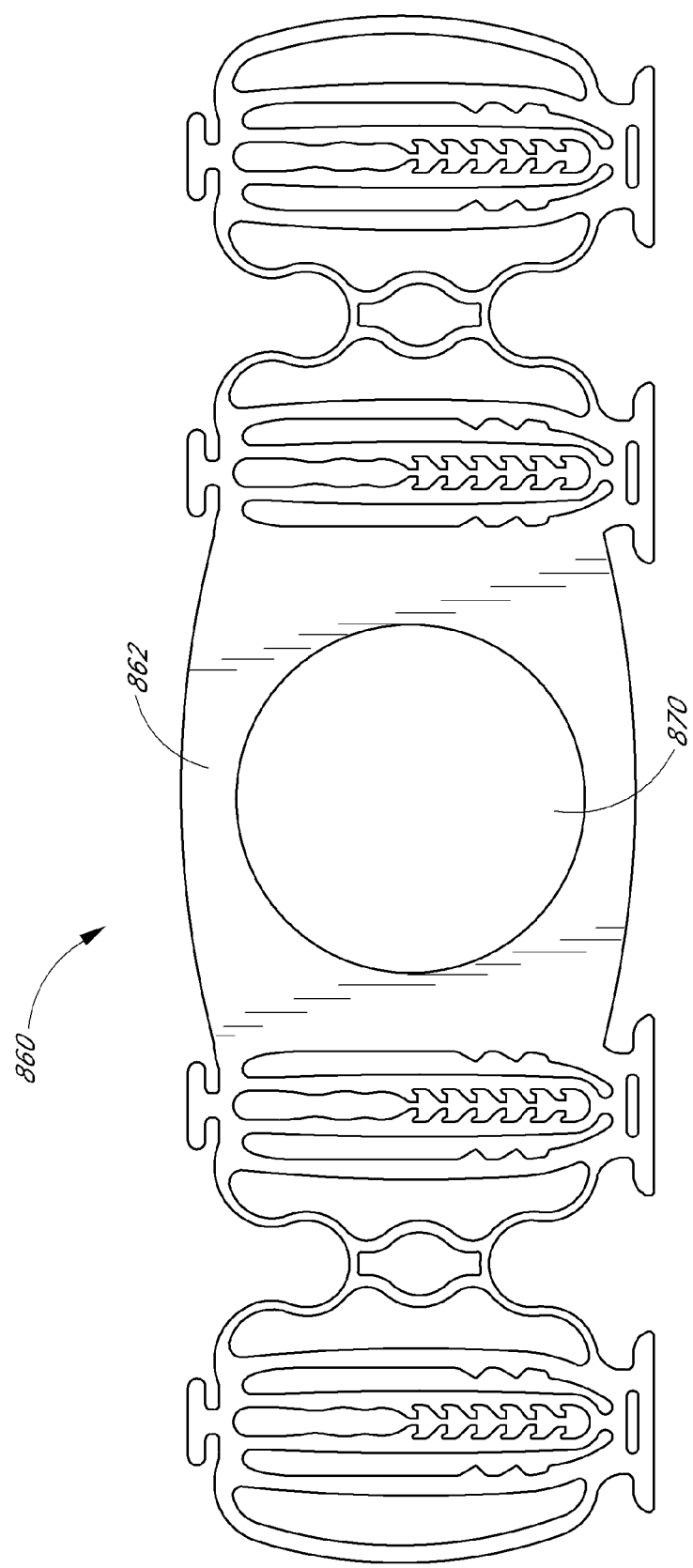
FIG. 23 illustrates a variation of the element of FIG. 22 wherein an opening is provided along the center portion of the solid wall for providing fluid communication with a branch vessel.

With reference now to FIG. 23, an alternative row 860 is illustrated which further comprises an opening 870 (e.g., a circular hole) formed in the wall portion 862. The opening is preferably provided for allowing fluid communication through the wall 862. Accordingly, this variation 860 is particularly well suited for treating a lesion along a vessel bifurcation. The row 860 may be interconnected with one or more rows 800 of the type described above with respect to FIG. 22 to provide an expandable stent having a solid central portion formed with an opening. When deployed, the stent may be advantageously used to ensure the patency of a main vessel while allowing blood to flow into or out of a branch vessel. In yet other variations, the wall may be permeable or a filter may be provided along the opening 870 for preventing emboli or other debris from passing through the opening.

Of course, it will be appreciated that deflectable teeth may be used in those embodiments shown in FIGS. 22-23, rather than deflectable rails or members (as shown), to provide the stent with mono-directional expansion. A detailed description of deflectable teeth and accompanying illustrations are provided below with reference to FIGS. 25-27.

Figure 24:
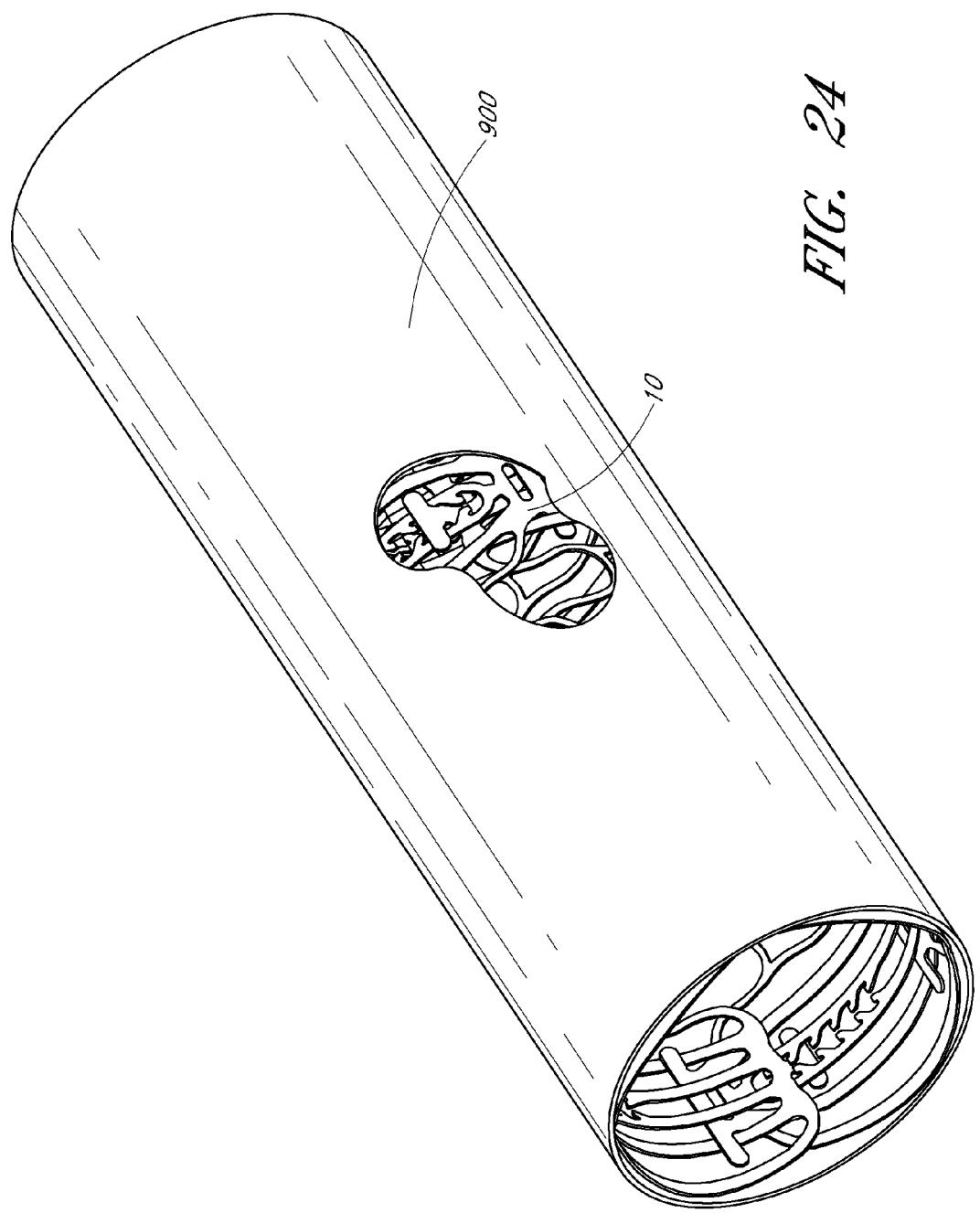
FIG. 24 illustrates another variation of an expandable stent wherein an expandable sheath is disposed over the expandable stent structure.

In yet another variation, stent embodiments configured in accordance with the present invention may also be useful in vessel grafts, wherein the stent is covered with a sheath formed at least in part from either a polymeric material, such as expanded PTFE, or a natural material, such as fibrin. One variation of a graft in accordance with the present invention is illustrated in FIG. 24. The tubular graft comprises an expandable stent 10 of the type described herein with reference to FIGS. 1-23 and 25-35 and a polymeric sheath 900. Because of the low profile, small collapsed diameter and great flexibility, stents made in accordance with this embodiment may be able to navigate small or torturous paths. Thus, this variation may be useful in coronary arteries, carotid arteries, vascular aneurysms (when covered with a sheath), renal arteries, peripheral (iliac, femoral, popliteal, subclavian) arteries. Other nonvascular applications include gastrointestinal, duodenum, biliary ducts, esophagus, urethra, tracheal and bronchial ducts.

Deflectable Teeth Lockout Mechanisms

Figure 25:
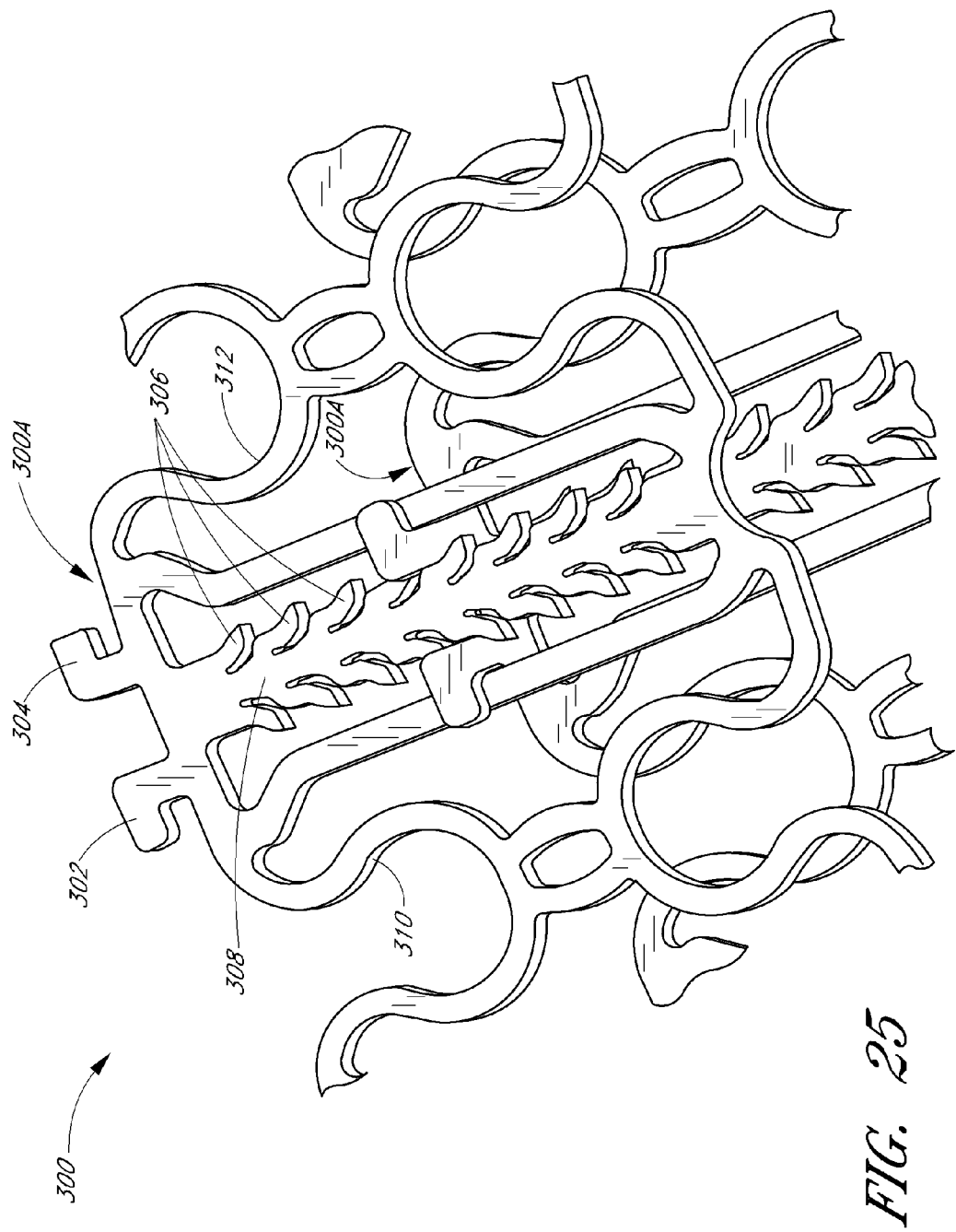
FIG. 25 illustrates an alternative structure comprising deflectable teeth which deflect inward to provide a stent exhibiting mono-directional expansion.

In yet another alternative embodiment, it will be appreciated that deflectable teeth may be used, rather than deflectable rails or members, to provide the locking mechanism that facilitates mono-directional expansion. For example, FIG. 25 illustrates a portion of another stent embodiment 300 wherein two radial elements 300(1), 300(2) are slidably interconnected. Each radial element is provided with a rail 308 having a plurality of deflectable teeth 306. Similar radial elements may be coupled via flexible linkage elements 310, 312 to provide a stent having a desired axial length. In this embodiment, the engagement means comprise locking tabs 302, 304 which are configured to slide circumferentially within elongate slots surrounding the rail, and to slide along the sides of the deflectable teeth 306. Each of the teeth is sufficiently flexible such that the teeth may deform inward toward the rail 308 (i.e., within the plane of the radial element) for allowing the locking tabs 302, 304 to pass in one direction. However, due to the angle of the teeth, the locking tabs are prevented from moving in the other direction, thereby providing yet another preferred mechanism for maintaining the stent in the expanded condition after deployment.

Figure 26:
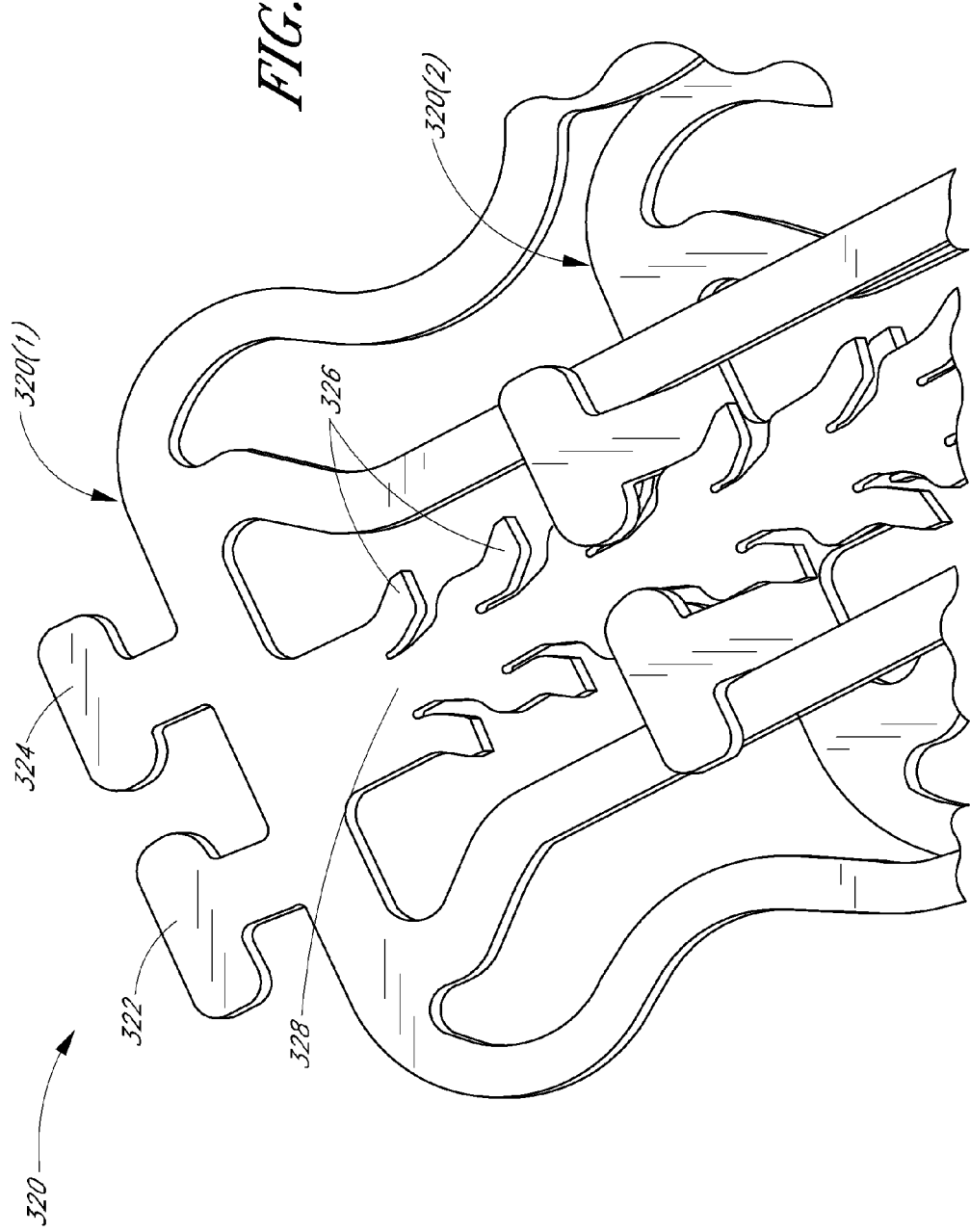
FIG. 26 illustrates another alternative structure comprising deflectable teeth which deflect downward to provide a stent exhibiting mono-directional expansion.
Figure 27:
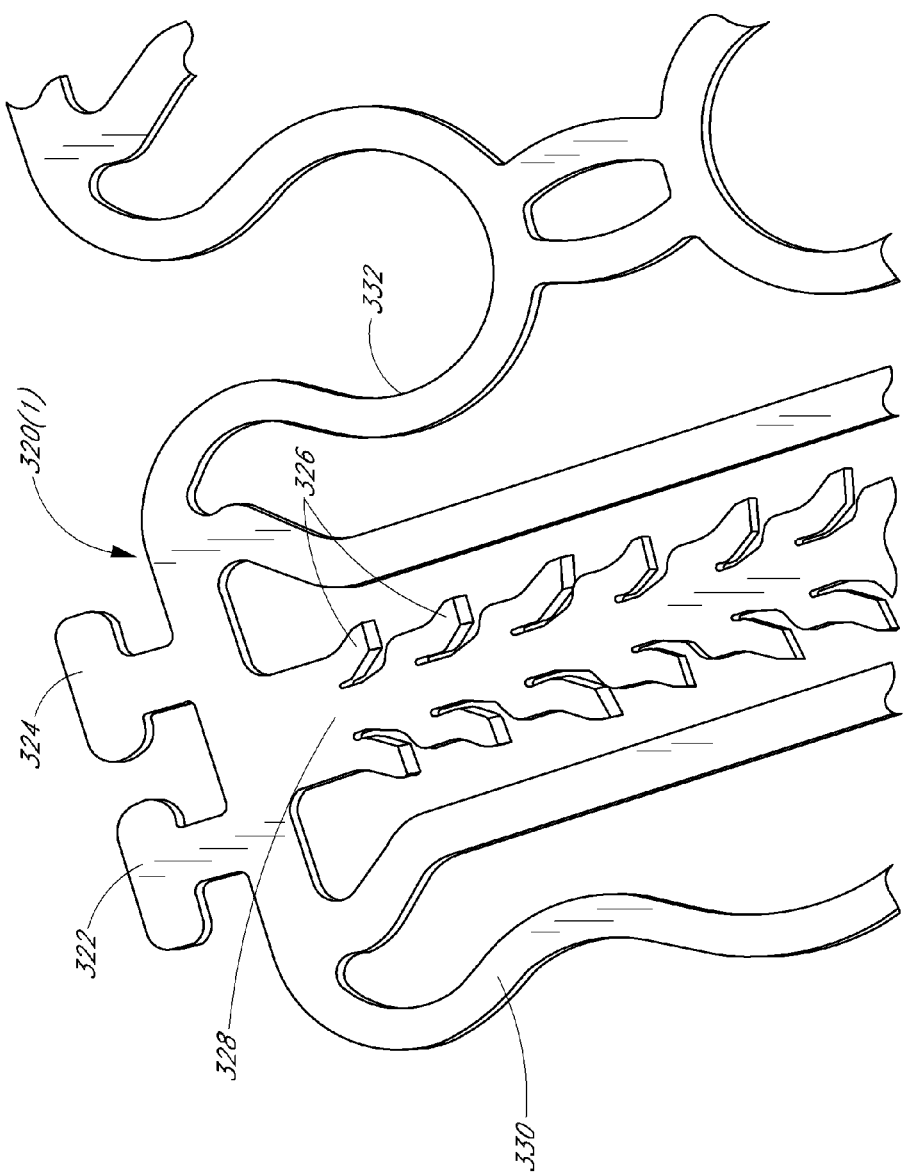
FIG. 27 illustrates a portion of a single element from the embodiment shown in FIG. 26.

With reference now to FIG. 26, a portion of another preferred stent embodiment 320 is illustrated wherein radial elements 320(1), 320(2) are slidably interconnected. Similar to the embodiment just described, each radial element is provided with a rail 328 having a plurality of deflectable teeth 326. However, in this embodiment, each of the teeth is angled upward and is configured to deflect downward (i.e., in a radial direction), rather than inward toward the rail as discussed with respect to FIG. 25. As the locking tabs 322, 324 slide along the deflectable teeth 326, the teeth are caused to deflect downward for allowing the tabs 322, 324 to pass over the teeth 326 during deployment. However, due to the angle of the teeth, the locking tabs may only move in one direction. More particularly, if a compressive force pushes the radial elements 320(1), 320(2) back toward the collapsed condition, the locking tabs 322, 324 will abut against the teeth 326, thereby preventing further relative movement. For additional reference, FIG. 27 illustrates radial element 320(1) in isolation. Flexible linkage elements 330, 332 allow multiple radial elements to be joined to form a row.

Figure 28A:
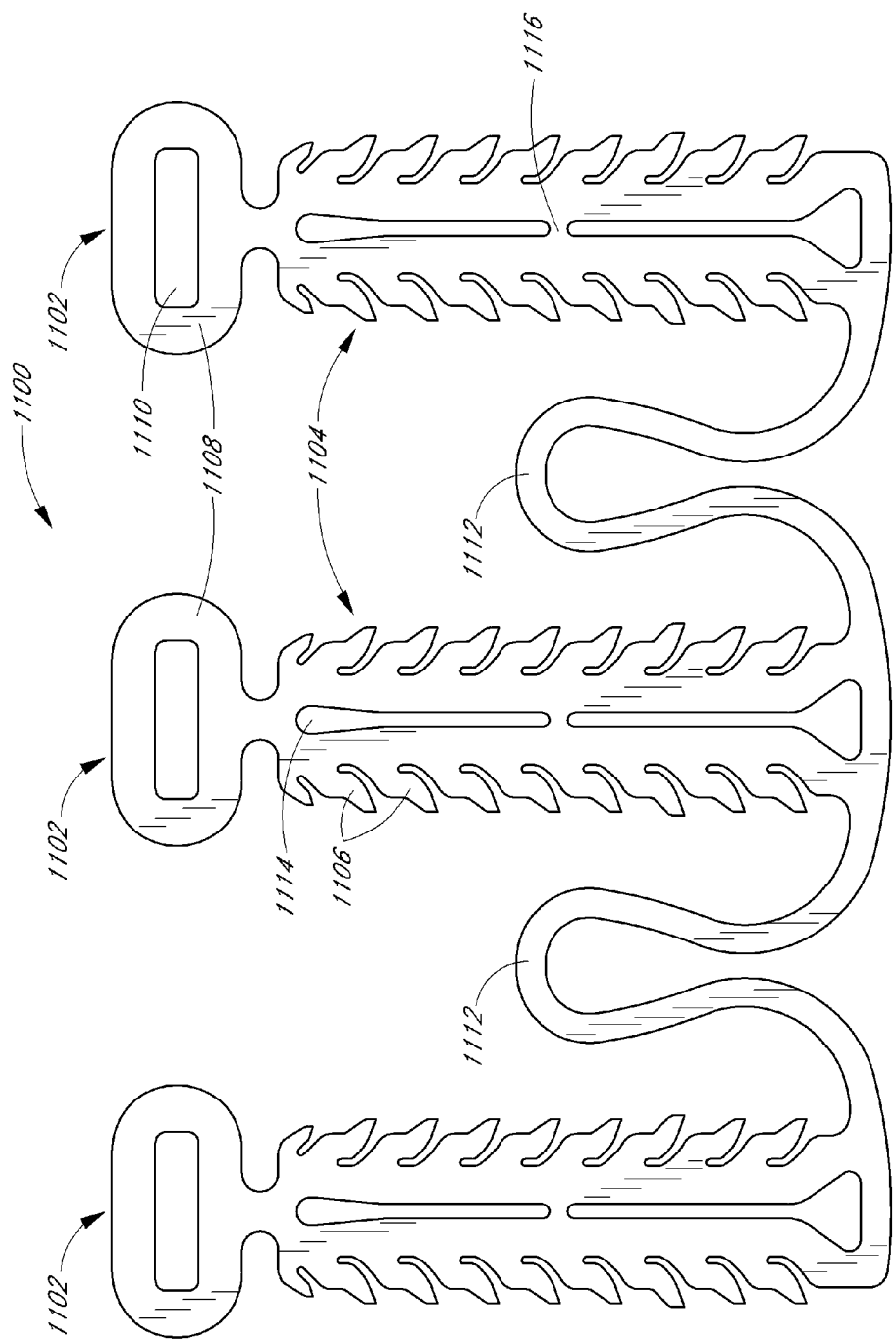
FIG. 28A is a plan view illustrating another preferred embodiment of an expandable stent comprising radial elements having deflectable teeth and a closed loop.
Figure 28B:
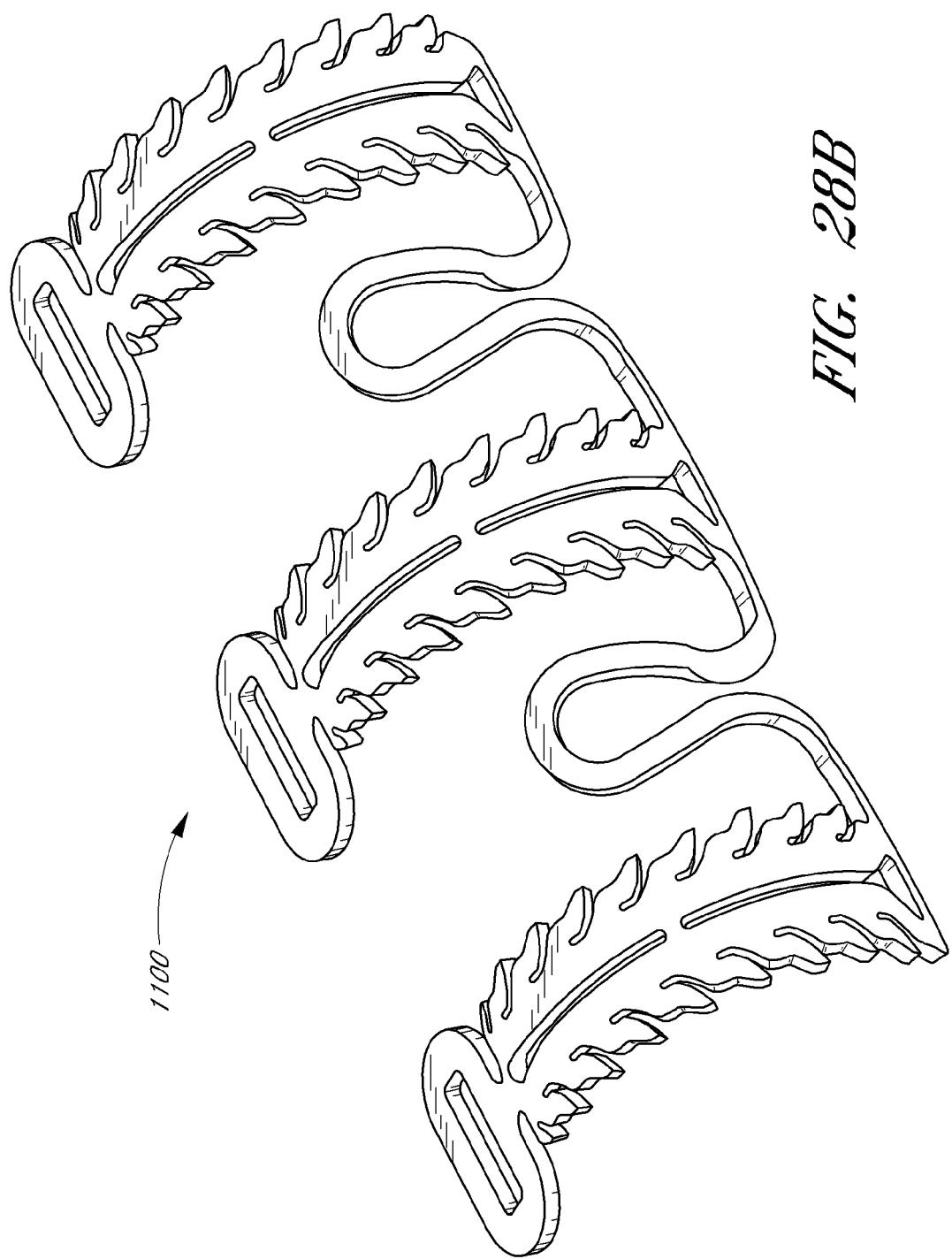
FIG. 28B illustrates the single module of FIG. 28A rolled into a partial tubular member.
Figure 28C:
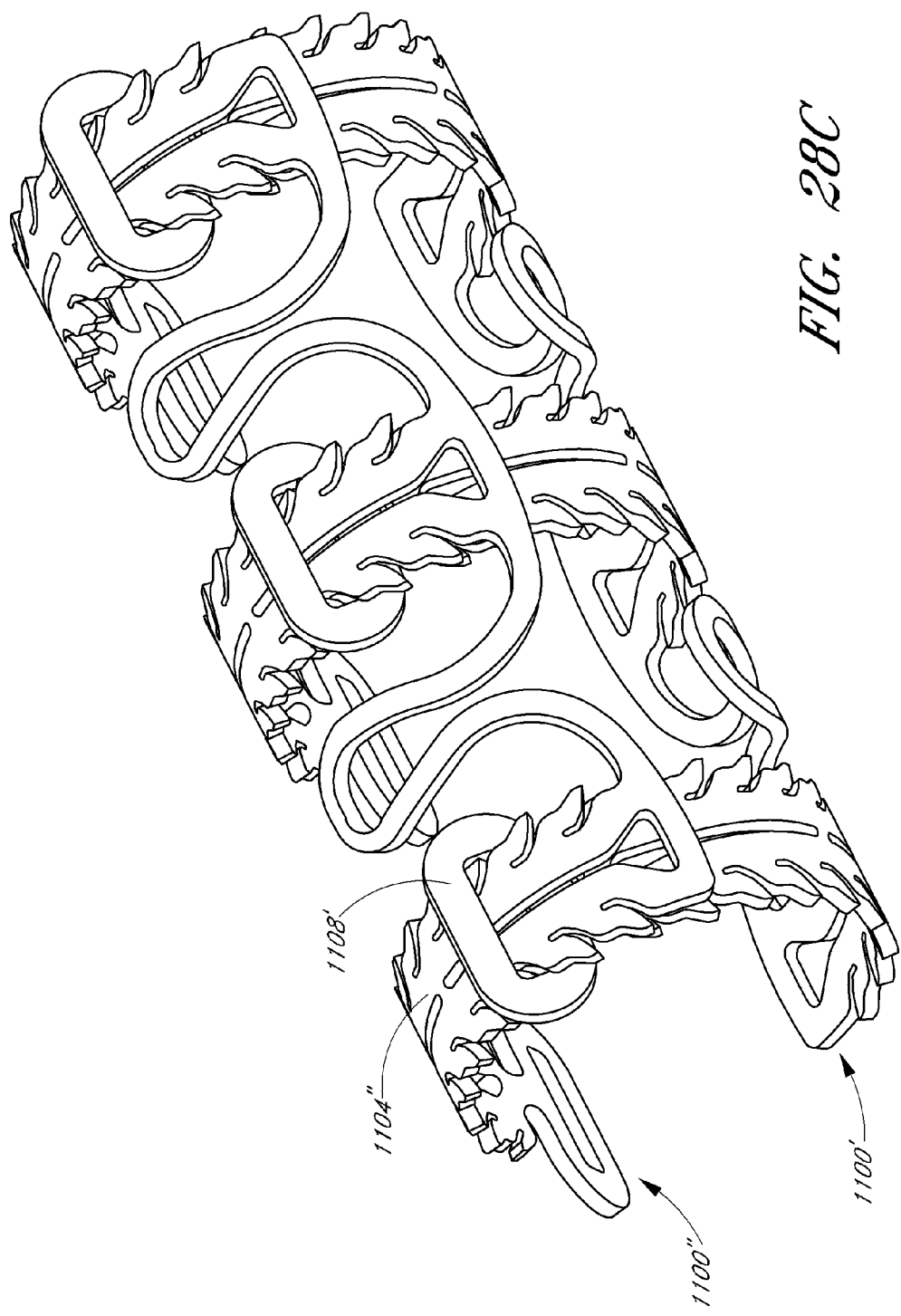
FIG. 28C illustrates the articulation of two modules of FIG. 28A slidably interlocked to form a partial tubular member.

With reference to FIGS. 28A-C, another embodiment of the slide-and-lock stent is illustrated, wherein the locking mechanism comprises deflectable teeth disposed on rails similar to those shown in FIGS. 25-27; however, after assembly, a rail is slidably engaged within engagement means comprising a closed loop which defines a slot. FIG. 28A shows a plan view of such a module 1100 comprising three radial elements 1102. Each radial element comprises a rail 1104 comprising a plurality of deflectable teeth 1106, and a closed loop 1108, which forms a slot 1110 configured to slidably engage a rail 1104 from a circumferentially adjacent radial element 1102 in a circumferentially adjacent module or row 1100. The slot 1110 is also configured to accept the loop 1108 and rail 1104 from the adjacent radial element during assembly, such that circumferentially adjacent modules can be slidably interlocked without welding or bonding of any sort required. In the illustrated embodiment, the longitudinally adjacent radial elements 1102 are connected to one another via flexible linkage elements 1112. Of course, any linkage configuration may be substituted without departing from the inventive elements of this embodiment. The illustrated rails 1104 have a central gap 1114 that may be configured to provide more or less deflection of the teeth 1106 as they pass through the slot 1110 during expansion. One or more bridges 1116 may connect the two sides of the divided rail. Generally, the more bridges the less deflection the rail may offer.

FIG. 28B shows the same module 1100 illustrated in FIG. 28A, except it has been bowed to show how the module comprises a portion of the circumference of a stent assembled from 2 or more such modules.

FIG. 28C illustrates a partial stent comprising two modules 1100' and 1100" like those shown in FIGS. 28A and 28B. It will be appreciated that the rail 1104" from module 1100" is slidably engaged in the slot 1110' formed in closed loop 1108' from module 1100'.

Figure 29:
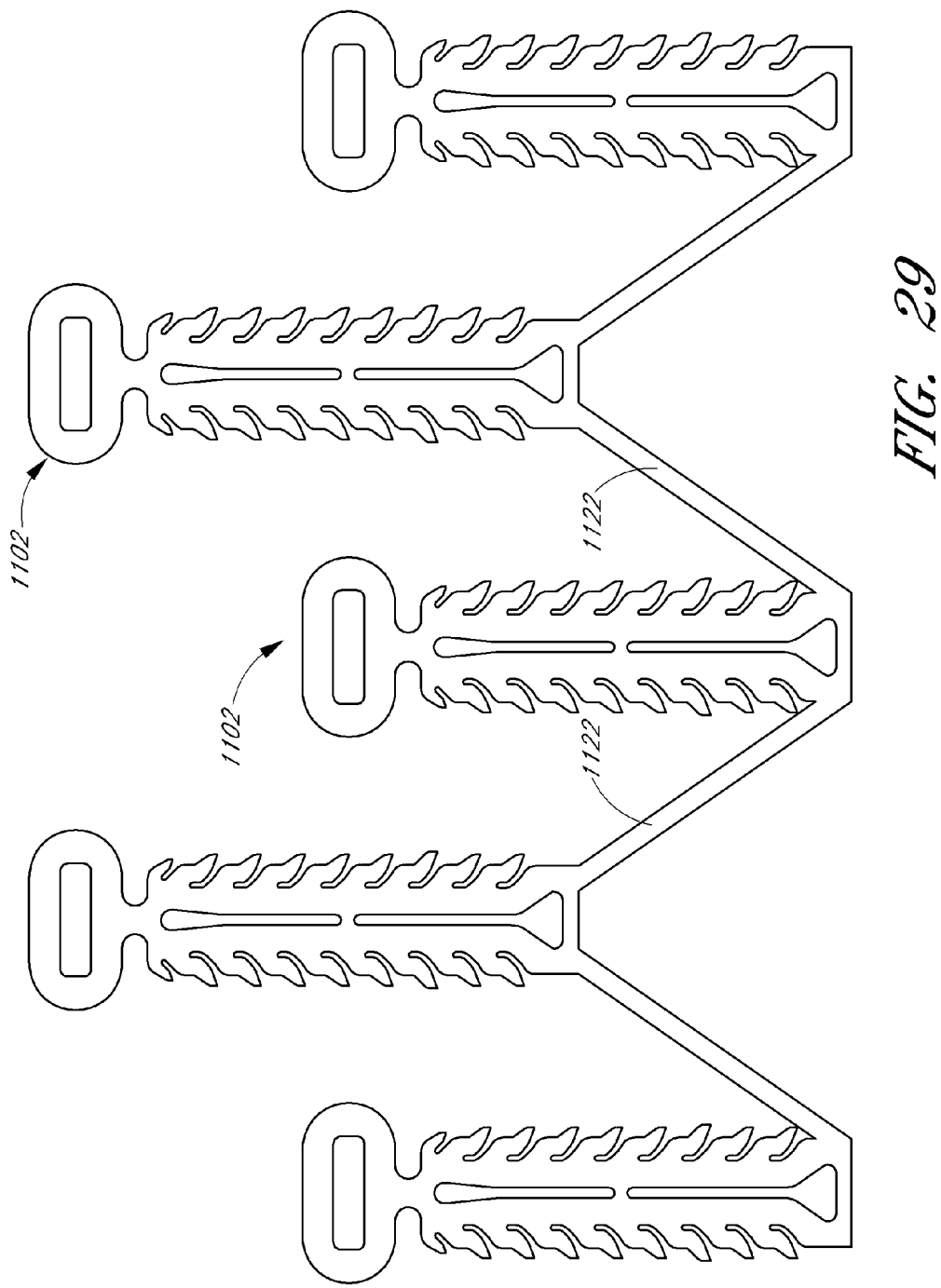
FIG. 29 is a plan view illustrating another preferred embodiment of a deflectable tooth module comprising circumferentially offset radial elements.

A variation to the deflectable tooth slide-and-lock module shown in FIGS. 28A-C is illustrated in FIG. 29, wherein the longitudinally adjacent radial elements 1102 are circumferentially offset by angled linkage elements 1122.

Serrated Surface Lockout Mechanisms

Figure 30:
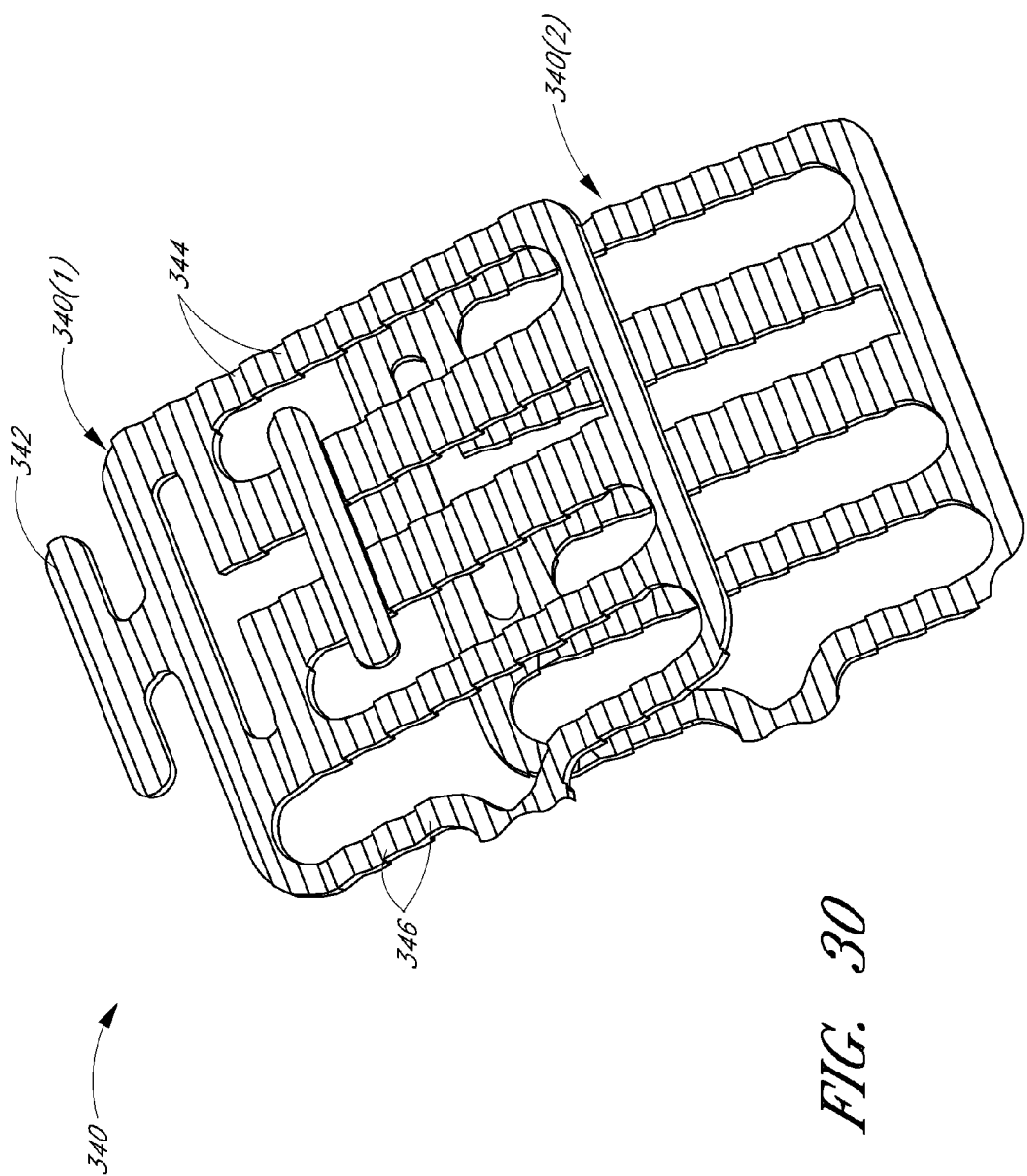
FIG. 30 illustrates another alternative structure comprising a single tab and series of shaped ridges that provide a stent exhibiting mono-directional expansion.

With reference now to FIG. 30, a portion of another stent embodiment 340 is illustrated wherein radial elements 340(1), 340(2) are slidably interconnected. Each radial element is provided with an outer surface formed, at least in part, with a series of serrations or ridges. More particularly, the surfaces comprise a series of valleys 344 and ridges 346. In the illustrated configuration, a locking tab 342 of radial element 340 (2) slides along the surface of radial element 340(1). The locking tab 342 is formed with a thin neck portion 350 and a wider head portion 352. The neck portion 350 is configured for allowing the head 352 to deflect outward in a radial direction. The shape of the valleys 344 and ridges 346 allows the head 352 of the locking tab 342 to ratchet along the surface of the adjacent element in only one direction, thereby providing a locking means to maintain the stent in the expanded condition. Although the ridges and valleys are only necessary along the region wherein the locking tab slides, each of the radial elements may be formed with a continuous contoured surface for ease in manufacturing. In one variation, the shaped bottom surface of the first element 340(1) may slide along the top surface of the shaped second element 340(2) for providing the desired ratcheting effect. In this variation, the tab 342 may be used primarily for interconnecting the elements in a slidable configuration.

Variations in Lockout Mechanisms and Circumferentially Offset Radial Elements

Figure 31:
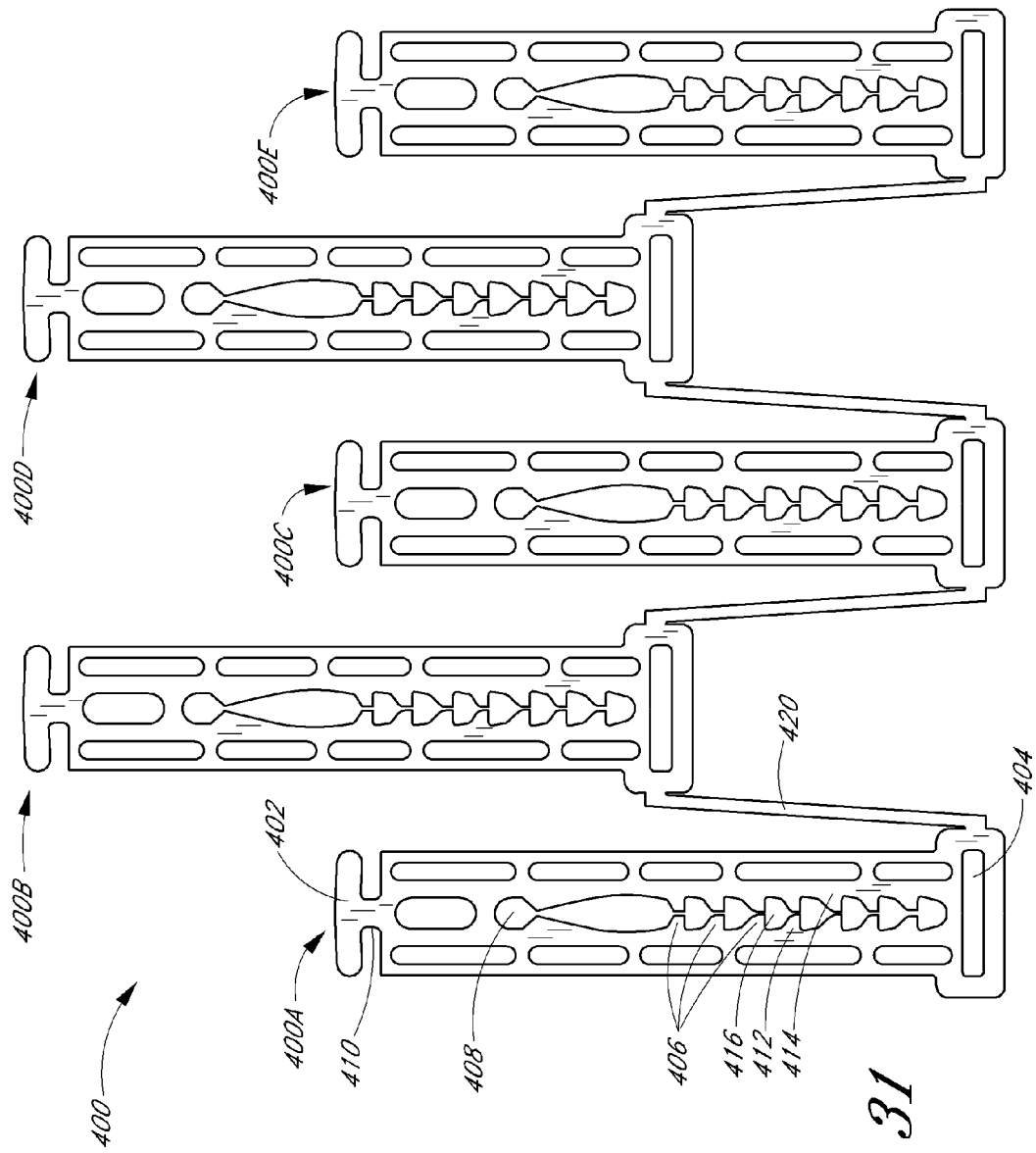
FIG. 31 illustrates another alternative structure comprising a row of staggered radial elements that may be interconnected with similar structures to form an expandable stent.

With reference now to FIG. 31, another alternative module or row 400 of radial elements 400A-400E is illustrated. In this embodiment, the individual radial elements in a module or row are coupled in a staggered, circumferentially offset arrangement by a series of flexible coupling elements 420. In preferred embodiments, the illustrated module or row 400 may be slidably interconnected with other similar, circumferentially adjacent modules to provide a stent. Each of the radial elements is substantially identical and includes a locking tab 402 having a neck portion 410. Each of the radial elements further includes a containment gap 408 for holding an adjacent locking tab and a series of opposing teeth 406 along the containment gap for providing a mono-directional expansion.

With reference now to FIGS. 32A and 32B, the slide-and-lock relationship between interconnected radial elements of the type shown in FIG. 31 is illustrated. FIG. 32A shows the radial elements 400A(1), 400A(2) in a collapsed configuration wherein the locking tab 402 of radial element 400A(2) is held within the containment gap 408 of radial element 400A (1). The body of radial element 400A(2) extends through a slot 404 formed in radial element 400A(1) for maintaining the elements in the desired slidable relationship. FIG. 32B shows the radial elements 400A(1), 400A(2) in an expanded condition. As shown in FIG. 32B, the locking tab 402 of 400A(2) is disposed in the gap 416 between deflectable members 412, 414 of 400A(1) and is locked in place by teeth 406.

Figure 32:
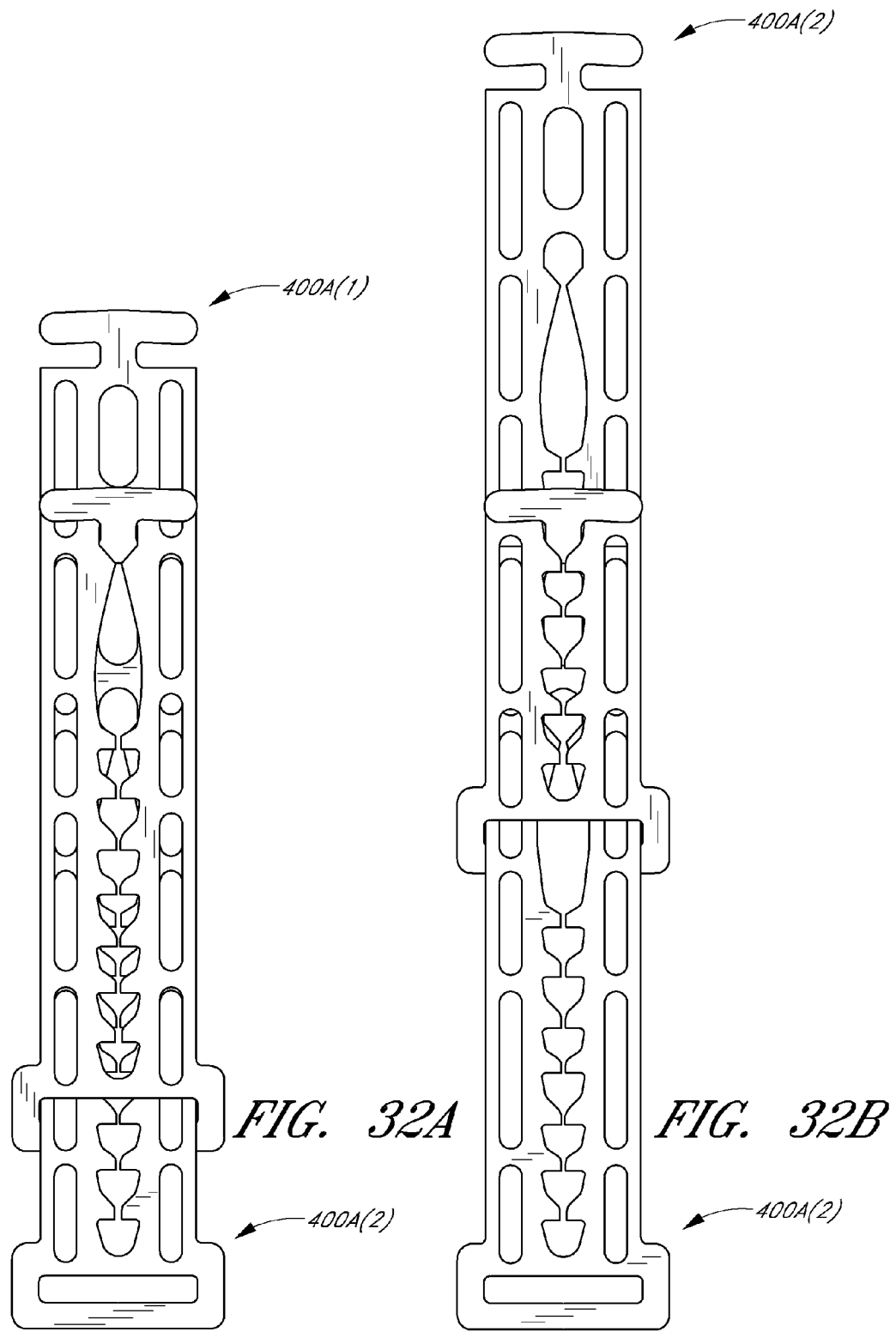
FIG. 32A is a plan view illustrating slidably interconnected radial elements of the type illustrated in FIG. 31 which are constrained in the collapsed condition.
FIG. 32B is a plan view illustrating slidably interconnected radial elements of the type illustrated in FIG. 31 which are locked-out in the expanded condition.

In one advantageous feature, a stent comprising the sliding and locking rows illustrated in FIGS. 31 through 32B provides improved uniformity in surface coverage due to the staggered relationship of the individual radial elements. Furthermore, the stent is capable of providing adequate support to the body lumen while minimizing the total area of surface coverage. This is a particularly advantageous feature since a large percentage of the natural inner surface of the body lumen remains exposed after stent deployment. In another advantageous feature, each radial element passes through the slot 404 of the adjacent radial element for securely maintaining the components in a slidably interlocked condition. Still further, this stent embodiment provides excellent flexibility after deployment.

As discussed above, it will be appreciated by those skilled in the art that stents constructed according to the present invention may comprise a wide variety of other slide-and-lock elements while still providing the features and advantages described herein. The slide-and-lock elements illustrated and described above are merely preferred embodiments and alternative slide-and-lock elements may be employed without departing from the scope of the invention. For example, a variety of alternative one-way locking mechanisms, which may be used to facilitate mono-directional stent expansion, can be found in Applicant's co-owned U.S. Pat. Nos. 6,033,436, 6,224,626 and 6,623,521, each of which is incorporated by reference herein.

Figure 33:
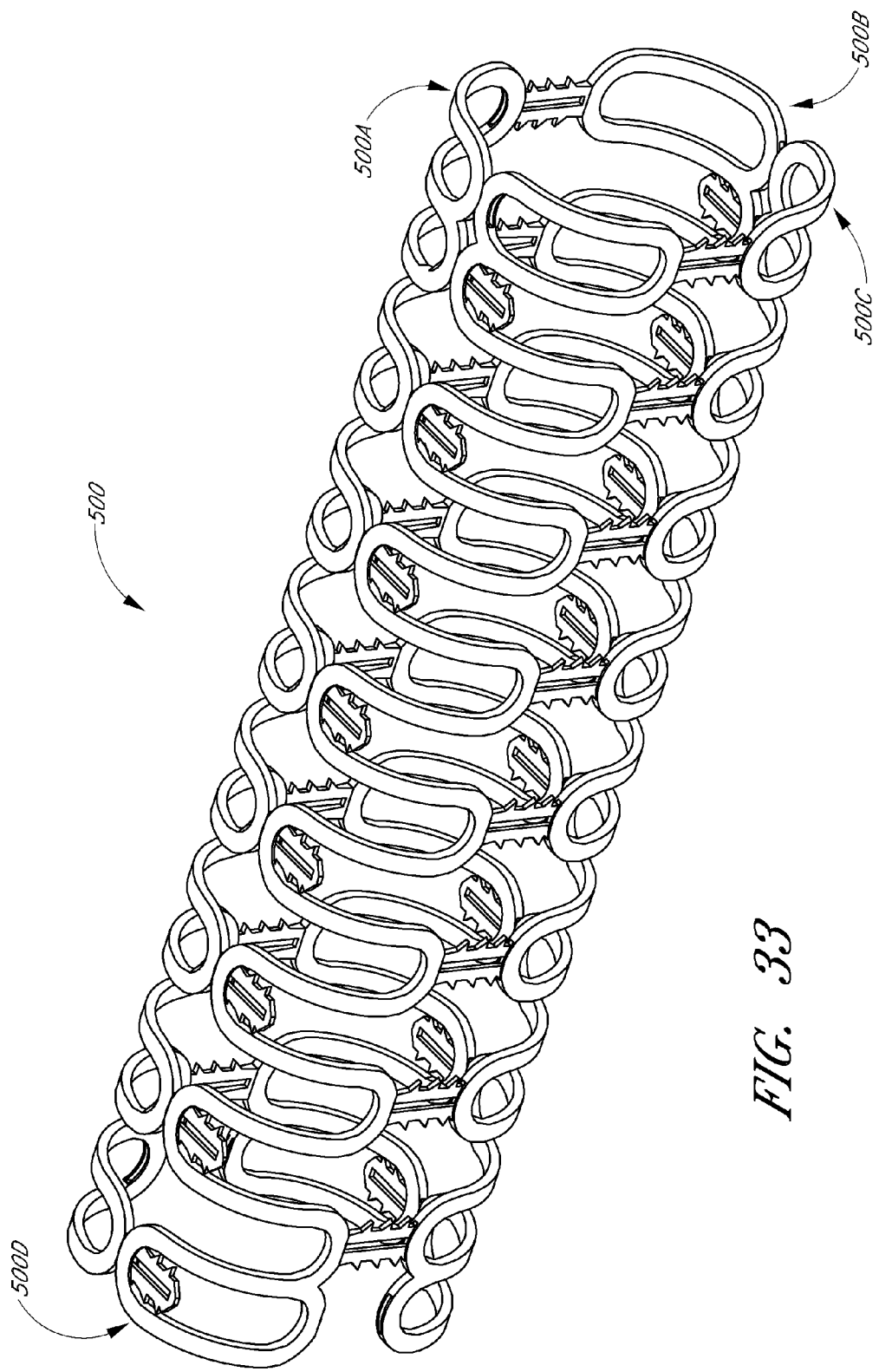
FIG. 33 is a perspective view illustrating another preferred embodiment of an expandable stent comprising a plurality of interconnected flexible rows.

With reference now to FIG. 33, yet another preferred embodiment of a stent 500 comprises alternative slide-and-lock mechanisms which are interconnected to provide a tubular member sized for deployment in a body lumen. In the illustrated embodiment, a plurality of interconnected rows 500A-500D is provided wherein each row preferably extends along the entire axial length of the stent 500. This stent configuration advantageously combines excellent longitudinal flexibility (i.e., bending) with a very high radial strength. Although the stent 500 shown in FIG. 33 is illustrated with four interconnected rows 500A-500D, the number and length of the rows may vary to meet the particular requirements of the application.

Figure 33A:
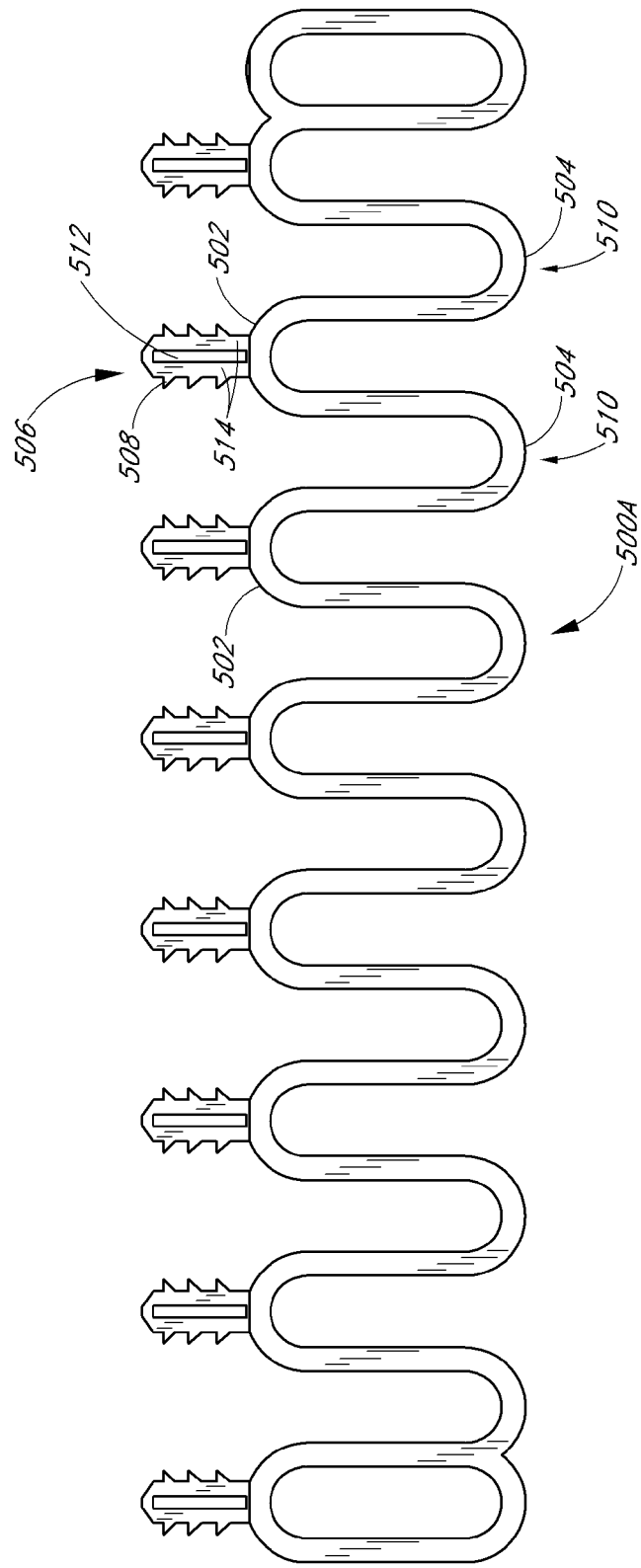
FIG. 33A is a plan view illustrating a single flexible row from the stent embodiment of FIG. 33.

With reference now to FIG. 33A, a single row 500A comprises a structure shaped for providing the stent with excellent flexibility along the longitudinal axis. This feature allows the stent to bend during delivery and to more easily conform to the shape of a body lumen after deployment. Furthermore, this embodiment eliminates the need for flexible linkage elements. The row 500A illustrated in FIG. 33A includes a series of peaks 502 and valleys 504 wherein each peak is provided with a protrusion 506 and each valley is provided with a slot (e.g., see 510 of FIG. 33) shaped for receiving an adjacent protrusion. Of course, not all peaks and valleys necessarily comprise protrusions or slots. As illustrated, each of the protrusions 506 is preferably provided with two parallel deflectable members 514 formed with a number of teeth 508. Each of the teeth 508 is formed with an angled side and a flat side. Furthermore, each of the protrusions 506 is formed with a gap 512 extending between the deflectable members 514.

When assembled, the protrusions 506 are slidably received within the slots 510 as illustrated in FIG. 33. The interaction between the angled teeth 508 and slots 510 is preferably configured to provide a stent 500 exhibiting mono-directional expansion. In particular, during expansion, the interaction between the teeth 508 and the slot 510 causes the deflectable members 514 to flex inward for allowing the teeth to pass through the slot 510. The deflectable members 514 are caused to flex inward because the edges of the slot act on the angled side of the teeth. However, when a force is applied in the other direction, the flat sides of the teeth abut against the edges of the slot and no inward force is produced. Accordingly, the teeth 508 are prevented from sliding back out of the slots 510, thereby maintaining the stent in the expanded condition after deployment at a treatment site.

In preferred embodiments, the force required to move the protrusions through the slots is large enough such that the stent will not inadvertently expand during delivery to the treatment site. Therefore, the stent is held down in the collapsed condition before deployment. If necessary, the assembly may be constructed such that the initial resistance produced by the first set of teeth on each protrusion is greater to ensure that the stent remains in the collapsed condition during delivery.

In an advantageous feature, each of the mating protrusions and slots may move (i.e., ratchet) independently of the others. Accordingly, in addition to providing excellent flexibility, the diameter of the stent may vary along the longitudinal axis for precisely conforming to the inner diameter of the vessel. In still another advantage, the protrusions are received within slots formed in the adjacent row. Therefore, the slide-and-lock mechanism maintains a very low profile after deployment. Indeed, in accordance with preferred embodiments, the modules comprising serpentine peaks 502 and valleys 504 may be fabricated from three or more layers of material (two outer layers and one or more inner layers), such that the slots 510 are defined by the outer layers, with a gap where at least one region of inner layers is missing, whereas the protrusions 506 are formed from the corresponding inner layer(s), with missing outer layers. Thus, as the protrusions articulate within the slots, there is no overlap of any stent elements. The thickness of the slidable articulation (between protrusions and slots) is substantially the same as the thickness of the rest of the stent.

Figure 34:
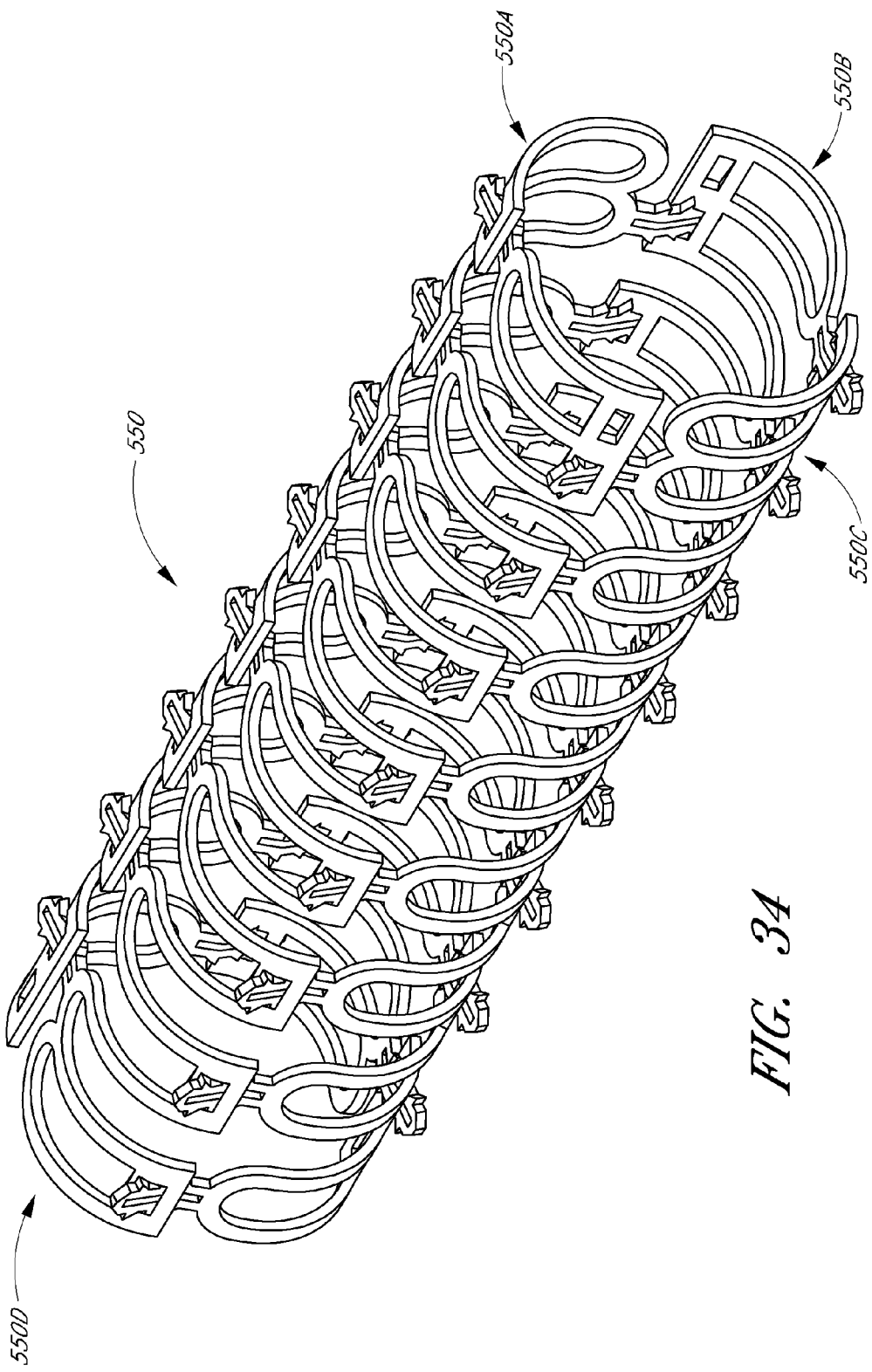
FIG. 34 is a perspective view illustrating yet another preferred embodiment of an expandable stent comprising a plurality of interconnected flexible rows.

With reference now to FIG. 34, stent 550 comprises yet another configuration of slide-and-lock elements which are interconnected to provide a tubular member sized for deployment in a body lumen. Similar to the stent described above with respect to FIG. 33, in this embodiment, a plurality of interconnected rows 550A-550D is provided wherein each row preferably extends along the entire axial length of the stent 550. Although the stent 550 shown in FIG. 34 is illustrated with four interconnected rows 550A-550D, the number and length of the rows may vary to meet the particular requirements of the application.

Figure 34A:
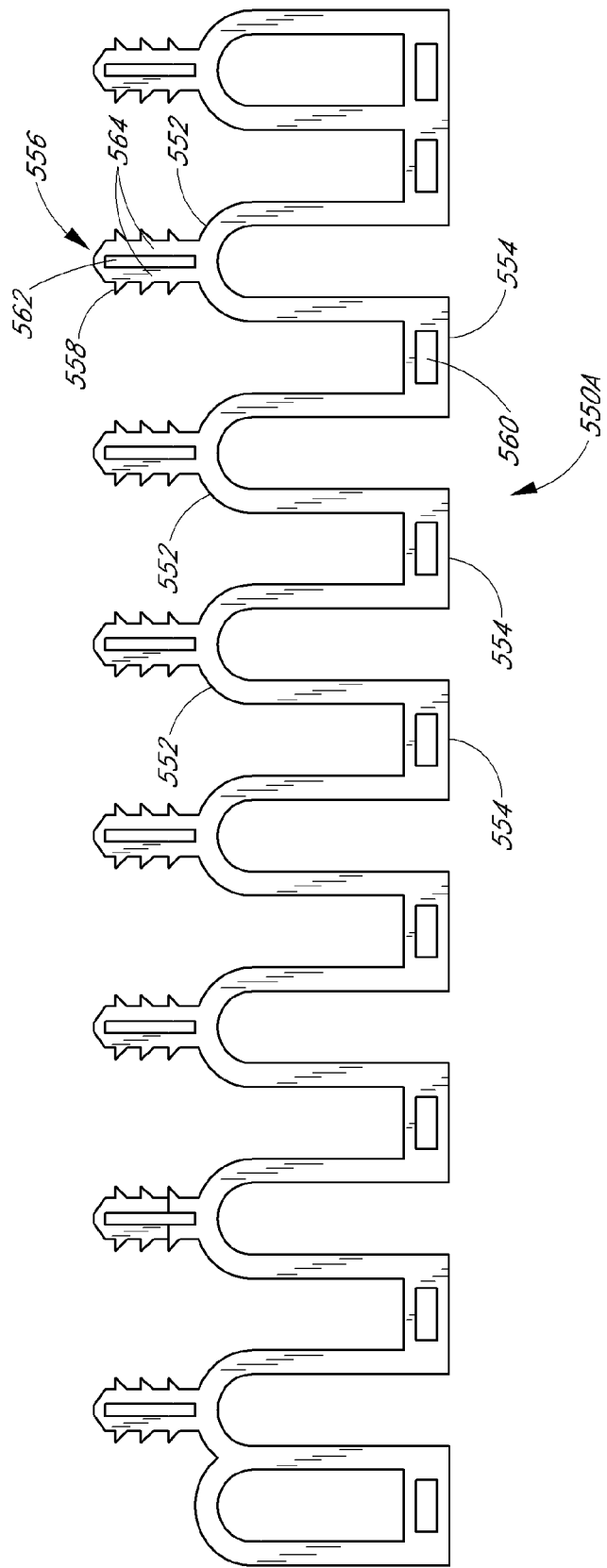
FIG. 34A is a plan view illustrating a single flexible row from the stent embodiment of FIG. 34.

With reference now to FIG. 34A, a single row 550A comprises a structure shaped for providing the stent with excellent flexibility. This feature allows the stent to bend during delivery and to more easily conform to the shape of a body lumen after deployment. The row illustrated in FIG. 34A includes a series of peaks 552 and valleys 554 wherein each peak is provided with a protrusion 556 and each valley is provided with a slot extending therethrough. Each of the protrusions 556 is preferably provided with two deflectable members 564 formed with a number of teeth 558. Each of the teeth 558 is formed with an angled side and a flat side. Furthermore, each of the protrusions 556 is formed with a gap 562 extending between the deflectable members 564. When assembled, the protrusions 556 are slidably received within the slots 560 as illustrated in FIG. 34. The interaction between the angled teeth 558 and slots 560 is preferably configured to provide a stent 550 exhibiting mono-directional expansion. In particular, during expansion, the interaction between the teeth 558 and the slot 560 causes the deflectable members 564 to flex inward for allowing the teeth to pass through the slot 560. The deflectable members 564 are caused to flex inward because the sides of the gap act on the angled side of the teeth. However, when a force is applied in the opposite direction, the flat sides of the teeth abut against the sides of the gap and no inward force is produced. Accordingly, the teeth 558 are prevented from sliding back out of the slots 560, thereby maintaining the stent in the expanded condition after deployment at a treatment site.

With reference again to the embodiment illustrated in FIG. 34, the protrusions preferably pass in a radial direction through the gaps in the adjacent rows. After deployment, an end portion of each protrusion may protrude radially outward from the tubular member, as shown in FIG. 34. The end portions may advantageously provide an anchoring mechanism for further securing the stent 550 at the treatment site after deployment. In another advantageous feature, the stent embodiment 550 illustrated in FIG. 34 may be constructed in an inexpensive manner and provides a modular design that may be combined in a variety of different ways to provide an expandable stent suited for a particular purpose.

Figure 35A:
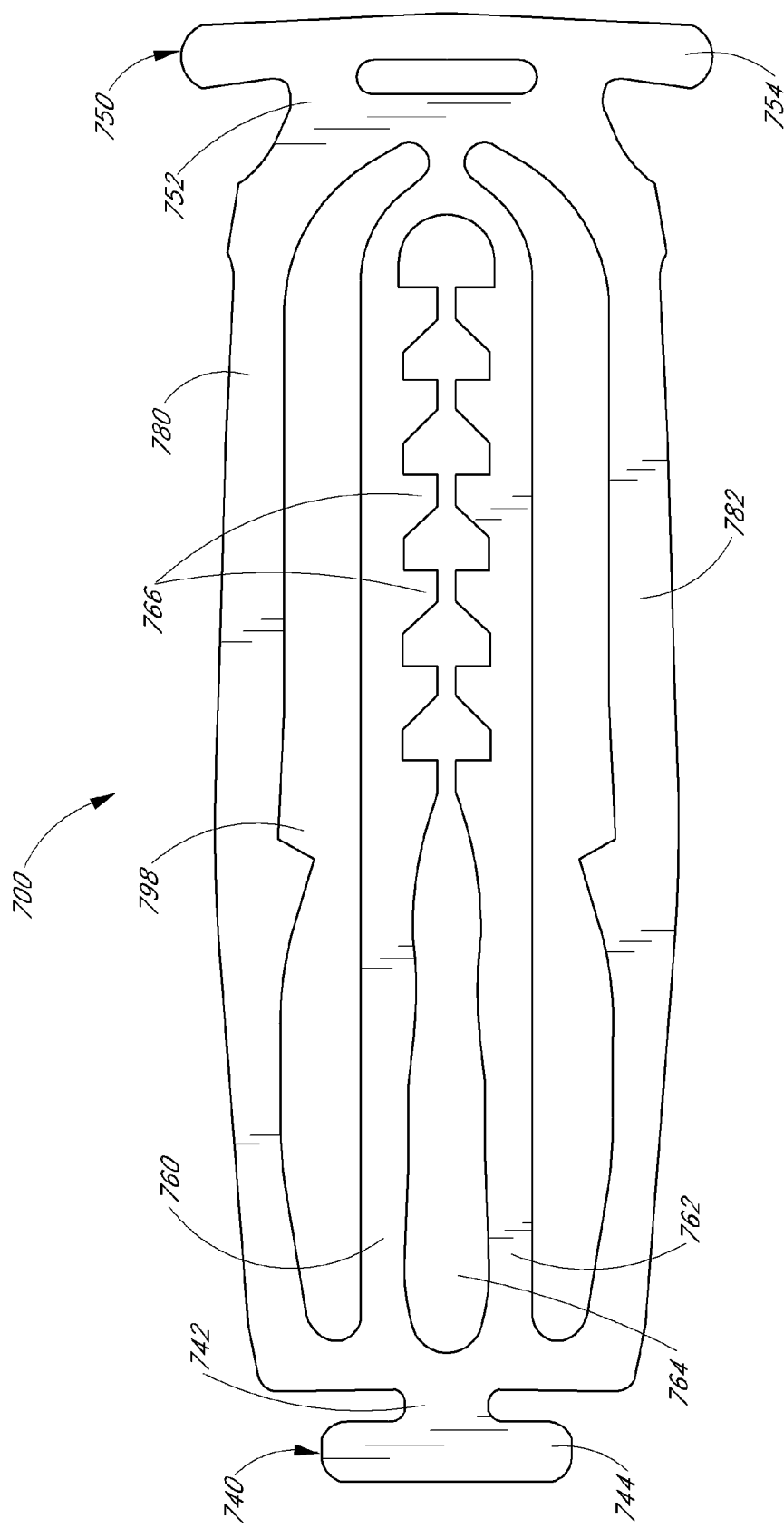
FIG. 35A is a plan view illustrating another preferred embodiment of an expandable stent comprising a single element that may be rolled onto itself to form a tubular member.
Figure 35B:
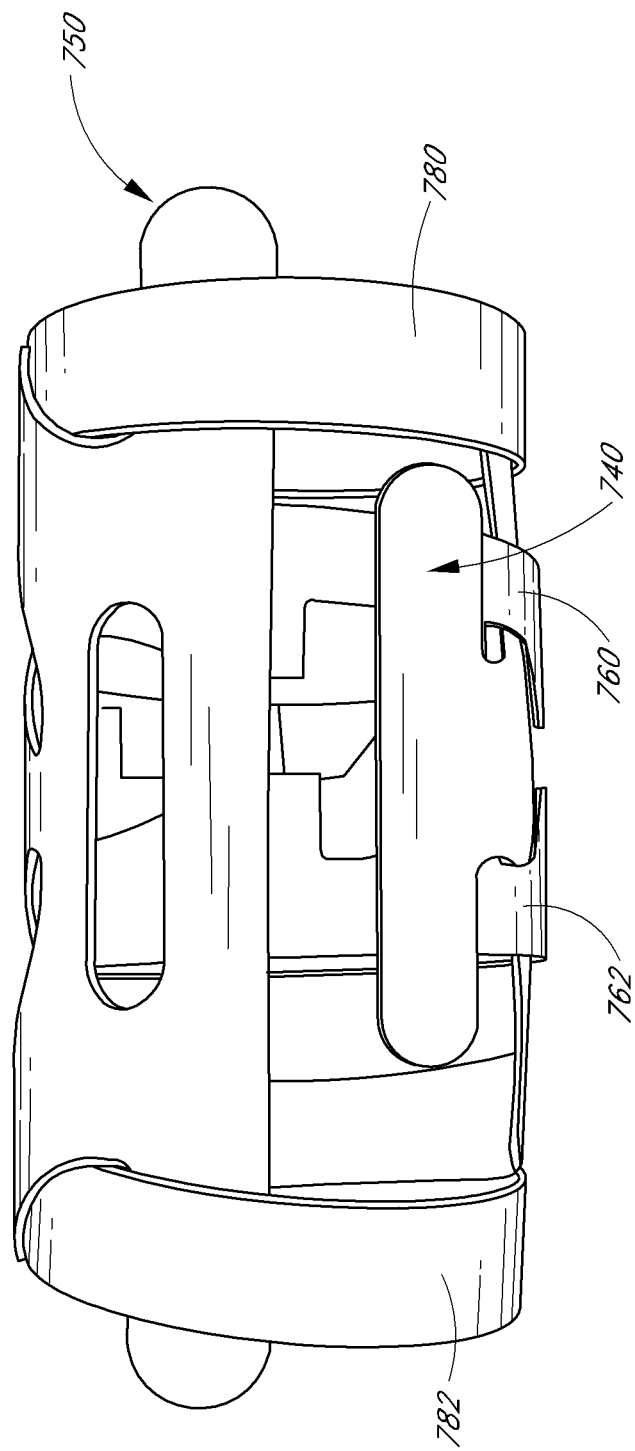
FIG. 35B illustrates the single element of FIG. 35A rolled into a tubular member and constrained in the collapsed condition.

FIGS. 35A-C illustrate yet another alternative embodiment of the present invention wherein an expandable stent is formed from a single element 700. The single element 700 may function in a manner similar to certain embodiments described above. More particularly, the element 700 includes a locking tab 740 having a wide head portion 744 and a thin neck portion 742. In embodiments where the stent is fabricated from a shape-memory material (e.g., Nitinol), the stent may optionally include a hold-down tab 750 having a wide head portion 754 and a thin neck portion 752. Still further, the stent includes first and second deflectable members 760, 762 formed with teeth 766 along an inner edge. The element 700 also includes first and second containment members 780, 782 disposed in parallel to the deflectable members. As illustrated in FIG. 35B, the single radial element is rolled onto itself to provide a tubular member with the head portion 742 of the locking tab 740 extending through a gap 764 between the deflectable members 760, 762. When in the collapsed condition, as shown in FIG. 35B, the optional hold-down tab 750 is held within recesses (see element 788 of FIG. 35A) that prevents the stent from expanding during delivery to a treatment site. However, during delivery, the optional hold-down tab 750 may be released from the recesses 788 and the diameter of the radial element expands. During expansion, the locking tab 740 passes through the teeth 766 along the deflectable members 760, 762 until the stent is expanded to the desired diameter, as shown in FIG. 35C. The configurations of the teeth prevent the locking tab 740 from moving back, thereby ensuring that the stent is held in the expanded condition. In an advantageous feature, this embodiment, which has a "jelly-roll" configuration, does not involve any interconnected components and therefore benefits from simplicity in construction. Accordingly, during use, this embodiment provides excellent reliability and structural integrity.

Although a stent formed from a single integral element is described above as having particular mechanical characteristics for locking the stent in the expanded condition, a variety of other "slide-and-lock" mechanisms may be used without departing from the scope of the invention. For example, other suitable locking mechanism may be found in U.S. Pat. No. 5,344,426 to Lau, U.S. Pat. Nos. 5,735,872 and 5,876,419 to Carpenter, U.S. Pat. No. 5,741,293 to Wijay, U.S. Pat. No. 5,984,963 to Ryan, U.S. Pat. Nos. 5,441,515 and 5,618,299 by Khosravi, U.S. Pat. No. 5,306,286 to Stack, U.S. Pat. No. 5,443,500 to Sigwart, U.S. Pat. No. 5,449,382 to Dayton, U.S. Pat. No. 6,409,752 to Boatman, and the like. Each of these references is incorporated by reference herein. In addition, many of the slide-and-lock mechanisms disclosed in the above patents may be suitable for use with stents embodiments comprising slidable interconnected elements of the type described above.

Although certain preferred embodiments are described above as providing mono-directional expansion during stent deployment, it will be appreciated that, in another mode of the present invention, the teeth or other engaging elements may be shaped and positioned to allow bi-directional movement (i.e., both expansion and contraction). More particularly, the teeth may be constructed to allow for two-way movement between adjacent radial elements, such that the stent diameter may be collapsed after deployment. The teeth create a barrier that resists the stent from expanding or reducing in diameter. However, the resistance created by the teeth may be overcome during placement of the stent on a balloon and during deployment in the vessel. Preferably, the amount of resistance created by the teeth is selected such that the stent diameter will not reduce due to external pressures after deployment in the vessel. However, the teeth do not provide a locking mechanism that limits stent movement to mono-directional expansion. Accordingly, the diameter of the stent may be reduced for placement on an expandable member. This feature provides a constraining or "hold-down" mechanism that allows the stent to be placed on expandable member and also prevents the stent from expanding prematurely. This embodiment advantageously obviates the need for deformable tabs, pins, crimping mechanisms or other hold-down mechanisms.

Metal Stents and Methods of Manufacturing

Preferred materials for making the stents in accordance with some embodiments of the invention include cobalt chrome, 316 stainless steel, tantalum, titanium, tungsten, gold, platinum, iridium, rhodium and alloys thereof or pyrolytic carbon. In still other alternative embodiments, the stents may be formed of a corrodible material, for instance, a magnesium alloy. Although preferred stent embodiments have been described as being conventional balloon expandable stents, those skilled in the art will appreciate that stent constructions according to the present invention may also be formed from a variety of other materials to make a stent crush-recoverable. For example, in alternative embodiments, such as self expandable stents, shape memory alloys that allow for such as Nitinol and Elastinite® may be used in accordance with embodiments of the invention.

Preferably, sheets are work-hardened prior to forming of the individual stent elements to increase strength. Methods of work hardening are well known in the art. Sheets are rolled under tension, annealed under heat and then re-worked. This may be continued until the desired modulus of hardness is obtained. Most stents in commercial use today employ 0% to 10% work hardened material in order to allow for "softer" material to deform to a larger diameter. In contrast, because expansion of the sliding and locking radial elements in accordance with embodiments of the invention depends on sliding rather than material deformation, it is preferred to use harder materials, preferably in the range of about 25-95% work hardened material to allow for thinner stent thickness. More preferably, the stent materials are 50-90% work hardened and most preferably, the materials are 80-85% work hardened.

Preferred methods of forming the individual elements from the metal sheets may be laser cutting, laser ablation, die-cutting, chemical etching, plasma etching and stamping and water jet cutting of either tube or flat sheet material or other methods known in the art which are capable of producing high-resolution components. The method of manufacture, in some embodiments, depends on the material used to form the stent. Chemical etching provides high-resolution components at relatively low price, particularly in comparison to high cost of competitive product laser cutting. Some methods allow for different front and back etch artwork, which could result in chamfered edges, which may be desirable to help improve engagements of lockouts. Further one may use plasma etching or other methods known in the art which are capable of producing high-resolution and polished components. The current invention is not limited to the means by which stent or stent elements can be fabricated.

Once the base geometry is achieved, the elements can be assembled numerous ways. Tack-welding, adhesives, mechanical attachment (snap-together and/or weave together), and other art-recognized methods of attachment, may be used to fasten the individual elements. Some methods allow for different front and back etch artwork, which could result in chamfered edges, which may be desirable to help improve engagements of lockouts. In one preferred method of manufacture, the components of the stent may be heat set at various desired curvatures. For example, the stent may be set to have a diameter equal to that of the deflated balloon, as deployed, at a maximum diameter, or greater than the maximum diameter. In yet another example, elements can be electropolished and then assembled, or electropolished, coated, and then assembled, or assembled and then electropolished.

In another embodiment, in particular with shape memory alloys, the stent is heat set at beyond the maximum diameter then built mid diameter than placed over catheter and reverse ratcheted and locked into smaller diameter and onto catheter with positive catch hold down mechanism to achieve a small profile and excellent retention.

Polymeric Stents

While metal stents possess certain desirable characteristics, the useful lifespan of a stent is estimated to be in the range of about 6 to 9 months, the time at which in-stent restenosis stabilizes and healing plateaus. In contrast to a metal stent, a bioresorbable stent may not outlive its usefulness within the vessel. Moreover, a bioresorbable stent may be used to deliver a greater dose of a therapeutic agent, deliver multiple therapeutic agents at the same time or at various times of its life cycle, to treat specific aspects or events of vascular disease. Additionally, a bioresorbable stent may also allow for repeat treatment of the same approximate region of the blood vessel. Accordingly, there remains an important unmet need to develop temporary (i.e., bioresorbable) and radiopaque stents, wherein the polymeric materials used to fabricate these stents have the desirable qualities of metal (e.g., sufficient radial strength and radiopacity, etc.), while circumventing or alleviating the many disadvantages or limitations associated with the use of permanent metal stents.

In one preferred embodiment, the stent may be formed from biocompatible polymers that are bio-resorbable (e.g., bio-erodible or bio-degradable). Bio-resorbable materials are preferably selected from the group consisting of any hydrolytically degradable and/or enzymatically degradable biomaterial. Examples of suitable degradable polymers include, but are not limited to, polyhydroxybutyrate/polyhydroxyvalerate copolymers (PHV/PHB), polyesteramides, polylactic acid, hydroxy acids (i.e. lactide, glycolide, hydroxybutyrate), polyglycolic acid, lactone based polymers, polycaprolactone, poly(propylene fumarate-co-ethylene glycol) copolymer (aka fumarate anhydrides), polyamides, polyanhydride esters, polyanhydrides, polylactic acid/polyglycolic acid with a calcium phosphate glass, polyorthesters, silk-elastin polymers, polyphosphazenes, copolymers of polylactic acid and polyglycolic acid and polycaprolactone, aliphatic polyurethanes, polyhydroxy acids, polyether esters, polyesters, polydepsidpetides, polysaccharides, polyhydroxyalkanoates, and copolymers thereof.

In one mode, the degradable materials are selected from the group consisting of poly(glycolide-trimethylene carbonate), poly(alkylene oxalates), polyaspartimic acid, polyglutarunic acid polymer, poly-p-dioxanone, poly-.beta.-dioxanone, asymmetrically 3,6-substituted poly-1,4-dioxane-2,5-diones, polyalkyl-2-cyanoacrylates, polydepsipeptides (glycine-DL-lactide copolymer), polydihydropyranes, polyalkyl-2-cyanoacrylates, poly-.beta.-maleic acid (PMLA), polyalkanotes and poly-.beta.-alkanoic acids. There are many other degradable materials known in the art. (See e.g., Biomaterials Science: An Introduction to Materials in Medicine (29 Jul., 2004) Ratner, Hoffman, Schoen, and Lemons; and Atala, A., Mooney, D. Synthetic Biodegradable Polymer Scaffolds. 1997 Birkhauser, Boston; incorporated herein by reference).

Further still, in a more preferred embodiment, the stents may be formed of a polycarbonate material, such as, for example, tyrosine-derived polycarbonates, tyrosine-derived polyarylates, iodinated and/or brominated tyrosine-derived polycarbonates, iodinated and/or brominated tyrosine-derived polyarylates. For additional information, see U.S. Pat. Nos. 5,099,060, 5,198,507, 5,587,507, 5,658,995, 6,048,521, 6,120,491, 6,319,492, 6,475,477, 5,317,077, and 5,216,115, each of which is incorporated by reference herein. In another preferred embodiment, the polymer is any of the biocompatible, bioabsorbable, radiopaque polymers disclosed in U.S. Patent Application Nos. 60/601,526; 60/586,796; and 10/952,202 the entire disclosures of which are incorporated herein by reference thereto.

Natural polymers (biopolymers) include any protein or peptide. Preferred biopolymers may be selected from the group consisting of alginate, cellulose and ester, chitosan, collagen, dextran, elastin, fibrin, gelatin, hyaluronic acid, hydroxyapatite, spider silk, cotton, other polypeptides and proteins, and any combinations thereof.

In yet another alternative embodiment, shape-shifting polymers may be used to fabricate stents constructed according to the present invention. Suitable shape-shifting polymers may be selected from the group consisting of polyhydroxy acids, polyorthoesters, polyether esters, polyesters, polyamides, polyesteramides, polydepsidpetides, aliphatic polyurethanes, polysaccharides, polyhydroxyalkanoates, and copolymers thereof. For addition disclosure on bio-degradable shape-shifting polymers, see U.S. Pat. No. 6,160,084, which is incorporated by reference herein. For additional disclosure on shape memory polymers, see U.S. Pat. Nos. 6,388,043 and 6,720,402, each of which are incorporated by reference herein. Further the transition temperature may be set such that the stent is in a collapsed condition at a normal body temperature. However, with the application of heat during stent placement and delivery, such as via a hot balloon catheter or a hot liquid (e.g., saline) perfusion system, the stent expands to assume its final diameter in the body lumen. When a thermal memory material is used, it may provide a crush-recoverable structure.

Further still, stents may be formed from biocompatible polymers that are biostable (e.g., non-degrading and non-erodible). Examples of suitable non-degrading materials include, but are not limited to, polyurethane, Delrin, high density polyethylene, polypropylene, and poly(dimethyl siloxane).

In some embodiments, the layers may comprise or contain any example of thermoplastics, such as the following, among others: fluorinated ethylene-propylene, poly(2-hydroxyethlmethacrylate (aka pHEMA), poly(ethylene terephthalate) fiber (aka Dacron®) or film (Mylar®), poly(methyl methacrylate (aka PMMA), Poly(tetrafluoroethylene) (aka PTFE and ePTFE and Gore-Tex®), poly(vinylchloride), polyacrylates and polyacrylonitrile (PAN), polyamides (aka Nylon), polycarbonates and polycarbonate urethanes, polyethylene and poly(ethylene-co-vinyl acetate), polypropylene, polypropylene, polystyrene, polysulphone, polyurethane and polyetherurethane elastomers such as Pellethane® and Estane®, Silicone rubbers, Siloxane, polydimethylsiloxane (aka PDMS), Silastic®, Siliconized Polyurethane.

Methods of Manufacturing and Assembling Polymeric Stents

Where plastic and/or degradable materials are used, the elements may be made using laser ablation with a screen, stencil or mask; solvent casting; forming by stamping, embossing, compression molding, centripetal spin casting and molding; extrusion and cutting, three-dimensional rapid prototyping using solid free-form fabrication technology, stereolithography, selective laser sintering, or the like; etching techniques comprising plasma etching; textile manufacturing methods comprising felting, knitting, or weaving; molding techniques comprising fused deposition modeling, injection molding, room temperature vulcanized molding, or silicone rubber molding; casting techniques comprising casting with solvents, direct shell production casting, investment casting, pressure die casting, resin injection, resin processing electroforming, or injection molding or reaction injection molding. Certain preferred embodiments with the present polymers may be shaped into stents via combinations of two or more thereof, and the like.

Such processes may further include two-dimensional methods of fabrication such as cutting extruded sheets of polymer, via laser cutting, etching, mechanical cutting, or other methods, and assembling the resulting cut portions into stents, or similar methods of three-dimensional fabrication of devices from solid forms. For additional information, see U.S. patent application Ser. No. 10/655,338, which is incorporated by reference herein.

Stents of the preferred embodiment are manufactured with elements prepared in full stent lengths or in partial lengths of which two or more are then connected or attached. If using partial lengths, two or more may be connected or attached to comprise a full length stent. In this arrangement the parts are assembled to give rise to a central opening. The assembled full or partial length parts and/or modules may be assembled by inter-weaving them in various states, from a collapsed state, to a partially expanded state, to an expanded state.

Further, elements may be connected or attached by solvent or thermal bonding, or by mechanical attachment. If bonding, preferred methods of bonding comprise the use of ultrasonic radiofrequency or other thermal methods, and by solvents or adhesives or ultraviolet curing processes or photoreactive processes. The elements may be rolled by thermal forming, cold forming, solvent weakening forming and evaporation, or by preforming parts before linking.

Another method of manufacture allows for assembly of the stent components that have been cut out and assembled into flat series of radial elements. The linkage elements between longitudinally adjacent series of radial elements may be connected (e.g., by welding, inter-weaving frame elements, etc.), the flat sheets of material are rolled to form a tubular member. Coupling arms from floating coupling elements and end portions may be joined (e.g., by welding) to maintain the tubular shape. In embodiments that do not include coupling elements, the end portions of the top and bottom radial elements in a series may be joined. Alternatively, where sliding is desired throughout the entire circumference, a sliding and locking articulation can be made between the end portion of the top radial element and the rib(s)/rails of the bottom radial element (e.g., by tack-welding, heat-staking or snap-together). Similarly, a corresponding articulation can be made between the end portion of the bottom radial element and the rib(s)/rails of the top radial element.

Rolling of the flat series of module(s) to form a tubular member can be accomplished by any means known in the art, including rolling between two plates, which are each padded on the side in contact with the stent elements. One plate is held immobile and the other can move laterally with respect to the other. Thus, the stent elements sandwiched between the plates may be rolled about a mandrel by the movement of the plates relative to one another. Alternatively, 3-way spindle methods known in the art may also be used to roll the tubular member. Other rolling methods that may be used in accordance with the present invention include those used for "jelly-roll" designs, as disclosed for example, in U.S. Pat. Nos. 5,421, 955, 5,441,515, 5,618,299, 5,443,500, 5,649,977, 5,643,314 and 5,735,872; the disclosures of which are incorporated herein in their entireties by reference thereto.

The construction of the slide-and-lock stents in these fashions provides a great deal of benefit over the prior art. The construction of the locking mechanism is largely material-independent. This allows the structure of the stent to comprise high strength materials, not possible with designs that require deformation of the material to complete the locking mechanism. The incorporation of these materials will allow the thickness required of the material to decrease, while retaining the strength characteristics of thicker stents. In preferred embodiments, the frequency of catches, stops or teeth present on selected circumferential elements prevents unnecessary recoil of the stent subsequent to expansion.

Radiopacity

Traditional methods for adding radiopacity to a medical product include the use of metal bands, inserts and/or markers, electrochemical deposition (i.e., electroplating), or coatings. The addition of radiopacifiers (i.e., radiopaque materials) to facilitate tracking and positioning of the stent could be accommodated by adding such an element in any fabrication method, by absorbing into or spraying onto the surface of part or all of the device. The degree of radiopacity contrast can be altered by element content.

For plastics and coatings, radiopacity may be imparted by use of monomers or polymers comprising iodine or other radiopaque elements, i.e., inherently radiopaque materials. Common radiopaque materials include barium sulfate, bismuth subcarbonate, and zirconium dioxide. Other radiopaque elements include: cadmium, tungsten, gold, tantalum, bismuth, platium, iridium, and rhodium. In one preferred embodiment, a halogen such as iodine and/or bromine may be employed for its radiopacity and antimicrobial properties.

Multi-Material Vascular Prosthesis

In still other alternative embodiments, various materials (e.g., metals, polymers, ceramics, and therapeutic agents) may be used to fabricate stent embodiments. The embodiments may comprise: 1) differentially layered materials (through the vertical or radial axis) to create a stack of materials (materials may be stacked in any configuration, e.g., parallel, staggered, etc.); 2) spatially localized materials which may vary along the long axis and/or thickness of the stent body; 3) materials that are mixed or fused to create a composite stent body; 4) embodiments whereby a material is laminated (or coated) on the surface of the stent body (see Stent Surface Coatings with Functional Properties as well as see Therapeutic Agents Delivered by Stents); and, 5) stents comprised of 2 or more parts where at least one part is materially distinct from a second part, or any combination thereof.

The fashioning of a slide-and-lock multi-material stent can have between two or more materials. Thickness of each material may vary relative to other materials. This approach as needed or desired allows an overall structural member to be built with each material having one or more functions contributing towards enabling prosthesis function which includes, but is not limited to: 1) enabling mechanical properties for stent performance as defined by ultimate tensile strength, yield strength, Young's modulus, elongation at yield, elongation at break, and Poisson's ratio; 2) enabling the thickness of the substrate, geometrical shape (e.g., bifurcated, variable surface coverage); 3) enabling chemical properties of the material that bear relevance to the materials performance and physical state such as rate of degradation and resorption (which may impact therapeutic delivery), glass transition temperature, melting temperature, molecular weight; 4) enabling radiopacity or other forms of visibility and detection; 5) enabling radiation emission; 6) enabling delivery of a therapeutic agent (see Therapeutic Agents Delivered by Stents); and 7) enabling stent retention and/or other functional properties (see Stent Surface Coatings with Functional Properties).

In some embodiments, the materials may comprise load-bearing properties, elastomeric properties, mechanical strength that is specific to a direction or orientation e.g., parallel to another material and/or to the long axis of the stent, or perpendicular or uniform strength to another material and/or stent. The materials may comprise stiffeners, such as the following, boron or carbon fibers, pyrolytic carbon. Further, stents may be comprised of at least one re-inforcement such a fibers, nanoparticles or the like.

In another preferred mode of the invention, the stent is made, at least in part, from a polymeric material, which may be degradable. The motivation for using a degradable stent is that the mechanical support of a stent may only be necessary for several weeks. In some embodiments, bioresorbable materials with varying rates of resorption may be employed. For additional information, see U.S. patent application Ser. No. 10/952,202 and 60/601,526, which are incorporated by reference herein. Degradable polymeric stent materials may be particularly useful if it also controls restenosis and thrombosis by delivering pharmacologic agents. Degradable materials are well suited for therapeutic delivery (see Therapeutic Agents Delivered by Stents).

In some embodiments, the materials may comprise or contain any class of degradable polymer as previously defined. Along with variation in the time of degradation and/or resorption the degradable polymer may have other qualities that are desirable. For example, in some embodiments the materials may comprise or contain any example of natural polymers (biopolymers) and/or those that degrade by hydrolytic and/or enzymatic action. In some embodiments, the material may comprise or contain any example of hydrogels that may or may not be thermally reversible hydrogels, or any example of a light or energy curable material, or magnetically stimulateable (responding) material. Each of these responses may provide for a specific functionality.

In some embodiments, the materials may comprise or be made from or with constituents which has some radiopaque material alternatively, a clinically visible material which is visible by x-ray, fluoroscopy, ultrasound, MRI, or Imatron Electron Beam Tomography (EBT).

In some embodiments, one or more of the materials may emit predetermined or prescribed levels of therapeutic radiation. In one embodiment, the material can be charged with beta radiation. In another embodiment, the material can be charged with Gamma radiation. In yet another embodiment, the material can be charged with a combination of both Beta and Gamma radiation. Stent radioisotopes that may be used include, but are not limited to, 103-Pd and 32P (phosphorus-32) and two neutron-activated examples, 65Cu and 87Rb2O, (90)Sr, tungsten-188 (188).

In some embodiments, one or more of the materials may comprise or contain a therapeutic agent. The therapeutic agents may have unique, delivery kinetics, mode of action, dose, half-life, purpose, et cetera. In some embodiments, one or more of the materials comprise an agent which provides a mode and site of action for therapy for example by a mode of action in the extracellular space, cell membrane, cytoplasm, nucleus and/or other intracellular organelle. Additionally an agent that serves as a chemoattractant for specific cell types to influence tissue formation and cellular responses for example host-biomaterial interactions, including anti-cancer effects. In some embodiments, one or more of the materials deliver cells in any form or state of development or origin. These could for example be encapsulated in a degradable microsphere, or mixed directly with polymer, or hydrogel and serve as vehicle for pharmaceutical delivery. Living cells could be used to continuously deliver pharmaceutical type molecules, for instance, cytokines and growth factors. Nonliving cells may serve as a limited release system. For additional concepts of therapeutic delivery, see the section entitled: Therapeutic Agents Delivered by Stents.

Therapeutic Agents Delivered by Stents

In another preferred variation, the stent further comprises an amount of a therapeutic agent (as previously defined for a pharmaceutical agent and/or a biologic agent) sufficient to exert a selected therapeutic effect. In some preferred embodiments of the stent (e.g., polymer stents and multi-material stents) the therapeutic agent is contained within the stent as the agent is blended with the polymer or admixed by other means known to those skilled in the art. In other preferred embodiments of the stent, the therapeutic agent is delivered from a polymer coating on the stent surface. In some preferred embodiments of the stent a therapeutic agent is localized in or around a specific structural aspect of the device.

In another preferred variation the therapeutic agent is delivered by means of a non-polymer coating. In other preferred embodiments of the stent, the therapeutic agent is delivered from at least one region or one surface of the stent. The therapeutic can be chemically bonded to the polymer or carrier used for delivery of the therapeutic from at least one portion of the stent and/or the therapeutic can be chemically bonded to the polymer that comprises at least one portion of the stent body. In one preferred embodiment, more than one therapeutic agent may be delivered.

The amount of the therapeutic agent is preferably sufficient to inhibit restenosis or thrombosis or to affect some other state of the stented tissue, for instance, heal a vulnerable plaque, and/or prevent rupture or stimulate endothelialization or limit other cell types from proliferating and from producing and depositing extracellular matrix molecules. The agent(s) may be selected from the group consisting of antiproliferative agents, anti-inflammatory, anti-matrix metalloproteinase, and lipid lowering, cholesterol modifying, anti-thrombotic and antiplatelet agents, in accordance with preferred embodiments of the present invention. Some of these preferred antiproliferative agents that improve vascular patency include without limitation paclitaxel, Rapamycin, ABT-578, everolimus, dexamethasone, nitric oxide modulating molecules for endothelial function, tacrolimus, estradiol, mycophenolic acid, C6-ceramide, actinomycin-D and epothilones, and derivatives and analogs of each.

Some of these preferred agents act as an antiplatelet agent, antithrombin agent, compounds to address other pathologic events and/or vascular diseases. Various therapeutic agents may be classified in terms of their sites of action in the host: agents that exert their actions extracellularly or at specific membrane receptor sites, those that act on the plasma membrane, within the cytoplasm, and/or the nucleus.

In addition to the aforementioned, therapeutic agents may include other pharmaceutical and/or biologic agents intended for purposes of treating body lumens other than arteries and/or veins). Therapeutic agents may be specific for treating nonvascular body lumens such as digestive lumens (e.g., gastrointestinal, duodenum and esophagus, biliary ducts), respiratory lumens (e.g., tracheal and bronchial), and urinary lumens (e.g., urethra). Additionally such embodiments may be useful in lumens of other body systems such as the reproductive, endocrine, hematopoietic and/or the integumentary, musculoskeletal/orthopedic and nervous systems (including auditory and ophthalmic applications); and finally, stent embodiments with therapeutic agents may be useful for expanding an obstructed lumen and for inducing an obstruction (e.g., as in the case of aneurysms).

Therapeutic release may occur by controlled release mechanisms, diffusion, interaction with another agent(s) delivered by intravenous injection, aerosolization, or orally. Release may also occur by application of a magnetic field, an electrical field, or use of ultrasound.

Stent Surface Coatings with Functional Properties

In addition to stents that may deliver a therapeutic agent, for instance delivery of a biological polymer on the stent such as a repellant phosphorylcholine, the stent may be coated with other bioresorbable polymers predetermined to promote biological responses in the body lumen desired for certain clinical effectiveness. Further the coating may be used to mask (temporarily or permanently) the surface properties of the polymer used to comprise the stent embodiment. The coating may be selected from the broad class of any biocompatible bioresorbable polymer which may include any one or combination of halogenated and/or non-halogenated which may or may not comprise any poly(alkylene glycol). These polymers may include compositional variations including homopolymers and heteropolymers, stereoisomers and/or a blend of such polymers. These polymers may include for example, but are not limited to, polycarbonates, polyarylates, poly(ester amides), poly(amide carbonates), trimethylene carbonate, polycaprolactone, polydioxane, polyhydroxybutyrate, poly-hydroxyvalerate, polyglycolide, polylactides and stereoisomers and copolymers thereof, such as glycolide/lactide copolymers. In a preferred embodiment, the stent is coated with a polymer that exhibits a negative charge that repels the negatively charged red blood cells' outer membranes thereby reducing the risk of clot formation. In another preferred embodiment, the stent is coated with a polymer that exhibits an affinity for cells, (e.g., endothelial cells) to promote healing. In yet another preferred embodiment, the stent is coated with a polymer that repels the attachment and/or proliferation of specific cells, for instance arterial fibroblasts and/or smooth muscle cells in order to lessen restenosis and/or inflammatory cells such as macrophages.

Described above are the stents of the present invention that may be modified with a coating to achieve functional properties that support biological responses. Such coatings or compositions of material with a therapeutic agent may be formed on stents or applied in the process of making a stent body via techniques such as dipping, spray coating, cross-linking combinations thereof, and the like. Such coatings or compositions of material may also serve purpose other than delivering a therapeutic, such as to enhance stent retention on a balloon when the coating is placed intraluminally on the stent body and/or placed over the entire device after the stent is mounted on the balloon system to keep the stent in a collapsed formation. Other purposes can be envisioned by those skilled in the art when using any polymer material.

In one aspect of the invention, a stent would have a coating applied that has specific mechanical properties. The properties may include inter alia thickness, tensile strength, glass transition temperature, and surface finish. The coating is preferably applied prior to final crimping or application of the stent to the catheter. The stent may then be applied to the catheter and the system may have either heat or pressure or both applied in a compressive manner. In the process, the coating may form frangible bonds with both the catheter and the other stent surfaces. The bonds would enable a reliable method of creating stent retention and of holding the stent crossing profile over time. The bonds would break upon the balloon deployment pressures. The coating would be a lower Tg than the substrate to ensure no changes in the substrate.

Stent Deployment

First, a catheter is provided wherein an expandable member, preferably an inflatable balloon, such as an angioplasty balloon, is provided along a distal end portion. One example of a balloon catheter for use with a stent is described in U.S. Pat. No. 4,733,665 to Palmaz, which is incorporated by reference herein. A stent on a catheter is commonly collectively referred to as a stent system. Catheters include but are not limited to over-the-wire catheters, coaxial rapid-exchange designs and the Medtronic Zipper Technology that is a new delivery platform. Such catheters may include for instance those described in Bonzel U.S. Pat. Nos. 4,762,129 and 5,232,445 and by Yock U.S. Pat. Nos. 4,748,982; 5,496,346; 5,626,600; 5,040,548; 5,061,273; 5,350,395; 5,451,233 and 5,749,888. Additionally, catheters may include for instance those as described in U.S. Pat. Nos. 4,762,129; 5,092,877; 5,108,416; 5,197,978; 5,232,445; 5,300,085; 5,445,646; 5,496,275; 5,545,135; 5,545,138; 5,549,556; 5,755,708; 5,769,868; 5,800,393; 5,836,965; 5,989,280; 6,019,785; 6,036,715; 5,242,399; 5,158,548; and 6,007,545. The disclosures of the above-cited patents are incorporated herein in their entirety by reference thereto.

Catheters may be specialized with highly compliant polymers and for various purposes such as to produce an ultrasound effect, electric field, magnetic field, light and/or temperature effect. Heating catheters may include for example those described in U.S. Pat. Nos. 5,151,100, 5,230,349; 6,447,508; and 6,562,021 as well as WO9014046A1. Infrared light emitting catheters may include for example those described in U.S. Pat. Nos. 5,910,816 and 5,423,321. The disclosures of the above-cited patents and patent publications are incorporated herein in their entirety by reference thereto.

An expandable member, such as an inflatable balloon, is preferably used to deploy the stent at the treatment site. As the balloon is expanded, the radial force of the balloon overcomes the initial resistance of the constraining mechanism, thereby allowing the stent to expand. As the balloon is inflated, the radial elements slide with respect to each other along the surface of the balloon until the stent has been expanded to a desired diameter.

The stent of embodiments of the invention are adapted for deployment using conventional methods known in the art and employing percutaneous transluminal catheter devices. This includes deployment in a body lumen by means of a balloon expandable design whereby expansion is driven by the balloon expanding. Alternatively, the stent may be mounted onto a catheter that holds the stent as it is delivered through the body lumen and then releases the stent and allows it to self-expand into contact with the body lumen. The restraining means may comprise a removable sheath and/or a mechanical aspect of the stent design.

Some embodiments of the invention may be useful in coronary arteries, carotid arteries, vascular aneurysms (when covered with a sheath), and peripheral arteries and veins (e.g., renal, iliac, femoral, popliteal, subclavian, aorta, intercranial, etc.). Other nonvascular applications include gastrointestinal, duodenum, biliary ducts, esophagus, urethra, reproductive tracts, trachea, and respiratory (e.g., bronchial) ducts. These applications may or may not require a sheath covering the stent.

It is desirable to have the stent radially expand in a uniform manner. Alternatively, the expanded diameter may be variable and determined by the internal diameter and anatomy of the body passageway to be treated. Accordingly, uniform and variable expansion of the stent that is controlled during deployment is not likely to cause a rupture of the body passageway. Furthermore, the stent will resist recoil because the locking means resist sliding of the mating elements. Thus, the expanded intraluminal stent will continue to exert radial pressure outward against the wall of the body passageway and will therefore, not migrate away from the desired location.

From the foregoing description, it will be appreciated that a novel approach for expanding a lumen has been disclosed. While the components, techniques and aspects of the invention have been described with a certain degree of particularity, it is manifest that many changes may be made in the specific designs, constructions and methodology herein above described without departing from the spirit and scope of this disclosure.

While a number of preferred embodiments of the invention and variations thereof have been described in detail, other modifications and methods of using and medical applications for the same will be apparent to those of skill in the art. Accordingly, it should be understood that various applications, modifications, materials, and substitutions may be made of equivalents without departing from the spirit of the invention or the scope of the claims.

Various modifications and applications of the invention may occur to those who are skilled in the art, without departing from the true spirit or scope of the invention. It should be understood that the invention is not limited to the embodiments set forth herein for purposes of exemplification, but is to be defined only by a fair reading of the appended claims, including the full range of equivalency to which each element thereof is entitled.

References

Some of the references cited herein are listed below, the entirety of each one of which is hereby incorporated by reference herein:

Charles R, Sandirasegarane L, Yun J, Bourbon N, Wilson R, Rothstein R P, et al. Ceramide-Coated Balloon Catheters Limit Neointimal Hyperplasia after Stretch Injury in Carotid Arteries. Circ Res 2000; 87(4):282-288.

Coroneos E, Martinez M, McKenna S, Kester M. Differential regulation of sphingomyelinase and ceramidase activities by growth factors and cytokines. Implications for cellular proliferation and differentiation. J Biol Chem 1995; 270(40):23305-9.

Coroneos E, Wang Y, Panuska J R, Templeton D J, Kester M. Sphingolipid metabolites differentially regulate extracellular signal-regulated kinase and stress-activated protein kinase cascades. Biochem J 1996; 316(Pt 1):13-7.

Jacobs L S, Kester M. Sphingolipids as mediators of effects of platelet-derived growth factor in vascular smooth muscle cells. Am J Physiol 1993; 265(3 Pt 1):C740-7.

Tanguay J F, Zidar J P, Phillips H R, 3rd, Stack R S. Current status of biodegradable stents. Cardiol Clin 1994; 12(4): 699-713.

Nikol S, Huehns T Y, Hofling B. Molecular biology and post-angioplasty restenosis. Atherosclerosis 1996; 123 (1-2): 17-31.

Biomaterials Science: An Introduction to Materials in Medicine (29 Jul., 2004) Ratner, Hoffman, Schoen, and Lemons

What is claimed is:

1. A slide-and-lock stent, comprising a tubular member having longitudinal, radial, and circumferential axes, and luminal and abluminal surfaces, the tubular member comprising:

a first longitudinal module and a second longitudinal module, the first longitudinal module and the second longitudinal module each comprising:

a first end, a second end longitudinally opposite the first end, and an intermediate portion joining the first end and the second end, the first end comprising a closed loop, the closed loop comprising an opening that extends between the luminal and abluminal surfaces, wherein a longitudinal axis of the closed loop extends parallel to the circumferential axis of the tubular member; and a spine extending along the intermediate portion, the spine comprising alternating peaks and valleys;

a protrusion extending from at least one of the peaks of the first longitudinal module, the protrusion comprising a first lockout tooth and a second lockout tooth; and a slot extending through a region of at least one of the valleys of the second longitudinal module;

wherein the protrusion of the first longitudinal module is configured to slidably engage with the slot of the second longitudinal module thereby circumferentially engaging the first longitudinal module and the second longitudinal module, wherein the lockout tooth is configured to allow one-way slidable movement of the first longitudinal module relative to the second longitudinal module during expansion of the tubular member from a radially unexpanded state to a radially expanded state.

2. The slide-and-lock stent of claim 1, wherein the second end comprises a second closed loop.

3. The slide-and-lock stent of claim 1, wherein each of the peaks is longitudinally adjacent at least one of the valleys, the longitudinally adjacent peaks and valleys being circumferentially separated by an amplitude, the amplitude being substantially constant along the spine.

4. The slide-and-lock stent of claim 1, wherein the spine has a generally sinusoidal shape.

5. The slide-and-lock stent of claim 1, wherein the protrusion comprises a first lockout tooth configured to provide a first level of resistance to the expansion of the tubular member and a second lockout tooth configured to provide a second level of resistance to the expansion of the tubular member.

6. The slide-and-lock stent of claim 5, wherein:
the first lockout tooth is configured to engage with the slot prior to the second lockout tooth engaging with the slot during expansion of the tubular member from the radially unexpanded state to the radially expanded state; and
the first level of resistance is greater than the second level of resistance.

7. The slide-and-lock stent of claim 1, wherein the stent has no flexible linkage elements.

8. The slide-and-lock stent of claim 1, wherein the protrusion further comprises two deflectable members having a gap therebetween, the deflectable members being configured to flex longitudinally as the lockout tooth engages with the slot.

9. The slide-and-lock stent of claim 1, wherein the protrusion has a radial thickness that is less than a radial thickness of the spine.

10. The slide-and-lock stent of claim 9, the radial thickness of the stent is substantially constant.

11. The slide-and-lock stent of claim 1, wherein:
the modules comprise (n) material layers, wherein (n) is at least two;
wherein the protrusion and a portion of the spine each comprise less than (n) material layers; and
the total number of material layers at the portion of the spine equals (n) when the protrusion from the first module is slidably engaged within the slot from the second module, such that the thickness of the slide-and-lock stent is uniform and does not exceed (n) layers.

12. The slide-and-lock stent of claim 1, wherein a cross-sectional geometry of at least a portion of the stent is tapered so as to produce generally uniform blood flow characteristics when the stent is placed in a blood vessel lumen.

13. The slide-and-lock stent of claim 1, wherein the first longitudinal module comprises a plurality of protrusions and the second longitudinal module comprises a corresponding plurality of slots, wherein each of the plurality of protrusions is configured to slidably engage the corresponding slot of the plurality of slots.

14. The slide-and-lock stent of claim 13, wherein each of the plurality of protrusions is configured to move independent of the others of the plurality of protrusions, thereby facilitating a diameter of the stent varying along the longitudinal axis.

15. The slide-and-lock stent of claim 1, wherein the slot extends radially through a thickness of the second longitudinal module from a luminal to an abluminal surface of the second longitudinal module.

16. The slide-and-lock stent of claim 1, wherein the at least one of the valleys comprises an apex, and wherein the slot is positioned at the apex.

17. The slide-and-lock stent of claim 1, wherein:
at least one of the valleys comprises an apex; and
a portion of the slot is defined by a longitudinally extending crossmember, the crossmember circumferentially spaced from the apex.

18. The slide-and-lock stent of claim 1, wherein the first longitudinal module further comprises a second slot extending through a region of at least one of the valleys of the first longitudinal modules, and wherein the second longitudinal module further comprises a second protrusion comprising a second lockout tooth and extending from at least one of the peaks of the second longitudinal module;
wherein each protrusion is configured to slidably engage with each slot; and
wherein the second lockout tooth is configured to allow one-way slidable movement of the second longitudinal module relative to the first longitudinal module during expansion of the tubular member from a radially unexpanded state to a radially expanded state.

19. A slide-and-lock stent, comprising a tubular member having longitudinal, radial, and circumferential axes, the tubular member comprising:
a plurality of longitudinal modules, each of the longitudinal modules being monolithic, identical in shape, and comprising:
a first end, a second end longitudinally opposite the first end, and an intermediate portion joining the first end and the second end;
a spine extending along the intermediate portion, the spine comprising alternating peaks and valleys;
a protrusion extending from at least one of the peaks, the protrusion comprising a lockout tooth; and
a slot extending through a region of at least one of the valleys;
wherein the protrusion of a first of the plurality of longitudinal modules is configured to slidably engage with the slot of a second of the plurality of longitudinal modules thereby circumferentially engaging the first of the plurality of longitudinal modules and the second of the plurality of longitudinal modules,
wherein the lockout tooth is configured to allow one-way slidable movement of the first of the plurality of longitudinal modules relative to the second of the plurality of longitudinal modules during expansion of the tubular member from a radially unexpanded state to a radially expanded state.

20. The slide-and-lock stent of claim 19, wherein the lockout tooth extends at least partially radially.

21. A slide-and-lock stent, comprising a tubular member having longitudinal, radial, and circumferential axes, the tubular member configured to expand from a radially collapsed state to a radially expanded state, tubular member comprising:
- a plurality of longitudinal modules, each of the longitudinal modules comprising:
  - a spine comprising a plurality of peaks, a plurality of valleys, and a plurality of struts, the peaks and valley alternating along the longitudinal axis, each of the peaks connected to at least one of the valleys by at least one of the struts, each of the struts extending substantially circumferentially and having a first circumferential length;
  - a protrusion extending substantially circumferentially from at least one of the peaks, the protrusion comprising a lockout tooth, the protrusion having a second circumferential length, the second circumferential length being less than the first circumferential length; and
  - a slot extending through a region of at least one of the valleys, the slot extending from a first closed end to a second closed end in a circumferential direction;
- wherein the protrusion of a first of the plurality of longitudinal modules is configured to slidably engage with the slot of a second of the plurality of longitudinal modules thereby circumferentially engaging the first of the plurality of longitudinal modules and the second of the plurality of longitudinal modules,
- wherein the lockout tooth is configured to allow one-way slidable movement of the first of the plurality of longitudinal modules relative to the second of the plurality of longitudinal modules during expansion of the tubular member from the radially collapsed state to the radially expanded state.

22. The slide-and-lock stent of claim 21, wherein each of the struts is oriented along a plane substantially perpendicular to the longitudinal axis when the tubular member is in the radially collapsed state.

23. A slide-and-lock stent, comprising a tubular member having longitudinal, radial, and circumferential axes, and luminal and abluminal surfaces, the tubular member comprising:
- a first longitudinal module and a second longitudinal module, the first longitudinal module and the second longitudinal module each comprising:
  - a first end, a second end longitudinal opposite the first end and an intermediate portion joining the first end and the second end the first end comprising a closed loop, the closed loop comprising an opening that extends between the luminal and abluminal surfaces; and
  - a spine extending along the intermediate portion, the spine comprising alternating peaks and valleys;
- a protrusion extending from at least one of the peaks of the first longitudinal module, the protrusion comprising a first lockout tooth and a second lockout tooth; and
- a slot extending through a region of at least one of the valleys of the second longitudinal module;
- wherein the protrusion of the first longitudinal module is configured to slidably engaged with the slot of the second longitudinal module thereby circumferentially engaging the first longitudinal module and the second longitudinal module;
- wherein the first lockout tooth and the second lockout tooth are configured to allow one-way slidable movement of the first longitudinal module relative to the second longitudinal module during expansion of the tubular member from a radially unexpanded state to a radially expanded state;
- wherein the first lockout tooth is configured to engage with the slot prior to the second lockout tooth engaging with the slot during expansion of the tubular member from the radially unexpanded state to the radially expanded state; and
- wherein the first lockout tooth is configured to provide a first level of resistance to the expansion of the tubular member and the second lockout tooth is configured to provide a second level of resistance to the expansion of the tubular member, the first level of resistance being greater than the second level of resistance.

* * * * *